(12) United States Patent
Liddle et al.

(10) Patent No.: US 7,531,712 B2
(45) Date of Patent: May 12, 2009

(54) P450 GENE REGULATION

(75) Inventors: Christopher Liddle, Chatswood (AU); Bryan James Goodwin, Parramatta (AU); Graham Robertson, Sydney (AU)

(73) Assignee: The University of Syndey, New South Wales (AU)

( * ) Notice: Subject to any disclaimer, the term of this patent is extended or adjusted under 35 U.S.C. 154(b) by 0 days.

(21) Appl. No.: 10/415,607

(22) PCT Filed: Nov. 1, 2001

(86) PCT No.: PCT/AU01/01407

§ 371 (c)(1),
(2), (4) Date: Nov. 20, 2003

(87) PCT Pub. No.: WO02/36784

PCT Pub. Date: May 10, 2002

(65) Prior Publication Data

US 2005/0076397 A1    Apr. 7, 2005

(30) Foreign Application Priority Data

Nov. 1, 2000  (AU)  .................. PR1161
May 10, 2001  (AU)  .................. PR4901

(51) Int. Cl.
  *G01N 33/00*  (2006.01)
  *A01K 67/00*  (2006.01)
(52) U.S. Cl. .................. 800/3; 800/8; 800/18
(58) Field of Classification Search .............. 800/3, 800/8, 18
  See application file for complete search history.

(56) References Cited

U.S. PATENT DOCUMENTS

| 4,997,757 | A | | 3/1991 | Schiestl | |
|---|---|---|---|---|---|
| 5,429,948 | A | | 7/1995 | Crespi et al. | |
| 5,849,998 | A | * | 12/1998 | Gottesman et al. | ............ 800/18 |
| 6,432,639 | B1 | | 8/2002 | Lichter et al. | |
| 2002/0138855 | A1 | * | 9/2002 | Zhang et al. | ................ 800/3 |
| 2002/0150915 | A1 | | 10/2002 | Berkenstam et al. | |
| 2003/0145341 | A1 | | 7/2003 | Zhang et al. | |

FOREIGN PATENT DOCUMENTS

| EP | 644267 | 3/1995 |
|---|---|---|
| EP | 1206906 | 5/2002 |
| EP | 1047107 B1 | 10/2006 |
| WO | WO 99/13106 | 3/1999 |
| WO | WO 99/35246 | 7/1999 |
| WO | WO 99/48915 A1 | 9/1999 |
| WO | WO 99/61622 | 12/1999 |
| WO | WO 99/61622 A1 | 12/1999 |
| WO | WO 01/11951 | 2/2001 |
| WO | WO 01/20025 | 3/2001 |
| WO | WO 01/20026 | 3/2001 |
| WO | WO 01/57519 A2 | 8/2001 |
| WO | WO 01/79845 | 10/2001 |
| WO | WO 02/08451 | 1/2002 |
| WO | WO 02/25270 | 3/2002 |
| WO | WO 02/052259 A1 | 7/2002 |
| WO | WO 02/036784 | 10/2002 |
| WO | WO 02/083897 | 10/2002 |
| WO | WO 02/088305 | 11/2002 |
| WO | WO 02/095419 A2 | 11/2002 |

OTHER PUBLICATIONS

Robertson GR, Transgenic mouse models of human CYP3A4 gene regulation, 2003, Molecular Pharmacology, vol. 64, pp. 42-50.*
Houdebine LM, The methods to generate transgenic animals and to control transgene expression, 2002, J. of Biotechnology, vol. 98, pp. 145-160.*
Montoliu L, Gene transfer strategies in animal transgenesis, 2002, Cloning and Stem Cells, vol. 4, pp. 39-46.*
Ristevski S, Making better transgenic models, 2005, Molecular Biotechnology, vol. 29, pp. 153-163.*
Smith KR, Gene transfer in higher animals: theoretical considerations and key concepts, J. of Biotechnology, vol. 99, pp. 1-22.*
Hashimoto et al., 1993, Eur. J. Biochem., vol. 218, pp. 585-595 from IDS (Jan. 17, 2006).*
Kamataki T, et al., "Preclinical approach for identifying drug interactions." Cancer Chemother Pharmacol. 1998;42 Suppl:S50-3.
Ogg MS, et al., "Development of an in vitro reporter gene assay to assess xenobiotic induction of the human CYP3A4 gene." Eur J Drug Metab Pharmacokinet. Oct.-Dec. 1997;22(4):311-3.
Olsen Ak, et al., "Pig hepatocytes as an in vitro model to study the regulation of human CYP3A4: prediction of drug-drug interactions with 17 alpha-ethynylestradiol." Chem Biol Interact. Nov. 6, 1997;107(1-2):93-108.
Hashimoto et al., "Gene Structures of CYP3A4, An Adult-Specific Form of Cytochrome P450 in Human Livers, and it's Transcriptional Control" *European Journal of Biochemistry*, vol. 218, No. 2, 1993, pp. 585-595.

(Continued)

*Primary Examiner*—Peter Paras, Jr.
*Assistant Examiner*—David Montanari
(74) *Attorney, Agent, or Firm*—Richard F. Trecartin; Morgan Lewis & Bockius LLP

(57) ABSTRACT

The invention relates to the generation of non-human transgenic animals comprising a reporter construct for producing a detectable amount of a reporter molecule operably linked to a transcriptional regulatory nucleic acid molecule from the human CYP3A4 gene located between the initiation of transcription site of the gene and a position located 13,000 nucleotides upstream from the site. The invention also relates to the use of these animals for determining the effect of a compound, particularly, but not exclusively, a xenobiotic or steriod, on the regulation of expression of the CYP3A4 gene in a human.

8 Claims, 22 Drawing Sheets

OTHER PUBLICATIONS

Lehmann, J.M. et al. "The human orphan nuclear receptor PXR is activated by compounds that regulate CYP3A4 gene expression and cause drug interactions" *Journal of Clinical Investigation*, vol. 102, No. 5, Sep. 1, 1998, pp. 1016-1023.

Achira M. et al., "Comparative studies to determine the selective inhibitors for P-glycoprotein and cytochrome P4503A4", AAPS Pharmsci Electronic Resource, 1999, vol. 1, No. 4, 1999, pp. E18.1-E18.6.

Birren et al. << Mus musculus cloneRp23-161k8, low pass sequence sampling >> XP002382554 retrieved from EBI Database accession No. AC11090 (Online) May 27, 2004.

Dogra S C et al. "Transcriptional activation of cytochrome P450 genes by different classes of chemical inducers." Clinical and Experimental Pharmacology and Physiology, 25: 1-9 (Jan. 1998).

Kolars J C et al. "CYP3A gene expression in human gut epithelium." Pharmacogenetics (1994) 4: 47-259.

Kovaleva l E et al. "Transgenic yeast expressing human cytochrome P450s can serve as a tool in studies of the mechanisms of their induction by various effectors." Biochemical and Biophysical Research Communications (1996) 221(1):129-132.

Hakkola J et al. "Xenobiotic-metabolizing cytochrome P450 enzymes in the human feto-placental unit: role in intrauterine toxicity." Critical Reviews in Toxicology, 28 (1): 35-72 (Jan. 1998).

Gonzalez F J et al. "Human P450PCN1: sequence, chromosome localization, and direct evidence through cDNA expression that P450PCN1 is nifedipine oxidase." DNA (1988) 7(2): 79-86.

Ahern H. "Biochemical, reagent kits offer scientists good return on investment." The Scientist 9(15):20 (Jul. 1995).

Yanagida A et al. "A novel cis-acting DNA element required for a high level of inducible expression of the rat P-450c gene." *Mol Cell Biol*, 10(4):1470-1475 (1990).

Bertilsson G, et al. "Identification of a Human Nuclear, Receptor Defines a New Signalling Pathway for CYP3A Induction", *Proc. Nat'l Acad. Sci.*, USA, 95:12208-12213 (Oct. 1998).

Blumberg B, et al., "SXR, a Novel Steroid and Xenobiotic Sensing Nuclear Receptor", *Genes & Dev.*, 12(20):3195-3205 (1998).

Mangelsdorf D J, et al., "The Nuclear Receptor Superfamily: The Second Decade", *Cell*, 83(6):835-839 (Dec. 1995).

Baes M, et al., "A New Orphan Member of the Nuclear. Hormone Receptor Superfamily that interacts with a Subset of Retinoic Acid Response Elements", *Mol Cell Biol.*, 14(3): 1544-1552 (Mar. 1994).

Rebbeck T R, et al., "Modification of the Clinical Presentation, of Prostate Tumors by a Novel Genetic Variant in CYP3A4", *J Nat'l Cancer Inst.*, 90(16):1225-1229 (Aug. 1998).

Felix C A, et al., "Association of CYP3A4 Genotype with Treatment-Related Leukemia", *Proc. Nat'l Acad. Sci, USA*, 95:13176-13181 (Oct. 1998).

Goodwin B et al, "The orphan human pregnane X receptor mediates the-transcriptional activation of CYP3A4 by rifampicin through a distal enhancer module." *Molecular, Pharmacology*, 56(6):1329-1339 (Dec. 1999).

Goodwin B et al. Genbank Accession No. AF185589.

Martin D I K and Whitelaw E. The vagaries of variegating transgenes. *Bioessays* 18:919-923 (1996).

Robertson, G et al. Position-dependent variegation of globin transgene expression in mice. *Proc. Natl. Acad. Sci. USA* 92:5371-5375 (1995).

Robertson, G et al. Age dependent silencing of globin transgenes in the mouse. *Nucleic Acids Research* 24:1465-1471 (1996).

Dobie K W et al. Variegated transgene expression in mouse mammary gland is determined by the transgene integration locus. *Proc. Natl. Acad. Sci. USA* 93:6659-6664 (1996).

Elliot J et al. Random activation of a transgene under control of a hybrid hCD2 locus control region/Ig enhancer regulatory element. *EMBO J* 14:575-584 (1995).

Henikoff S Conspiracy of silence amongst repeated transgenes. *Bioessays* 20:532-535 (1998).

Garrick D et al. Repeat-induced gene silencing in mammals. *Nature Genetics* 18:56-59 (1998).

Jones S A et al. The pregnane X receptor: a promiscuous xenobiotic receptor that has diverged during evolution. *Mol. Endocrinol.* 14:27-39 (2000).

Wei et al. The nuclear receptor CAR mediates specific xenobiotic induction of drug metabolism. *Nature* 407(6806):920-923 (2000).

Xie W et al. Humanized xenobiotic response in mice expressing nuclear receptor SXR. *Nature* 406(6794):435-9 (2000).

Smith, T.F. and Waterman M.S. "Comparison of biosequences" (1981) *Ad. Appl. Math.*, 2:482-489.

Needleman, S.B. and Wunsch, C.D. "A general method applicable to the search for similarities in the amino acid sequence of two proteins." (1970) *J. Mol. Biol.* 48(3):443-453.

Gellner K et al: "Genomic Organization Of The Human Cyp3a Locus: Identification Of A New, Inducible Cyp3a Gene" *Pharmacogenetics*, 11(2):111-121 (Mar. 2001).

Toide K et al: "Gene structure of mouse Cyp3a11: Evidence for an enhancer element within its 5' flanking sequences" *Archives Of Biochemistry And Biophysics*, 338(1): 43-49 (1997).

Itoh S et al: "Isolation of a promoter region in mouse cytochrome P450 3A (Cyp3A16) gene and its transcriptional control" *Biochimica Et Biophysica ACTA*, 1350(2):155-158 (1997).

Finta C et al. "The human cytochrome P450 3A locus. Gene evolution by capture of downstream exons", *Gene* 260(1-2):13-23 (2000).

MacGregor et al. "New molecular endpoints and methods for routine toxicity testing," *Fundamental and Applied Toxicology* 26(2): 156-173 (1995).

Smith et al., "Molecular genetics of the human cytochrome P450 monooxygenase superfamily," *Xenobiotica* 28(12):1129-1165 (1998).

Yanagimoto et al., "Mouse liver cytochrome P-450 (P-450111AM1): its cDNA cloning and inducibility by dexamethasone," *Biochim. Biophys. Acta* 1130(3):329-332 (1992).

Geick A et al. "Nuclear receptor response elements mediate induction of intestinal MDR1 by rifampin." The Journal of Biological Chemistry 276(18):14581-7 [Epub](Jan. 31, 2001).

Quattrochi et al., "CYP3A regulation: from pharmacology to nuclear receptors," *Drug Metabolism and Disposition* 29(5):615-622, May 2001.

Montoliu L, Gene transfer strategies in animal transgenesis, Cloning and Stem Cells, 4(1):39-46 (Mar. 2002).

Houdebine LM "The methods to generate transgenic animals and to control transgene expression" J Biotechnology 98:145-160 (2002).

Genbank accession No. D28565.

Genbank accession No. AF280107.

Genbank Accession No. D11131.

Ristevski S, "Making Better Transgenic Models: Conditional, Temporal, and Spatial Approaches" Molecular Biotechnology, 29:153-164 (2005).

Smith K R, "Gene transfer in higher animals: theoretical considerations and key concepts", Journal of Biotechnology, 99(1):1-22 (Oct. 9, 2002).

Robertson G R et al. "Transgenic mouse models of human CYP3A4 gene regulation", Molecular Pharmacology, 64(1):42-50 (2003).

Hamzeiy H et al. "Mutation analysis of the human CYP3A4 gene 5' regulatory region: population screening using non-radioactive SSCP". Mutation Research. 500(1-2): 103-110 (Mar. 20, 2002).

Pascussi J M et al. "Evidence for the presence of a functional pregnane X receptor response element in the CYP3A7 promoter gene" Biochemical and Biophysical Research Communications 260(2):377-381. (1999).

Reid J M et al., "Rat and human liver cytochrome P-450 isoform metabolism of ecteinascidin 743 does not predict gender-dependent toxicity in humans," Clin. Cancer Res. 8(9):2952-2962, (Sep. 2002).

Martinez C et al., "Expression of paclitaxel-inactivating CYP3A activity in human colorectal cancer: implications for drug therapy," Br. J Cancer 87(6):681-686, (Sep. 2002).

Zhang W et al, "Differential regulation of the human CYP3A4 promoter in transgenic mice and rats." Drug Metabolism And Disposition, 32(2): 163-167 (Feb. 2004).

Herrmann J et al, "Comparative analysis of adenoviral transgene delivery via tail or portal vein into rat liver" Arch Virol, 149(8):1611-1617 (Aug. 2004).

Xie et al. "Reciprocal activation of Xenobiotic response genes by nuclear receptors SXR/PXR and CAR" *Genes and Development*, 14:3014-3023. (2000).

Ledirac et al. "Effects of macrolide antiobiotics on CYP3A expression in human and rat hepatocytes interspecies differences in response to Troleandomycin" *Drug Metabolism and Disposition* 28(12):1391-1393 (2000).

Pascussi et al. "Dexamethasone enhances constitutive androstane receptor expression in human hepatocytes : consequences on cytochrome P450 gene regulation" *Molecular Pharmacology*, 58(6):1441-1450 (2000).

Yanagida A et al. "A novel cis-acting DNA element required for a high level of inducible expression of the rat P-450c gene." *Mol Cell Biol*, 10(4):1470-1475 (1990).

Anderson, et al., "Quantitative Mass Spectrometric Multiple Reaction Monitoring Assays for Major Plasma Proteins," *Molecular & Cellular Proteomics*, (Dec. 6, 2005), 5(4):573-588.

Bertilsson, et al., "Functionally Conserved Xenobiotic Responsive Enhancer in Cytochrome P450 3A7," *Biochemical and Biophysical Research Communications*, (200 t), 280:139-144.

Cox, et al., "Multiple Reaction Monitoring as a Method for Identifying Protein Posttranslational Modifications," *Journal of Biomolecular Techniques*, (Jun. 2005), 16(2):83-90.

Jacobs, et al., "Utilizing Human Blood Plasma for Proteomic Biomarker Discovery," *Journal of Proteome Research*, (2005), A-M.

Unwin, et al., "Multiple Reaction Monitoring to Identify Sites of Protein Phosphorylation With High Sensitivity," *Molecular & Cellular Proteomics*, (May 27, 2005), 4(8):t134-1144.

Bertilsson, et al., "Functionally Conserved Xenobiotic Responsive Enhancer in Cytochrome P450 3A7," *Biochemical and Biophysical Research Communications*, (2001), 280:139-144.

\* cited by examiner

Fig 1. Human CYP3A4/*lacZ* transgene constructs
**-3 CYP3A4/*lacZ***
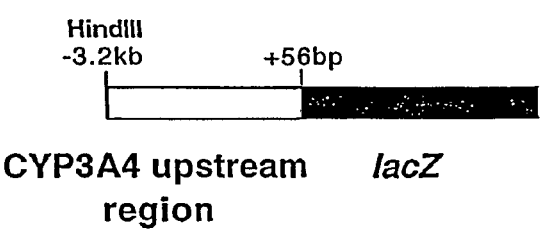
CYP3A4 upstream  *lacZ*
region
**-13 CYP3A4/l*acZ***
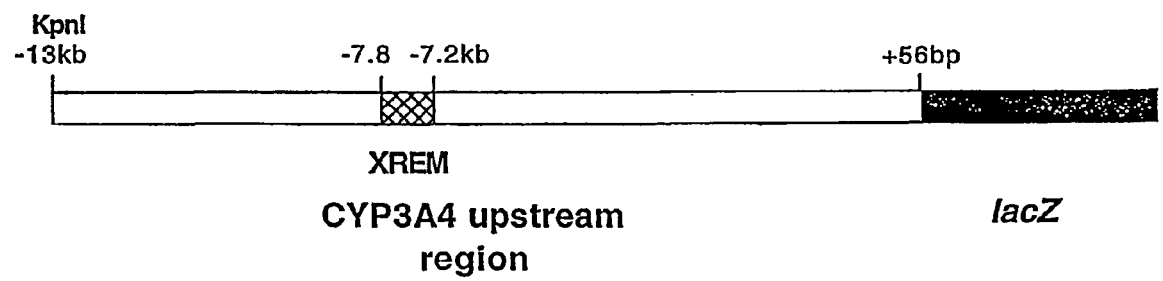
CYP3A4 upstream  *lacZ*
region

Figure 2. Xenobiotic induction of CYP3A4/lacZ transgene

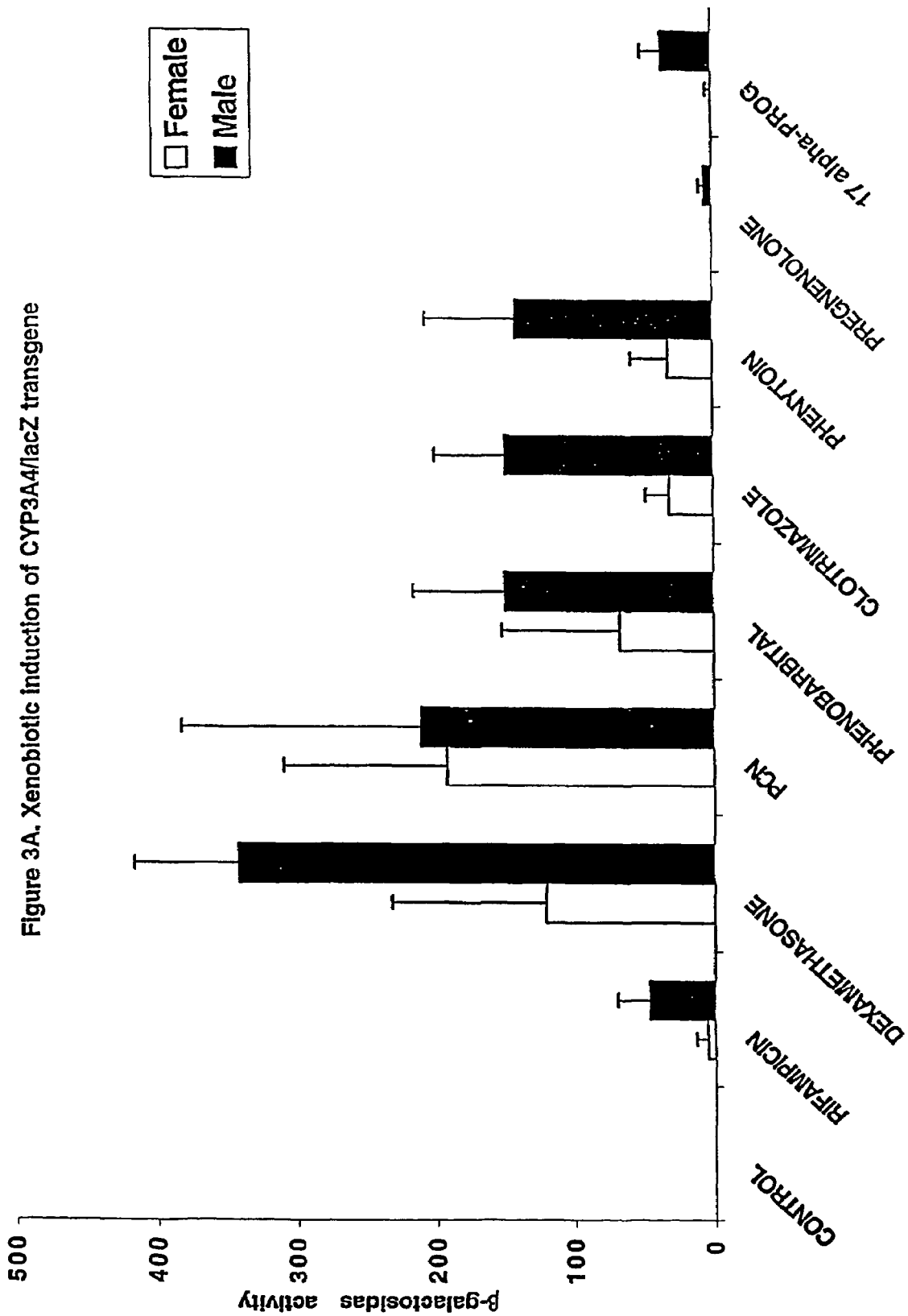

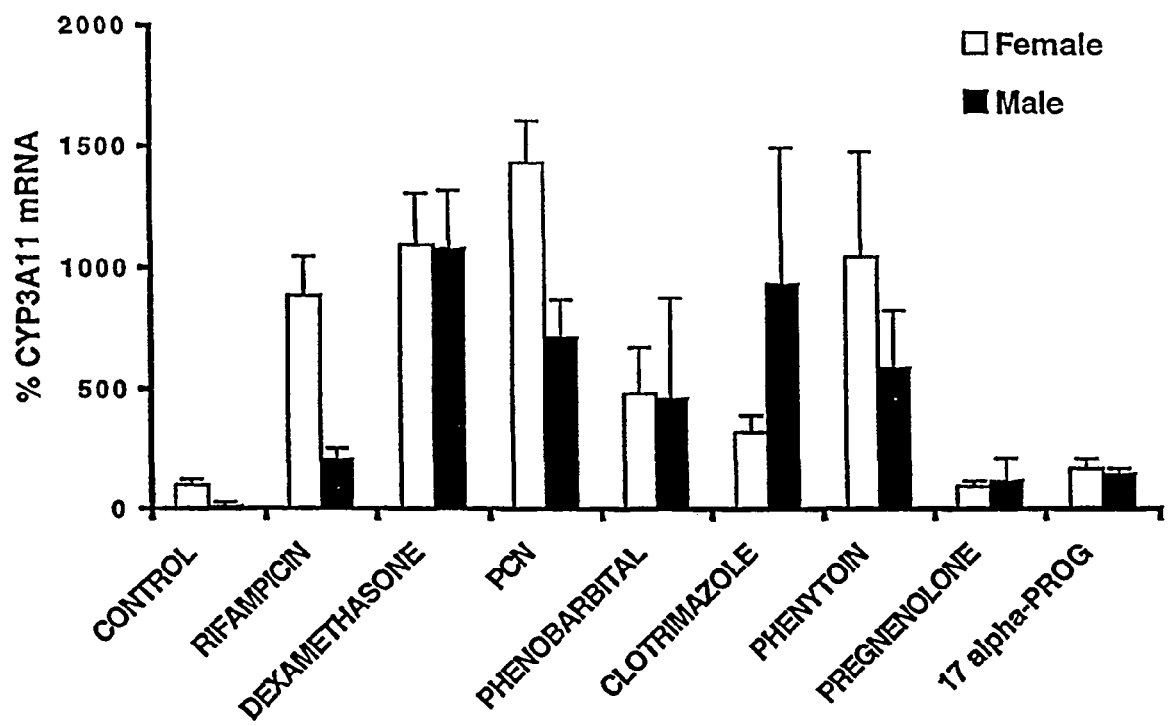

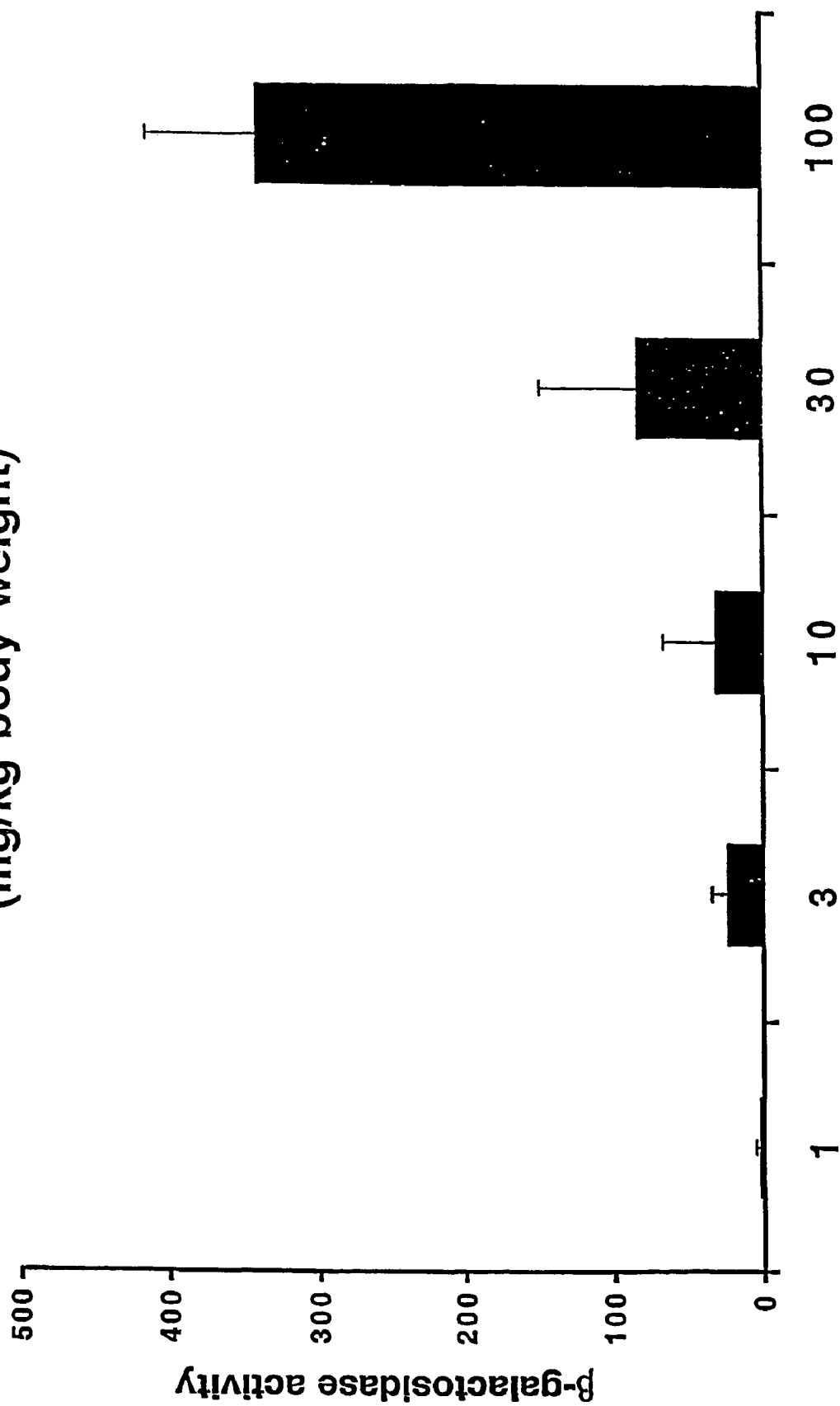

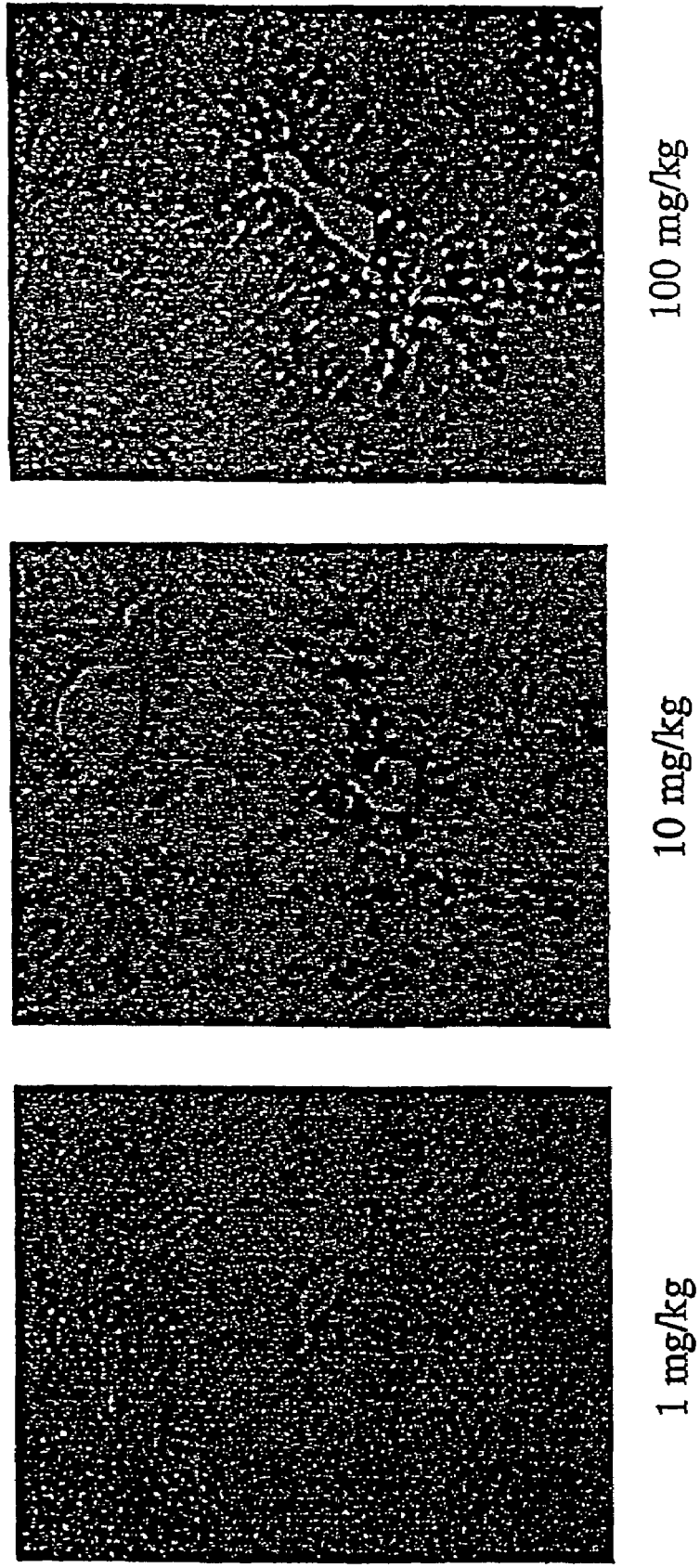
Figure 4B. Dose response of transgene expression

Figure 5.

CTGGTTCATCTCATTGGGACTGGTTGGACAAGAGGGTGCAGCCCACGGAGGGTGAGCCAAAGCAGGGTGGG
GCGTCGCCTCACCTGGGAAGCACAAGGGGTCGTGGAATTTTCTCCCCTACCCAAGGAAAGCCATAAGGGAC
TGAGCCTGAGGAACTGTGCACTCTGGCCCAGATACTGCACTTTTCCCATGGTCTTTGCAACCCGCAGACCA
GGAGATTCCCTCCGGTGCCTATGCCACCAGGGCCCTGGGTTTCAAGCACAAAACTGGGCAGCCATTTGGGC
AGACACCGAACTAGCTGCAGGAGTTTTTTTTTTTTTTTTCCATACCCCATTGGCACCTGGAACGCCAGTGA
GACAGAACCGTTCACTCCCCTGGAAAGGGGGCTGAAACCAGGGATCCAAGTGGTCTGGCTCGGTGGGCCCC
ACCCCCATGGAGCCCAGCAAACAAAGATTCACTTGGCTTGAAATTCTTGCTGCCAGCACAGCAGCAGTCTG
AGATTGACCTGGGACCCTCGAACTTGGTTGGGTGCTGTGGGGGGGCATCTTCCATTGCTGAGGCTTGAGTA
GGTGGTTTTACCTTCGCGGTGTAAACAAAGCTGCTGGGAAGTTTGAACTGGGTGGAGCTCACCACAGCTCA
GTAAGGCCACTGTGGCCAGACTGCCTCTCTGGATTTCTCCTCTCTGGGAAGGATATCTCTGAAAAAAAGGC
AGCAGCCCCAGTCAGGGACTTATAGATGAAACCCCCATCTCCCTGGGACAGAGCCCCTCGGGGAAGAGGTG
GCTTCCACCATTGTGGAAGACTGTGTGGCAATTCCTCACGGATTTAGAACTAGAGATACCATTTGACCCAG
CAATCCCATTACTGGGTGTATACCCATAGGATTATAAATCATTCTACTATAAAGACACATGCACACTTATG
TTTATTGTAACACTATTTACAATAGCAATGACCTGGAACCAATCCAAAAGCCCATCAATGATAGACTGAAT
AAAGAAAATGTGGCACATATACACTGTGGAATACTATGCAGCCATAAAAAAGGATGAGTTCATGTCCTTTG
CAGAGACATGGATGAAGCTGGAAACCATCATTCTCAGCAAACTAGCACAATAACAGAAAACCAAACACTGC
ATGTTGTCACTCATAAGTGGGAGTTAAACAATGAGAACACATGGACACAGGGAGGGGAACGTCACACACTG
GGGCATGTCGGGGAGTGGGGGCCTACGGGAGGGATAGCATTAGCAGAAATACCTAATGTAGGTGACGGGTT
GATGGGTGCAGCAAACCACCATGGCACATATACACCTATGTAATAAAACTGCACGTTCTGCACATGTACCC
CAGAACTTAAAGTATAATTAATAATAATAATAATTTCTGGGCATGTAAGTAGCTGTCTTTCAGGTTCTACT
TTGATACATATTCTGAGAGAATTAAACCTGTCAAAGAAACCTTGACTTTCAATGGCAGGCACTGGAATTGA
CCCTAATAATGTGTTTTGGGGTAAGCCTACTCATATTCTCAACCTGTCTGCAGTAGTCGTTAGAATCTGAA
CTTCCTGAAGTTCATGTGCAAAGTTGAGTTAATTGTTTAATATTCAACAAGGATTATGCCAGTAAGATGGT
AGGAAAATATTAGATATGTGTCATCACTGCTGGTATTATTTAAACTGCAACATATTTTAGCTGGCTGCTGA
TCTCAGCCACCATGCCTGCATTTTATCTCTGTCTCGTGGTCTGCAACCTTGGAAGCTTTGAACTTAGCTCA
TAGAATCCTGGGCATCAAGAACATGTGGTTCTAATGGCTAGATAGGGAATGAGAGTAAAAGGATTTTGCCC
ACGGTCACGTGAGTAAACAACAGATTTGGAGGGGTCTGGACTACTGTGATGACTTCATTCTGACAATATGT
TCCAGTTGTCCTTTCATTTCCTCCTAATCACATGTCTGGTCTGATCTGGCTGTTTCCCACCTTCCAATTCC
TGCCTTCTCCAATGCTCCCTTCCGTAGGTCACTCTGTGGCTCAGAGACCCTGCTTAGCAAGCGCCCAACCT
TTCAATTATTTGTTCAGTAAAACTTGAACTCATGTCTCCCCTTCTTGATAAAAAGAAAATACGTTATGTAA
TGTCGGGTTACTCTATAACTCTTGTCCTGTCTCTCGGCAACTACTGAACTAACTGTTTTCATATTGAGCAA
ACGTTTATGGAAGGACTGCCAAGAGTCAGGTACTAGGCTTGGTAATATTCCCCGTTCTCTCTAGTCAAAGC
CAACACCAGCCAGACTTGCAGATCTAGGTCCCAAGCCCACTGCAGATCACAGGCCAGGGTCTGGTCTCCTC
TGAGCTCCTTTGGGAGGGAAAGACAGAATTATTAACACCCATTTTGTAGATTAGGCAACTGAGGCTGAGGA
AGTTTAAATAACTCAGACAGGGCCTGCACGTCAGTCATATTCCAAGGATCCCTACTCACTGTCTTCTCTCT
ACAGAACGAGATGTCTCTGGAGTCCATAGAAAGCCCAGGAGCCTGGCTGGGCACGGTGGCTCCTGCCTGTA
ATCCCAGCACTTTGGGAGGCCGAGGCAGGCAGATCACCTGAGCTCAGGAGTTCAAGACCAGCCTGGGCAAC
ATGGCAAAACCCCATCTCTACTAAAAATACAAAAAATTAGCTGGGCGTGGTGGTGCATGCCTCTAATCCCA

Figure 5 continued

```
    GCTACTTGGGAGGCTGAGGCACAAGAATTGCTTGAGCCCAGGAGGCAGCAGTTGCAGTGAGCTGAGATTGT
    GCCAGTGCACTCCAGCCTGGGCAACAGAGCAAGATTCCATTTCAAAAACAAAAACAAACACAAACAAACAA
    ACAAAAATAGAAAGCCCAGGGACCACCTGCGTCAGGTTCCCAGCCACACCTTTTTCTTGTCCTCCTCTGTC
    TCTGGCATCTTCTCACAGGTTCCTAATTGTTTGTGGTTGCACAAATTCAAAATCCAGAAAAATTACCACT
5   TCACACCCACTCAGATGGCTATTTTTTTTTTGAAGGAAGATAACAAGTGTTGACAAGAACATGGAGAAATT
    GGAATTCTCACCCATTGCTGGTGAGAATGTAATACGGTGCTGCTGCTATGGAAAACAGCTTGGAGTTTCCT
    CAAAAAGTTCAACAGAATTTCAATGTGACCCAGCAATTCCCCTCTAAGTTATAGATCTGAGAGGATTAAAA
    ACAGTTACTAAAATACACGGACTCACATATTTCTAACAGTCCAATTCACAAGGGCCAAAAGGTGCTAATAG
    CCCACATGTCCATCGATGGATGGATAAATAAATTGTGGTCTATCCATACAATGGAATATTATTCGGCCATA
10  AATGGAATGAAGTACTGACGCATGCTACAGAATGGATGAACCGCAAAAAAAATGGATGAACACATGCTACA
    GAATGGATAGCCTCACTTTACTATGAAGTGAAGGCCAGAAACGAAGTCCATATATTGCATCATACAAAATA
    TCCAGAAGAGGGAAGCCCACAGAGACAGAATGTGCAATGGTGGATGCCAGGGTCTGGGGAGAGGGAGAGT
    GGGGAGAAACTGCTCAACTGGTACAGGCTTTATTTTGGAATGATGGGAACATTTTGCAACTAGATAGAGGT
    AGTGATTGCAGAACACAGAATGTACTGAATTCCACTGATTTTTTTCACCTTAAAATGGTTAATTTTCAGTC
15  CTGAGATTGGATAATCATAAAAAAATGGTTAAPTTTATGTTATGTGAATTTCATCCCTATACATATTTTAA
    ACCTCAGAAATATACACTAGCAGGCATGGAACAGGTCACTGTGGTGCCTGCCAAGCCCGGTGATGTTATCT
    GGGGTCCCCGGCCAGCCTTAAGCCTCTTGCTGACCGGTGGAGGGCAGAACCTTTGCCCTAAAAGTATAATA
    TCCACATGCTGGCATGATTCCTGGCCAGATGGCTTCTTTATTAGCAGTAATTGAAACTGCCTCGATACAGA
    CACTGTACCTTGCAACCAAAAAATGACTCAACAATGATAATAAGGGTTAAGCTGGGCCTTTCTCTCTTTGC
20  CAGTTAAATTATATTTATTATAGCTTGACATGAAAAACAAAGCAACTCCAACAGGTATCACAAGGGCAAAG
    GACATGAACATTTTATCAAAGAAGAAATGCAGCTGTCAAAAATACAGAAATATTCAACCTTGTTCATAATA
    AAGTGGCTGGGCTCAGTGGTTCATGCCTGTAATCCCAGTGCTTTGCAAGGCTGAGACAGGAGGATCATTTG
    AAGCCAGAAGTTCAAGACCATCCTAGGCAAGTCAGTTCAATACCAGACTTCATGTCTACAAAACATCAAAA
    AATTAGCCAGGCATGGTGATGCATGCCTGTTGTCCCAGCTACTCAGGAGGCTGAGGCAGGAGAATTGCTTG
25  AGCCTGGGAGGCTGCGGTGGCGGTGAGCCATGATTGTGCCATTGTACTCCAGCCTGGGCAATGCAGCAAGA
    CTGTCTAAATAACAAAAATAATAGTAAAGAAAAGGATTGGGATGCCATTTACTTGCGTATTCAATACACAG
    AGTTAAAAGTAATTTCTACGTTTTCTATTTTTTTATTACTAAAAAAAGCTGGACCATTCTCACAGCCTGAA
    ATGCTTCTCACTTTCCCTTCTTCTGTCCAAACACTTCTCTATGATAATGCAAACAGTCACTCCTTTAGGAA
    GACTTCACCCCAGGTAGTTCCAGATCCCCTTATCTCTGCCTTCCCAGAACTCCTGGTGTCTCTCCAGTTCC
30  CTCCGTGTGGTGAAGTACCCTACCTAGGGTTTCAGTATGGCTCTGTCTGCAAAGGTCTTGTTCACACCTTC
    CCTTATGGTTCTGTTGCCCTGTGTTGTGTCATAGCACAGGGCACAGTGGAGAACCCATTCACACTGATAGA
    GAGGGCCCCATGGTCCTGGAGATAACCATGTAACCGATCAGAATAAGGCATTGAGGGCTGGGTGTCAGGCG
    TGGGCTGCACTTGGGTGGGCAGGTCCCTGGAAAGTCACTGGGTTTGGCAAGCTTCCTAGTAACATGTCTC
    TCTGGGGTCCCCCTTGGAACTTCATGCAAAAATGCTGGTTGCTGGTTTATTCTAGAGAGATGGTTCATTCC
35  TTTCATTTGATTATCAAAGAAACTCATGTCCCAATTAAAGGTCATAAAGCCCAGTTTGTAAACTGAGATGA
    TCTCAGCTGAATGAACTTGCTGACCCTCTGCTTTCCTCCAGCCTCTCGGTGCCCTTGAAATCATGTCGGTT
    CAAGCAGCCTCATGAGGCATTACAAAGTTTAATTATTTCAGTGATTATTAAACCTTGTCCTGTGTTGACCC
    CAGGTGAATCACAAGCTGAACTTCTGACAAGAACAAGCTATCATATTCTTTTCAATTACAGAAAAAAGTAA
    GTTAATTGATAGGATTTTTTTTGTTTAAAAAAAATGTTACTAGTTTTGAAAAGGTAATATGTGCACATGGT
40  AAACACTAAGAAGGTATAAGAGCATAATGCTTTTATACTACTAAGAATAATGTTTTCTCTAAGTTTTTTTT
```

Figure 5 continued

```
    GGTAGATGCTTTCATCAGATTAAGAAAATTCCCTGCTATTAGTTGTTGAAGGTTTTTATATCATAAATGAA
    AGTTGAATATTATTATCATATATTATTAATATATTGTTATTGAACTATCAAAGCCTTTTCCTAAAACCATT
    GAGATGATCTTATAACCATTCTCCTTTAACCTGTTGACGAGATCATTGGTATTTATACTATTTCTCTGTTA
    ACCATTCTTGAGTCTCAGGTTTAAATTCAACTTGGTCATGGTGTGTCATCTTTGATCATTGCTGTCTGTGG
 5  CTTGCTACTGTTTTGTTTAGGATTTTTGCACTGATGCTCATCAATGAGACTGGCATGCCATCTTCCTTTGC
    AGTCCTGATTTTTTTCTGATTTGGATCATGTGGTTATGGCCCTCATGGAATGAGTTGGGCATGATGCCTTT
    TTTTCATGTCTCTGGATTGATGGGACACTTTGGATTCTCTCCAGATGGCCCTCAATGGTCCCTGCCTCCTC
    ATTGTTAGGCCCCTGGGCAAGCCCTTCTCATTTCTGGTAGGCCCAGGAACCTGTGGGGGTTTTGTTTGTTT
    GTTTGTTTCTTGAGTCGGAGTCTCACTCTGTCACCCAGGCTGGAGTTGGAGTGCAATGGCCCGATCTTGGC
10  TCACTGCAACCTCCACCTCCCAGATTCAAGCAATTCTCCTGCCTCAGCCTCCTGAGTAGCTGGAATTACAG
    GCACCCACCGACACACCCTGCTAATTTTTGTATTTTTAGTACAGATGGGGTTTCACAATATTGGCCAAGCT
    GGTCTCGAACTCCTGATCTCATGATCTGCCCGGCTTGGCCTCCCAAAGTGTTGAGATTACAAGCATGAGCC
    ACCACACCCAGTGAACCTGTGGTTTTTAGAAGCTCCCCATGCATGTGAATGCTGTGAGCATCCCAGGATGA
    CAGCCACTGTGTGTTCAGCTGTTGGAACTGTGAGAAAGCACCAGTGGGACCTTCTCCAGCACCTGCCTGCT
15  GAGTTCATGGAAGAGGCTTGTTGGGGAGATGATGCCCTGGCTGACTCCTGAAGGATGGTTAGGAATGCACC
    AGATGGAAGCTGGGTTGGACCCACTCTATGCTGAAGAACAGCTTGTGTGGACACAAGGAGACACGGATATG
    TCATTTTTGTAGAGCCTGAGGAGTGTCCAATCACACCATTTGCTTAAAACATCATGCACACTTGGAAAAGT
    GGACTGAGACCGAATGAAGAAGCTAACAGTGGCCAGATCAGAAAGGGTCTTGTGTTACTTCCTAGAGATAC
    TTAGATTTTATCCTGTGGGTGATAGGAGCAGTTGGAGGGACTGAAGACAAGGAAAGAAACATGTTTCAAGA
20  TCTATGTTTTTCAAGACGCTTTTCTGGTGGCTGAGTAGGGAATTCCCTGGATAAGTCCTGCCCAGGGTCAG
    GCAAAACAAGTTAGGGGGTTACTGAAATAAGGAGTATGAGAAATGGTGTAGGTTGTGCTGACGTTTTGTAA
    CACATCTCATGATGATCTTCATTTCCTTCACTAATTTCCTGTTTCATTAATTCCCTTCCACGTGCTCTTCT
    GAAATTTGCCTCACATTCTCTGATTTCTCTTTTACCTGTTGGTTTCATCACCTTTTACTTTTTGCTTTCCT
    GGAAACACAAATGATTCTGATTGTGACATGTCAGAATTATTTGCAACATTTGCCTTTCTGCTGAAACCATG
25  AGTTCACTGAATACACAATTTAGTAAAGTGTAGGATGCACATGTCGTTTTCGTGGTCACAACCAGCTCTGT
    AGCATTTTATAACTACACTGGCAGTGTGCTGGGAGGTGTAGAGAGAAATATTTATCACATGTGTGGCTGAC
    ACAACCTGCCAAGTTATTTTAGGAGCCTCCTTGGAATCCCAGCAAGAATGCTACCGGCACAATTTGTAATC
    ACAGCATCCTGCTCCATGCCTTGGCTTCATGGCATAGTCACTTCTGCAAGTCTCTTTCCAGCTGTCTGTTC
    CCATGTCTATAAAGTATGAGTTAAATCATCCTAACACTACTCATCTTACAAAGTTTTCTTGCTGATGTTAA
30  GAGAGTTGGGAAAGAACTGTATAAACTGTGAAGTGCCATGGAGATGTTAGTGGTTACTTTATCAAGAAATA
    GACACTCTAGAATGGAGTAGAAAGCCAACAGTTATGATTGAGTCCTCCTCCTCTTCTTCTTTTTATTAATT
    TATAAAGAAAAGAGGTTTAATTGACTCACAGTTCCATATGGCTGGGGAGGCCTCGGGAAACTCTCAGTCAT
    AGCAGGAGGCAAAGGGGAAGAAGGCACCTTCTTCACAAGGCGGCAGGAGAGAGAGAGCTCCTGTTCTTTTT
    TGTCATAAAGTCTACAGAAGTGCTTATACTTCAGGACAAGGGCAGGCAGAGAGAAGGAAGGACATTGCTTC
35  ACCCCAGCCCTCACTGACGAGTTTGCTAGGGACCTCACTTTGTCCCAGAGTAGGGCAGAACTCTGGCCAC
    TACCCATTCAGAAGGCCTGGGCTGCACTGCTAGTTCCTCACTAACTCTGTGTGGCCTTGGGCAAGGTTGGG
    CCTGTGTTAACAGATTATGACCCTGGGCTCTCAAGCTAGAGGATCTAAATTTGAATCCTGGCTCTGCTAAA
    GCAATTAGTGATGTAAACTTTAATGGGTCAGTTAACCTTCCTGTGGCTTAGTTTGCTCATCTGTAAAATAG
    GGATCATAACAGTATCAATACCACATGATTGTTGGACAGATTGAATCAGTTAATGCAGGGGAAGTACTTAG
40  CATGACACGTATTCACTATCATTTCCTGGAGTAAGAGCTGTGTGTGAGTGGGTGTGAGCATGTGTGAAACC
```

Figure 5 continued

```
    TTTTCTCTGCAATCTCAGTTAAGAAACCAATCCAGAATTTAAAGTTCAGGGCCTAAATGGGTGGTTATCTT
    CTCCCAGTTCCATCCTATCCCACCTTTGCTCTTCCTCCCGCCCACAGGAGCTGTTGGTCCTTGATTGGGCT
    GGAAGACCTGGTGGACCCTAAGTGATCTATAAGAGGAGAATAGAGAACAGGGAATGTCTTCAAAAATCTAG
    AGGGACACAGAGGCTGAGAGGCAGGCAGTCCTGCAGGGTCTTCTGATTGGGACAAGGAGAACCTTGGTCTT
 5  CACAGGCCAATTCTGGTCAGTTTCCCCCATGGACAGATGAGGAAACAGGCCCAGGAATATCCAAGGTCTCA
    CACTTCCCATCTGTCAAGTCTTGTTGATTCTGTTGTATTCATGTCTCTCAAAGGGAGATAGAGTTTAGGGA
    AGAAAGAAGGATCAACTGTGTCTGATACCACTGGGAGCTTAAGTAAAGGGTTCTTTTACTTCATAGCATTT
    ATCCCAATTTGTAATTCAGTATTATTTGTGTGGCTGTTTGGTGTCTCTTTCTCCTATATGAGTGCTAGCTT
    CATAAGGGCAAGGATTTTGATTCTTTAATATTTAGTGCTTGCCACATGCCCTGAACACAGCAGGCATACAG
10  GCTAACCAACATACAGTGGCATGAAAGTCATGAAAGTGAGACACCTACCTCCTCCAGTGCCAAGAGAGCAT
    AACCATGCACCTGTCACTCTCCTCAACACCACCCCCAAGCATGAGGCCCAAAAGCATTAGCTAATCCCCTC
    CTCCAGCCACTAAAACTTAAAGGCCAGGTGTGGTGGCTCCCATCTGAAATCCCAGAACTTCAGGAGACAGC
    AGCAGGAGGATCACTTGAGGCCAGGAGTTTGAGATCAGCCTGGGCAACATAGCTAGGTCCCATCTGTACTA
    AAAATTAGCTGGGCGTTGTTGCATGCCTGTAGTCCCAGCTACTAAGGAGGCTGAGGTGGGAGGATCACTTG
15  AGCCCAGGAGGTGGAAACAACAGTAAGCTATAATCACAGCACTGAACTCTAGCCTGGGCAACAGAGTGACA
    CCCTGCCTCAAAACAATTTTAAAAATAAATAAGAGCAAAACTTAGATACCACGTGGTCACCCCAACATGCA
    AAATCAAGTTTTCCCCTACTGAGAAGAATGGGACTTGACAGCTGAGTTACAGAGAGATAATCTTCTTCTT
    CTTTTTTTTTTTTTGGTTTACATCCTCAAGATCATGACTTGTGAAATTTGAATCGAATACACATGTAATTC
    CAGAGCAATGTTGCCTCCGCATACCATCAGCAATTCACTTGGCTACTGGAAGTCAGGATAAGCTTCCCAGA
20  AGAGAGGTACCACTTGGGCTACCAATATAAAAGGATGAAAATATCAGAGTGATGGTGTTCTTTACAACGTT
    GAGTCCCTGGACAGCCTGTCCACTGATGCTGATATCTGAGCCTAATGCTTCTCTGAATGTTGAGATTGAAC
    TTTGATCCAATGAAACTAGAACGAGAAAGAAGATAAGTCTTTCATTGTTGATAAGGACATTATGTTTCTCA
    TACTTGTATGATTATTTTTCCTTAGCTGTACTATAATTATCTGCTTATTTGTCTCTGCTCTATGTGCTTAG
    GGTACAAAGTTGACCAAGACCAACTTTGGTTGGAAGCATAGTACTAAGAGCACAGTACTGAGAGCACAGTA
25  TTGAGAGCACAGCTTTAAAAAACATGATGAAGGCTTTAATACAGGAAATGAGCAGGGGAGAGGCATGTGGT
    GGTTGGATGTATCTTCCTTGACACAGTCAGTGCAGCTCTCAGTAGTCAAGTCCCTACATGTTAGAAGATGT
    TACCTTCTGTGGAATTAAGTGGCAGAACTTGCCTTCAATTATTTTCCTTTGCAGAACAACACCAACTGCAT
    TAGTTAGGACACAGTGCTGGCTGCATTTAAGTCCCAAGCGATGATTAGTCTCTCACTGTTGGTATAGATTC
    AAACCAATCAGACCACCTCCTAAAGTTTGTAGGGCAGGTAAATCCTCATCTTAGAATAAAAATCATCTTAC
30  CAAGTATGTGTTTAGAGGCAAGAAGAAAACATATTTGTTTCTGTAAGAGTTTTGTTTAAAAAAAATATAA
    GAAAGGCTCTCGGTTTAGGTGAGGTAATGAAGTTGTTGATAGTTATCAGATGACACTGGAATCTTTACTTC
    TCTGAACGTGTTCTGTGCATCTCTCAGTGTGGGAACATAGAGAGGGAGATCCTCCAGCAATGCCACTGATA
    TGGTCAGAAACTGCATCTTTCTTTCTCCCTGCTGAGATGAGATGGAGTCCTTTGTTCTAGAAGACCCATGG
    TGGTGCCGCTGGGAGTAACCCTTGAGACAGGAACACAAATCCCAACCAATTTGTGGTTGCAGCCTTGAGTC
35  TCACTATTTCCCATAGTGATGCGTAGCAGGGAATGGCAGGTGCACCAGAGCAGGAGAGGACCTAATATCTC
    CCTTCCTGTTAGCTTTTTATAAAGTTTTATTGTGATCAGTAGCAGTTGGGAAGCTACTTGCAGTCACTGAG
    CCTCAGTTTCTACATCTGTAAACTGGGGATAGTAGCATGGCCCCTACTTAATGTGCTCAGCAAAGCCACTG
    AAAGGAGACAGAAATGTATCTAAATTACCCTGGACTTTTATCCTAGCTCTCTTGGGGATTGTCACCACCTT
    CCCATGTTTGTCCTTTTTGGTTTGATGCTTGCTGTCACTTCTTTCCTTAGGTGCCTCTCTGTACGGCTCTT
40  TTATCCCAGGGATTCCAGAGTTACAGCACATGCATACCACCATCCAAGCATGTTTATTTGTCTCCTGCTTC
```

Figure 5 continued

```
ACTAGGCTGTCCCCAAGGAACATGTGGCTCCCGGCACACACCTGGCACAACACTGCACATGACATTCACCC
ACTTGGCCTTGAATCTGACAAGGAATCTGGCATGATGTTCACCCACTCAGGCCAGGTGCCGAGCAGCCCTG
GAGGCTTAGGGGCCAGAGGGATGGGAAAAGGTGTCTTTCTGGGGTGAGTATCAGTTTCTGCAGGAGGGCTG
AATGTGAGAAAGAATAAAGAGAGAAGGAAGCGAACAAGCACAGCTTAAACATCGCCTATTTCTATTGAGTT
TTAAGAACGCTGTGATTTTGTTTGTCATGCAATCCATTCATCAGGCCAGGCAGACACAGAACTTGGGTGTG
AGTGACGATAATGAGCTGATATAATTTTCACACCCTCATCACTGAGATCTCTCCCATCAGGAATGGGTCAG
GGAGCTCACAGGTGGCAGCAACTGCTATTACAGGCCTCATCTCTACCAGCTCCTGGGGCCTGCCCTCCTCC
CATTAGAAAATCCTCCACTTGTCAAAAAGGAAGCCATTTGCTTTGAACTCCAATTCCACCCCCAAGAGGCT
GGGACCATCTTACTGGAGTCCTTGATGCTGTGTGACCTGCAGTGACCACTGCCCATCATTGCTGGCTGAG
GTGGTTGGGGTCCATCTGGCTATCTGGGCAGCTGTTCTCTTCTCTCCTTTCTCTCCTGTTTCCAGACATGC
AGTATTTCCAGAGAGAAGGGGCCACTCTTTGGCAAAGAACCTGTCTAACTTGCTATCTATGGCAGGACCTT
TGAAGGGTTCACAGGAAGCAGCACAAATTGATACTATTCCACCAAGCCATCAGCTCCATCTCATCCATGCC
CTGTCTCTCCTTTAGGGGTCCCCTTGCCAACAGAATCACAGAGGACCAGCCTGAAAGTGCAGAGACAGCAG
CTGAGGCACAGCCAAGAGCTCTGGCTGTATTAATGACCTAAGAAGTCACCAGAAAGTCAGAAGGGATGACA
TGCAGAGGCCCAGCAATCTCAGCTAAGTCAACTCCACCAGCCTTTCTAGTTGCCCACTGTGTGTACAGCAC
CCTGGTAGGGACCAGAGCCATGACAGGGAATAAGACTAGACTATGCCCTTGAGGAGCTCACCTCTGTTCAG
GGAAACAGGCGTGGAAACACAATGGTGGTAAAGAGGAAAGAGGACAATAGGATTGCATGAAGGGGATGGAA
GGTGCCCAGGGGAGGAAATGGTTACATCTGTGTGAGGAGTTTGGTGAGGAAAGACTCTAAGAGAAGGCTCT
GTCTGTCTGGGTTTGGAAGGATGTGTAGGAGTCTTCTAGGGGGCACAGGCACACTCCAGGCATAGGTAAAG
ATCTGTAGGTGTGGCTTGTTGGGATGAATTTCAAGTATTTTGGAATGAGGACAGCCATAGAGACAAGGGCA
AGAGAGAGGCGATTTAATAGATTTTATGCCAATGGCTCCACTTGAGTTTCTGATAAGAACCCAGAACCCTT
GGACTCCCCAGTAACATTGATTGAGTTGTTTATGATACCTCATAGAATATGAACTCAAAGGAGGTCAGTGA
GTGGTGTGTGTGTGATTCTTTGCCAACTTCCAAGGTGGAGAAGCCTCTTCCAACTGCAGGCAGAGCACAGG
TGGCCCTGCTACTGGCTGCAGCTCCAGCCCTGCCTCCTTCTCTAGCATATAAACAATCCAACAGCCTCACT
GAATCACTGCTGTGCAGGGCAGGAAAGCTCCATGCACATAGCCCAGCAAAGAGCAACACAG
```

Figure 6.

```
CTGGTTCATCTCATTGGGACTGGTTGGACAAGAGGGTGCAGCCCACGGAGGGTGAGCCAAAGCAGGGTGGG
GCGTCGCCTCACCTGGGAAGCACAAGGGGTCGTGGAATTTTCTCCCCTACCCAAGGAAAGCCATAAGGGAC
TGAGCCTGAGGAACTGTGCACTCTGGCCCAGATACTGCACTTTTCCCATGGTCTTTGCAACCCGCAGACCA
GGAGATTCCCTCCGGTGCCTATGCCACCAGGGCCCTGGGTTTCAAGCACAAAACTGGGCAGCCATTTGGGC
AGACACCGAACTAGCTGCAGGAGTTTTTTTTTTTTTTCCATACCCCATTGGCACCTGGAACGCCAGTGA
GACAGAACCGTTCACTCCCCTGGAAAGGGGGCTGAAACCAGGGATCCAAGTGGTCTGGCTCGGTGGGCCCC
ACCCCCATGGAGCCCAGCAAACAAAGATTCACTTGGCTTGAAATTCTTGCTGCCAGCACAGCAGCAGTCTG
AGATTGACCTGGGACCCTCGAACTTGGTTGGGTGCTGTGGGGGGGCATCTTCCATTGCTGAGGCTTGAGTA
GGTGGTTTTACCTTCGCGGTGTAAACAAAGCTGCTGGGAAGTTTGAACTGGGTGGAGCTCACCACAGCTCA
GTAAGGCCACTGTGGCCAGACTGCCTCTCTGGATTTCTCCTCTCTGGGAAGGATATCTCTGAAAAAAAGGC
AGCAGCCCCAGTCAGGGACTTATAGATGAAACCCCCATCTCCCTGGGACAGAGCCCCTCGGGGAAGAGGTG
GCTTCCACCATTGTGGAAGACTGTGTGGCAATTCCTCACGGATTTAGAACTAGAGATACCATTTGACCCAG
CAATCCCATTACTGGGTGTATACCCATAGGATTATAAATCATTCTACTATAAAGACACATGCACACTTATG
TTTATTGTAACACTATTTACAATAGCAATGACCTGGAACCAATCCAAAAGCCCATCAATGATAGACTGAAT
AAAGAAAATGTGGCACATATACACTGTGGAATACTATGCAGCCATAAAAAAGGATGAGTTCATGTCCTTTG
CAGAGACATGGATGAAGCTGGAAACCATCATTCTCAGCAAACTAGCACAATAACAGAAAACCAAACACTGC
ATGTTGTCACTCATAAGTGGGAGTTAAACAATGAGAACACATGGACACAGGGAGGGGAACGTCACACACTG
GGGCATGTCGGGGAGTGGGGGCCTACGGGAGGGATAGCATTAGCAGAAATACCTAATGTAGGTGACGGGTT
GATGGGTGCAGCAAACCACCATGGCACATATACACCTATGTAATAAAACTGCACGTTCTGCACATGTACCC
CAGAACTTAAAGTATAATTAATAATAATAATAATTTCTGGGCATGTAAGTAGCTGTCTTTCAGGTTCTACT
TTGATACATATTCTGAGAGAATTAAACCTGTCAAAGAAACCTTGACTTTCAATGGCAGGCACTGGAATTGA
CCCTAATAATGTGTTTTGGGGTAAGCCTACTCATATTCTCAACCTGTCTGCAGTAGTCGTTAGAATCTGAA
CTTCCTGAAGTTCATGTGCAAAGTTGAGTTAATTGTTTAATATTCAACAAGGATTATGCCAGTAAGATGGT
AGGAAAATATTAGATATGTGTCATCACTGCTGGTATTATTTAAACTGCAACATATTTTAGCTGGCTGCTGA
TCTCAGCCACCATGCCTGCATTTTATCTCTGTCTCGTGGTCTGCAACCTTGGAAGCTTTGAACTTAGCTCA
TAGAATCCTGGGCATCAAGAACATGTGGTTCTAATGGCTAGATAGGGAATGAGAGTAAAAGGATTTTGCCC
ACGGTCACGTGAGTAAACAACAGATTTGGAGGGGTCTGGACTACTGTGATGACTTCATTCTGACAATATGT
TCCAGTTGTCCTTTCATTTCCTCCTAATCACATGTCTGGTCTGATCTGGCTGTTTCCCACCTTCCAATTCC
TGCCTTCTCCAATGCTCCCTTCCGTAGGTCACTCTGTGGCTCAGAGACCCTGCTTAGCAAGCGCCCAACCT
TTCAATTATTTGTTCAGTAAAACTTGAACTCATGTCTCCCCTTCTTGATAAAAAGAAAATACGTTATGTAA
TGTCGGGTTACTCTATAACTCTTGTCCTGTCTCTCGGCAACTACTGAACTAACTGTTTTCATATTGAGCAA
ACGTTTATGGAAGGACTGCCAAGAGTCAGGTACTAGGCTTGGTAATATTCCCCGTTCTCTCTAGTCAAAGC
CAACACCAGCCAGACTTGCAGATCTAGGTCCCAAGCCCACTGCAGATCACAGGCCAGGGTCTGGTCTCCTC
TGAGCTCCTTTGGGAGGGAAAGACAGAATTATTAACACCCATTTTGTAGATTAGGCAACTGAGGCTGAGGA
AGTTTAAATAACTCAGACAGGGCCTGCACGTCAGTCATATTCCAAGGATCCCTACTCACTGTCTTCTCTCT
ACAGAACGAGATGTCTCTGGAGTCCATAGAAAGCCCAGGAGCCTGGCTGGGCACGGTGGCTCCTGCCTGTA
ATCCCAGCACTTTGGGAGGCCGAGGCAGGCAGATCACCTGAGCTCAGGAGTTCAAGACCAGCCTGGGCAAC
ATGGCAAAACCCCATCTCTACTAAAAATACAAAAAATTAGCTGGGCGTGGTGGTGCATGCCTCTAATCCCA
GCTACTTGGGAGGCTGAGGCACAAGAATTGCTTGAGCCCAGGAGGCAGCAGTTGCAGTGAGCTGAGATTGT
```

Figure 6 continued

```
GCCAGTGCACTCCAGCCTGGGCAACAGAGCAAGATTCCATTTCAAAAACAAAAACAAACACAAACAAACAA
ACAAAAATAGAAAGCCCAGGGACCACCTGCGTCAGGTTCCCAGCCACACCTTTTTCTTGTCCTCCTCTGTC
TCTGGCATCTTCTCACAGGTTCCTAATTGTTTGTGGTTGCACAAATTCAAAATCCCAGAAAAATTACCACT
TCACACCCACTCAGATGGCTATTTTTTTTTTGAAGGAAGATAACAAGTGTTGACAAGAACATGGAGAAATT
GGAATTCTCACCCATTGCTGGTGAGAATGTAATACGGTGCTGCTGCTATGGAAAACAGCTTGGAGTTTCCT
CAAAAAGTTCAACAGAATTTCAATGTGACCCAGCAATTCCCCTCTAAGTTATAGATCTGAGAGGATTAAAA
ACAGTTACTAAAATACACGGACTCACATATTTCTAACAGTCCAATTCACAAGGGCCAAAAGGTGCTAATAG
CCCACATGTCCATCGATGGATGGATAAATAAATTGTGGTCTATCCATACAATGGAATATTATTCGGCCATA
AATGGAATGAAGTACTGACGCATGCTACAGAATGGATGAACCGCAAAAAAAATGGATGAACACATGCTACA
GAATGGATAGCCTCACTTTACTATGAAGTGAAGGCCAGAAACGAAGTCCATATATTGCATCATACAAAATA
TCCAGAAGAGGGAAGCCCACAGAGACAGAATGTGCAATGGTGGATGCCAGGGTCTGGGGAGAGGGGAGAGT
GGGGAGAAACTGCTCAACTGGTACAGGCTTTATTTTGGAATGATGGGAACATTTTGCAACTAGATAGAGGT
AGTGATTGCAGAACACAGAATGTACTGAATTCCACTGATTTTTTTCACCTTAAAATGGTTAATTTTCAGTC
CTGAGATTGGATAATCATAAAAAAATGGTTAATTTTATGTTATGTGAATTTCATCCCTATACATATTTTAA
ACCTCAGAAATATACACTAGCAGGCATGGAACAGGTCACTGTGGTGCCTGCCAAGCCCGGTGATGTTATCT
GGGGTCCCCGGCCAGCCTTAAGCCTCTTGCTGACCGGTGGAGGGCAGAACCTTTGCCCTAAAAGTATAATA
TCCACATGCTGGCATGATTCCTGGCCAGATGGCTTCTTTATTAGCAGTAATTGAAACTGCCTCGATACAGA
CACTGTACCTTGCAACCAAAAAATGACTCAACAATGATAATAAGGGTTAAGCTGGGCCTTTCTCTCTTTGC
CAGTTAAATTATATTTATTATAGCTTGACATGAAAAACAAAGCAACTCCAACAGGTATCACAAGGGCAAAG
GACATGAACATTTTATCAAAGAAGAAATGCAGCTGTCAAAAATACAGAAATATTCAACCTTGTTCATAATA
AAGTGGCTGGGCTCAGTGGTTCATGCCTGTAATCCCAGTGCTTTGCAAGGCTGAGACAGGAGGATCATTTG
AAGCCAGAAGTTCAAGACCATCCTAGGCAAGTCAGTTCAATACCAGACTTCATGTCTACAAAACATCAAAA
AATTAGCCAGGCATGGTGATGCATGCCTGTTGTCCCAGCTACTCAGGAGGCTGAGGCAGGAGAATTGCTTG
AGCCTGGGAGGCTGCGGTGGCGGTGAGCCATGATTGTGCCATTGTACTCCAGCCTGGGCAATGCAGCAAGA
CTGTCTAAATAACAAAAATAATAGTAAAGAAAAGGATTGGGATGCCATTTACTTGCGTATTCAATACACAG
AGTTAAAAGTAATTTCTACGTTTTCTATTTTTTTATTACTAAAAAAAGCTGGACCATTCTCACAGCCTGAA
ATGCTTCTCACTTTCCCTTCTTCTGTCCAAACACTTCTCTATGATAATGCAAACAGTCACTCCTTTAGGAA
GACTTCACCCCAGGTAGTTCCAGATCCCCTTATCTCTGCCTTCCCAGAACTCCTGGTGTCTCTCCAGTTCC
CTCCGTGTGGTGAAGTACCCTACCTAGGGTTTCAGTATGGCTCTGTCTGCAAAGGTCTTGTTCACACCTTC
CCTTATGGTTCTGTTGCCCTGTGTTGTGTCATAGCACAGGGCACAGTGGAGAACCCATTCACACTGATAGA
GAGGGCCCCATGGTCCTGGAGATAACCATGTAACCGATCAGAATAAGGCATTGAGGGCTGGGTGTCAGGCG
TGGGCTGCACTTGGGTGGGCAGGTCCCCTGGAAAGTCACTGGGTTTGGCAAGCTTCCTAGTAACATGTCTC
TCTGGGGTCCCCCTTGGAACTTCATGCAAAAATGCTGGTTGCTGGTTTATTCTAGAGAGATGGTTCATTCC
TTTCATTTGATTATCAAAGAAACTCATGTCCCAATTAAAGGTCATAAAGCCCAGTTTGTAAACTGAGATGA
TCTCAGCTGAATGAACTTGCTGACCCTCTGCTTTCCTCCAGCCTCTCGGTGCCCTTGAAATCATGTCGGTT
CAAGCAGCCTCATGAGGCATTACAAAGTTTAATTATTTCAGTGATTATTAAACCTTGTCCTGTGTTGACCC
CAGGTGAATCACAAGCTGAACTTCTGACAAGAACAAGCTATCATATTCTTTTCAATTACAGAAAAAAGTAA
GTTAATTGATAGGATTTTTTTTTGTTTAAAAAAAATGTTACTAGTTTTGAAAAGGTAATATGTGCACATGGT
AAACACTAAGAAGGTATAAGAGCATAATGCTTTTATACTACTAAGAATAATGTTTTCTCTAAGTTTTTTTT
GGTAGATGCTTTCATCAGATTAAGAAAATTCCCTGCTATTAGTTGTTGAAGGTTTTTATATCATAAATGAA
```

Figure 6 continued

```
   AGTTGAATATTATTATCATATATTATTAATATATTGTTATTGAACTATCAAAGCCTTTTCCTAAAACCATT
   GAGATGATCTTATAACCATTCTCCTTTAACCTGTTGACGAGATCATTGGTATTTATACTATTTCTCTGTTA
   ACCATTCTTGAGTCTCAGGTTTAAATTCAACTTGGTCATGGTGTGTCATCTTTGATCATTGCTGTCTGTGG
   CTTGCTACTGTTTTGTTTAGGATTTTTGCACTGATGCTCATCAATGAGACTGGCATGCCATCTTCCTTTGC
 5 AGTCCTGATTTTTTTCTGATTTGGATCATGTGGTTATGCCCTCATGGAATGAGTTGGGCATGATGCCTTT
   TTTTCATGTCTCTGGATTGATGGGACACTTTGGATTCTCTCCAGATGGCCCTCAATGGTCCCTGCCTCCTC
   ATTGTTAGGCCCCTGGGCAAGCCCTTCTCATTTCTGGTAGGCCCAGGAACCTGTGGGGTTTTGTTTGTTT
   GTTTGTTTCTTGAGTCGGAGTCTCACTCTGTCACCCAGGCTGGAGTTGGAGTGCAATGGCCCGATCTTGGC
   TCACTGCAACCTCCACCTCCCAGATTCAAGCAATTCTCCTGCCTCAGCCTCCTGAGTAGCTGGAATTACAG
10 GCACCCACCGACACACCCTGCTAATTTTTGTATTTTTAGTACAGATGGGGTTTCACAATATTGGCCAAGCT
   GGTCTCGAACTCCTGATCTCATGATCTGCCCGGCTTGGCCTCCCAAAGTGTTGAGATTACAAGCATGAGCC
   ACCACACCCAGTGAACCTGTGGTTTTTAGAAGCTCCCCATGCATGTGAATGCTGTGAGCATCCCAGGATGA
   CAGCCACTGTGTGTTCAGCTGTTGGAACTGTGAGAAAGCACCAGTGGGACCTTCTCCAGCACCTGCCTGCT
   GAGTTCATGGAAGAGGCTTGTTGGGGAGATGATGCCCTGGCTGACTCCTGAAGGATGGTTAGGAATGCACC
15 AGATGGAAGCTGGGTTGGACCCACTCTATGCTGAAGAACAGCTTGTGTGGACACAAGGAGACACGGATATG
   TCATTTTTGTAGAGCCTGAGGAGTGTCCAATCACACCATTTGCTTAAAACATCATGCACACTTGGAAAAGT
   GGACTGAGACCGAATGAAGAAGCTAACAGTGGCCAGATCAGAAAGGGTCTTGTGTTACTTCCTAGAGATAC
   TTAGATTTTATCCTGTGGGTGATAGGAGCAGTTGGAGGGACTGAAGACAAGGAAAGAAACATGTTTCAAGA
   TCTATGTTTTTCAAGACGCTTTTCTGGTGGCTGAGTAGGGAATTCCCTGGATAAGTCCTGCCCAGGGTCAG
20 GCAAAACAAGTTAGGGGGTTACTGAAATAAGGAGTATGAGAAATGGTGTAGGTTGTGCTGACGTTTTGTAA
   CACATCTCATGATGATCTTCATTTCCTTCACTAATTTCCTGTTTCATTAATTCCCTTCCACGTGCTCTTCT
   GAAATTTGCCTCACATTCTCTGATTTCTCTTTTACCTGTTGGTTTCATCACCTTTTACTTTTTGCTTTCCT
   GGAAACACAAATGATTCTGATTGTGACATGTCAGAATTATTTGCAACATTTGCCTTTCTGCTGAAACCATG
   AGTTCACTGAATACACAATTTAGTAAAGTGTAGGATGCACATGTCGTTTTCGTGGTCACAACCAGCTCTGT
25 AGCATTTTATAACTACACTGGCAGTGTGCTGGGAGGTGTAGAGAGAAATATTTATCACATGTGTGGCTGAC
   ACAACCTGCCAAGTTATTTTAGGAGCCTCCTTGGAATCCCAGCAAGAATGCTACCGGCACAATTTGTAATC
   ACAGCATCCTGCTCCATGCCTTGGCTTCATGGCATAGTCACTTCTGCAAGTCTCTTTCCAGCTGTCTGTTC
   CCATGTCTATAAAGTATGAGTTAAATCATCCTAACACTACTCATCTTACAAAGTTTTCTTGCTGATGTTAA
   GAGAGTTGGGAAGAACTGTATAAACTGTGAAGTGCCATGGAGATGTTAGTGGTTACTTTATCAAGAAATA
30 GACACTCTAGAATGGAGTAGAAAGCCAACAGTTATGATTGAGTCCTCCTCCTCTTCTTCTTTTTATTAATT
   TATAAAGAAAAGAGGTTTAATTGACTCACAGTTCCATATGGCTGGGGAGGCCTCGGGAAACTCTCAGTCAT
   AGCAGGAGGCAAAGGGGAAGAAGGCACCTTCTTCACAAGGCGGCAGGAGAGAGAGAGCTCCTGTTCTTTTT
   TGTCATAAAGTCTACAGAAGTGCTTATACTTCAGGACAAGGGCAGGCAGAGAGAAGGAAGGACATTGCTTC
   ACCCCAGCCCTCACTGACGAGTTTGCTAGGGGACCTCACTTTGTCCCAGAGTAGGGCAGAACTCTGGCCAC
35 TACCCATTCAGAAGGCCTGGGCTGCACTGCTAGTTCCTCACTAACTCTGTGTGGCCTTGGGCAAGGTTGGG
   CCTGTGTTAACAGATTATGACCCTGGGCTCTCAAGCTAGAGGATCTAAATTTGAATCCTGGCTCTGCTAAA
   GCAATTAGTGATGTAAACTTTAATGGGTCAGTTAACCTTCCTGTGGCTTAGTTTGCTCATCTGTAAAATAG
   GGATCATAACAGTATCAATACCACATGATTGTTGGACAGATTGAATCAGTTAATGCAGGGGAAGTACTTAG
   CATGACACGTATTCACTATCATTTCCTGGAGTAAGAGCTGTGTGTGAGTGGGTGTGAGCATGTGTGAAACC
40 TTTTCTCTGCAATCTCAGTTAAGAAACCAATCCAGAATTTAAAGTTCAGGGCCTAAATGGGTGGTTATCTT
```

Figure 6 continued

```
CTCCCAGTTCCATCCTATCCCACCTTTGCTCTTCCTCCCGCCCACAGGAGCTGTTGGTCCTTGATTGGGCT
GGAAGACCTGGTGGACCCTAAGTGATCTATAAGAGGAGAATAGAGAACAGGGAATGTCTTCAAAAATCTAG
AGGGACACAGAGGCTGAGAGGCAGGCAGTCCTGCAGGGTCTTCTGATTGGGACAAGGAGAACCTTGGTCTT
CACAGGCCAATTCTGGTCAGTTTCCCCCATGGACAGATGAGGAAACAGGCCCAGGAATATCCAAGGTCTCA
CACTTCCCATCTGTCAAGTCTTGTTGATTCTGTTGTATTCATGTCTCTCAAAGGGAGATAGAGTTTAGGGA
AGAAAGAAGGATCAACTGTGTCTGATACCACTGGGAGCTTAAGTAAAGGGTTCTTTTACTTCATAGCATTT
ATCCCAATTTGTAATTCAGTATTATTTGTGTGGCTGTTTGGTGTCTCTTTCTCCTATATGAGTGCTAGCTT
CATAAGGGCAAGGATTTTGATTCTTTAATATTTAGTGCTTGCCACATGCCCTGAACACAGCAGGCATACAG
GCTAACCAACATACAGTGGCATGAAAGTCATGAAAGTGAGACACCTACCTCCTCCAGTGCCAAGAGAGCAT
AACCATGCACCTGTCACTCTCCTCAACACCACCCCCAAGCATGAGGCCCAAAAGCATTAGCTAATCCCCTC
CTCCAGCCACTAAAACTTAAAGGCCAGGTGTGGTGGCTCCCATCTGAAATCCCAGAACTTCAGGAGACAGC
AGCAGGAGGATCACTTGAGGCCAGGAGTTTGAGATCAGCCTGGGCAACATAGCTAGGTCCCATCTGTACTA
AAAATTAGCTGGGCGTTGTTGCATGCCTGTAGTCCCAGCTACTAAGGAGGCTGAGGTGGGAGGATCACTTG
AGCCCAGGAGGTGGAAACAACAGTAAGCTATAATCACAGCACTGAACTCTAGCCTGGGCAACAGAGTGACA
CCCTGCCTCAAAACAATTTTAAAAATAAATAAGAGCAAAACTTAGATACCACGTGGTCACCCCAACATGCA
AAATCAAGTTTTCCCCTACTGAGAAGAATGGGGACTTGACAGCTGAGTTACAGAGAGATAATCTTCTTCTT
CTTTTTTTTTTTTTGGTTTACATCCTCAAGATCATGACTTGTGAAATTTGAATCGAATACACATGTAATTC
CAGAGCAATGTTGCCTCCGCATACCATCAGCAATTCACTTGGCTACTGGAAGTCAGGAT
```

Figure 7.

```
TCTAGAGAGA TGGTTCATTC CTTTCATTTG ATTATCAAAG AAACTCATGT CCCAATTAAA
GGTCATAAAG CCCAGTTTGT AAACTGAGAT GATCTCAGCT GAATGAACTT GCTGACCCTC
TGCTTTCCTC CAGCCTCTCG GTGCCCTTGA AATCATGTCG GTTCAAGCAG CCTCATGAGG
CATTACAAAG TTTAATTATT TCAGTGATTA TTAAACCTTG TCCTGTGTTG ACCCCAGGTG
AATCACAAGC TGAACTTCTG ACAAGAACAA GCTATCATAT TCTTTTCAAT TACAGAAAAA
AGTAAGTTAA TTGATAGGAT TTTTTTTGTT TAAAAAAAAT GTTACTAGTT TTTGAAAAGG
TAATATGTTG CACATGGTAA ACACTAAGAA GGTATAAGAG CATAATGCTT TTATACTACT
AAGAATAATG TTTTCTCTAA GTTTTTTTTG GTAGATGCTT TCATCAGATT AAGAAAATTC
CCTGCTATTA GTTGTTGAAG GTTTTTATAT CATAAATGAA AGTTGAATAT TATTATCATA
TATTATTAAT ATATTGTTAT TGAACTATCA AAGCCTTTTC CTAAAACCAT TGAGATGATC
TTATAACCAT TCTCCTTTAA CCTGTTGACG AG
```

Figure 8.

```
GGATCCAGTTTCAGCTTTCTACATATGGCTAGCCAGTTTTCCCAGCACCATTTATTAAATAGGGAATCCTT
TCCCCATTGCTTGTTTTTGTCAGGTTTGTCAAAGATCAGATGGTTGTAGATGTGTGGTGTTTGTTCTGAGG
CCTCTGTTCTGTTCCATTGGTCCATATCCCTGTTTTGGTACTAGTACCATGCTCTTTTGGTTACTGTAGCC
TTGTAGTATAGTTTGAAGTCAGGTAGCGTGATTCCTCCAGCTTTGCTCTTTTTGCTTAGGATTGTCTTGGG
AATGTGGGCTCTTTTTTGGTTCCATATGAAATTTAAAGTAGTTTTTTTTCCAATTCTATGAAGAAAGTCAT
TGGTAACTTGATGGGGATGGCATTGAATCTATAAATTACCTTGGGAAGTATGGCCATTTTCACGATATTGA
TTCTTCCTATCCATGAGCATGGAACATTCTTCCATTTGTTTGTGTCCTCTTTGATTTTGTTGAGCAGTGGT
TTGTAGTTCTCCTTGAAGAAGTCCTTCACCTCCCTTTAATTTGGATTACTAGATATTTTATTCTCTTAGTA
ACAATTGCAAATGGGAGTTCACTCATGATTTGGCTCTCTTTCTGTTATTGGTGTATAGGAATGCTTGTGAT
TTTTGCGCATTAATTTTGTATCCTGAGACTTTGCTGAAGTTGCTTATCAGCTTAAAAGGATTTTGGGCTGA
GACGATGGGGTTTTCTAAATATACAATCATGGCATCTGCAAACAGGAACAATTTGACTTCCTCTTTTCCTA
ATTGAATACCCTTTATTTCTTTTTCTTGCCTGATTGCCCTGGCCAGAACTTCCAATACTATGTTGAATAAG
AGTCATGAGTGAGGGCATCGTTGTCTTGTGCTGGTTTCAAAGTTTTTGCCCATTCAGTATGATTTTGGCTG
TGGTTTTGCCATAAATAGCTCTTATTATTTTGAGATACGTTCCACCAATACCTACTTTATTGAGAGTTTTT
AGCAGGAAGGGCTGTTGAATTTTGTCGAAGGCCTTTTCTACATCTATTGAGACAATTATGTGGTTTTTAA
TCGTTGATTCTGTTTATGTGATGGATTACATTTATTAATTTGCATATGTTGAACCAGCCTTGCATCCCAGG
GATGAAGCCCACTTGATTGTAGTGGATAAGCTTTTTGATGTGCTGCTGGATTCAGTTTGCCAGTATTTTAT
TGAGGATTTTGGCATCAATGTTCATCAGGGATATTGGTCTAAAATTCTCTTTTTTTGTTGTGTCTCTGCCA
GGCTTTGGTATCAGGATGATGCAGGCCTCAGAAACTGAGTTAGGGAGGATTCCCTCATTTTCTATTGATTG
GAATAGTTTCAGAAAGAATGGTACCAGCTACTCTTTGTACCTCTGGTAGAATTCAGCTGTGAATCCATCTG
GTCCTGGACTTTTTGGTTGGTAGGCTATTAATTATTGCCTCAATTTTAGGGCCTGTTATTGGTCTATTCAG
ACATTCAACTTCTTCCCGGTTTGGTCTTGGGAGGGTTTATGTGTCCAGGAATTTATCCATTTCTTCTAGAT
TTTCTAGTTTATTTGTGTAGAGGTGTTTATAGTATTGTCTGATGGTAGTTTGTATTTCTGTGAGATCGGTG
GTGATATCCCCTTTATCATTTTTTATTGCATCTATTTAATTCTTCTCTCTTTTCTTCTTTATTATTCTGGC
TGGCGGTCTGTCAATTTTTTTGATCTTTTCAAAAAACCAGCTCCTGGGTTTCACTGATTATTTGAAGGGTT
TTTTGTGTCTCTATTTCTTTCAGTTCTCCTGTGATCTTAGTTATTTCTTGCCTTCTGCTAGCTTTTGAATG
TGTTTGCTCTTCCTTCTCTAGTTCTTTGAATTGTGATGTTACAGTGTTGATTTTAGATCTTTCCTGCTTTC
TCTTGTGGTCATTTAGTGCTATAAATTTCCCTCTACACATTGGTTTACATGTGTCTCAGAGATTCTGGTAT
GTTGTGTCTTTGTTCTCATTCATTTCAAGAACATCTTTACTTCTGCCTTCATTTTGTTATTTGCCCAGTAG
TCATTCAGGAGCAGGTTGTTCAGTCTTCATGTAGTTGTGTGGTTTTGAGTGAGTTTCTTAATCCTGAGTTC
TAATTTGATTGCACTGTTGTCTGAGAGACAGTTTGTTGTGATTTCCATTCTTTTACATTTACTGAGCATGC
TTTATGTCCCATTATGTGGTCAATTTTAGAATAAGTGTGATGTGATGCTGAGAAGAATGTATATTCTGTTG
ATTTGGGGTGTGGAGTTCTGTAGATGTCTATTCAGTCCACTGGGTGCAGAGCTGAGTGGACATGAACATTT
TATCAAGAAGAAACACAGCTATCAAAAATCCAGAAATATTGAACCTTGTTAATAATAAAGTGGCTGGCCT
CTGGTTCATTCCTGTAATCTCAGTCCTTTGAAAGGCTGAGAAAGGAGGATCACTTGAGGCCACAAGTTCAA
GACCATCCTAGACAAGTCAGTTCAAGACCAGACTTCATGTCTACAAAACATCAAAAAATTAGCCAGGCATG
GTGATGCATGCCTGTCATCCCAGCTACTCAGGAGGCTGAGGCAGGAGGATTGCTTGAGCCTGGGAGATTGA
AGTGGCAGTGAGCCATGATTGTGCCATTGCACTCCAGCCTGGGCAATGCATCAAGACTCTGTCTAAACAAT
AATAATAATAATAGTAATAGTAATAATAATAATAATAAAGAAAACGGTTGGGACGCCATTCCTTACTTATT
CAATACACAAAGTTAAAAGCAATTTCTACTTTCTCTATTTTTTTATTACTAAAAAAAGCTGAACCATTCTC
ACAGCCTGAAATGCTTCTCACCTTCCCCTCTTCTATACAAACACTTCTCTGTTGATGATAATGCAGACAGT
CTCTCCTTTAGGAATACTTCACACCAGGTAGTTCCAGATCCCTTATCTCTGCCTTCCCAGAGCTCCTGGT
GTCTCCCCAGTTCCCTCTGTGTGGTGAAGTACCCCCACCTTGGGTCTCAGCATGACTCGTTCTTTGAAGGT
CTTGTTCACATTTTCCCTTATGGTTCTGTTCCCCTGTGTTGTGTCACAGCACTGGGCAGAGTGGACAACCC
ATTCACACCGATAGAGAGGGCCCCATGGTTCTGGAGATAACCATGTAACTGATCAGAATAGGGCATTGAGG
GCTGGGTGTCAGGCATGGCTGCACTTGGGTGGGCAGGCCCCTGGAAAGTCACAGGATTTGGCAAGCTTC
CTAGTAACATCTCTCCCTGGGGTCCTCTTGGAACTTCATGCCCGATGCTGGATGCTGGTTTATTCTCGAGA
GATGGTTCATTCCAATAATCAATGAAACTCATGTCCCAACTAAAGTTCATAAACTCCAGTTTGTAAACTGA
GATAATCTCAGCTGAATGAACTTGCTGACCCTCTGCTTTCCCCAGCCTCTCAGTGCCCTTGAAATCATGT
CAGTTCAAGCAGCCCCATGAGGCATTACAATGTTTAGTTATTTCAGTGTTTATTAAACCTTGCCCTATGCT
GACCCCAGGTGAATCACAAGCTGGACTTCTGACAAGGACAAGCTATGATATTCTTTTCAATTACAGAAAAA
GTAAGTTAACTGATAGGATTTTTTAAAGATGTTACTAGTTTTGGAAAGGTAATTTGTGCACATGGTAAACA
AGAAGGTATAAGAGGATAATGCTTTTATACTGCTGAGAATAATGTTTTCTCTAATTTTTTTGGTAGATGC
TTTCATCAGATTAATAAAATTCACTGCTGTTAGTTGTTGAAGGTTTTTTATATCATGAATGGGAGTTGAAT
ATTATCATGTATTATTAATATATTATTATTGAACTAGCAAAGGCTCTTCCTAAAACAATTGAGATGATCTT
ATAATCGTTCTCCTTTAATCTGTTGATGAGATCATTGGTATTTATACTTTTTCTCTGTTAACTATTCTTGA
GTCTCAGGTTTAAATTCAACTTGGTCATGGTGTATCATCTTTGAACACTCCTGTCTCTGGCTTGCTACTAT
```

Figure 8 continued

```
   TGTGTTCAGCATTTTTGCACTGATGCCGATGAATGAGACTGGCATGTCATCTTCCTTTGCGGTCCTGATTT
   TTTTCAGATTTGGATCATGTGGCCCTCATTGAATGAGTTGGGTGTGATGCCTTCTTTTTCATGTATCTGGA
   TTGATGGGACACTTTGGAGTCTCTCCAGATGGCCCTCAATGGTCCCTGCCTCCTCATTGTTAGGCTCCTAG
   GCAACCCTTTCTCATTTCTGGTAGGCCCAGGAACCTGTGGGTTTTATGTTTGTTTGTTTGTTTGTTTGTTT
 5 GTTTTTTGAGTTGGAGTCCTGCTTTGTCTCCCAGGCTGGGGTTGGAGTGCAATGGCCTGATCTCGGCCCAC
   TGCAACCTCCACCTCCTGGGTTCAAGTGATTCTCCTGCCTCAGCCTTCTGTGTAGCTGGGATTACAGGCAT
   CCACCACCACTCCTGGCTAATTTTTGTATTTTTAGTAGAGACGGGGTTTTACAATATAGGCCATTGTGATC
   TCTTGGACAGGCTAGTCTCAAATTCCTGACCTCATGATCTGCCTGCCTCAGCCTCCCAAAGTGCTGAGATT
   ACAGTTTTGTGCCTCCACACACAGTGAATCTGTGGTTTTTAAAAGCTCCTCATGCATGTGAATTCTGTGAG
10 CATCCCGGGATGACAGCCACTGTGTGTCCAGCTGTTAAAACTGTGAGAAAGCACCAGCGGGACCCTCTCCA
   GCATTTGCTTGCTGTGGTCATGAAAGAGGCTTGTTGGGGAGATGATGCCCTGGTTGACTCCTGAAGGATGG
   TTAGGAATGCACCAGATGGAAGCTGGGTTGGACCCAGTCTATGCTAAAGAACAGCTTGTGTGGACACAAGG
   AGACACGAACACATCATTTTTGCAGAGCCTGGGGAGTAGCCAATCGCACCATTTGCTTAAAACACCGTGTA
   CAGTTGGAGAAGTGGACTGAGACAGGCTGAAGAAGCTAACAGTGGCCAGATGAGAAAGGGTCTTGTGTTAC
15 TTCCTAGATATACTTAGATTTTATCCTGTGAGTGATAGGAACAGTTGCAGGGACTGAAGCCAAGGAAGCAT
   GCTTTAAGATTCCATGTTTTTTGAGATGCTGTCTGGTGGCTGAGTAGGGAATTCCCTGGATAAGTACTGCC
   CAGGGTAGGCAAAAGAAGCTAGGAGGTTACTGAAATAAGGAGTATGAGAAATGGTGTAGGTTTTGCTGATG
   TTTTGTAACACATCTCATGACAATCTTCATTTCCTTCACCAATTTCCTGTTTCATTAATTCCCTTCCACGT
   GCTCTTCTGAAATTTGCCTCATATTCTTTGATTTCTCTTTTACATGTTGGTTTCATCACCTTTTACTTTTT
20 GCTTTCCTGGAAACACAAATGATTCTGATTGTGACATGTCAGAATTATTTGCAACATTCCCCTTTCTGCTG
   AAACATGAGCTCACTGAATACACAATTTAGTAAAGTGTAGGATGCACATGTTGTTTTCATGGTCATAACCA
   GCTCTGTAGCATTTTATAACTACACTGGCAGTGTGCTGGGAGGTGTAGAGAGAAATATTTATCTCATGTGT
   GGCTGACACAACCTGCCAAGTTGTTTTAGGAGCCTTCTTGGAATCCCAGCAAGAACACCACTGATGCAATT
   TGAAATCACAATGTCCTGCTCCATGCCCTGGCTTCATGGCTTAGTCACGTCTGAAGTCTATTTCTAACTAT
25 CTGTTTCCACATCTATAAAGTATGAGTTAAATCATCCTAATACTACTCATCTTACAAAGTTTTCTTGCTGA
   TATTAGGAGAGTTGGGAAAGAACTGTATAAATTATGAAGTGCCATGGAGATGTTGGTGGTTACTTTATCAA
   GAAATAGACACTCCAGAATAGAGTAGAAAGAAAACAGTTATGATTAAGTCCTCCTCCTCTTCTTTTTTTTT
   AATTTACAAAGAAAGGTTTAATTGAGTCACAGTTCCATATGGTTGGGGAGCTCAGAAAACTTGCAATCAT
   GGCAGTTGGCAAAGTGGAAGAAGGCACCTTCTTCACAAGGTGGCAGGAGAGAGAGAGCTCCTCTTCTTTTT
30 TGTTGTAAAGTCTACAGAAGTGCATATACTTCAGGGCAAGGGCAGGCAGGGAGAAGAAAGGACATTGCTTC
   ACCCCAGTCCTCACTGACAAGTTTGCTTTGGGACTTCATTTTGTCCCAGCATATGGGACAGAGCTCTGGCC
   ACTACCCATTCAGAAGGCCTGAGCTGCATTGCTAGTTCCCCACTAACTCTGTGTGTCCTTGGGCAAGGCTG
   GGCTTATGTCAAAAGATTATGACCCTGGGCTCTCCAGCTACAGAATCTACATATGAATCCTGGCTCTGCTA
   GAGCAATTAGTGACGTAACCTTGGATGGGTCAGTTAACCTTCCTGTGGCTTAGTTTGCTCATCTGTAAAAT
35 AGGGATCATAACAACATCAATACCATGGGTTGTTAGACAGATTGAATCAGTTAATGCAGGGTAAATACTTA
   GCATGACACGTATTCACTATCATTTCCTTGAGTAAAAGCTGAGTGTGAGTGGGTGTGAGAATGTGTGAAAC
   CCTTTCACTGCAATCTCAGTTAAGAAAACCCATCCATAATTTAAAGTTCAGGGCCTAAATGGGTGGTTATCT
   TCTCCCAGTTGCATCCTATCCCACCTTTGCTCTTCTCCTGCCCGTAGGAGCTGTTGGTCTTTGATTGGGCT
   GGAAGACCTGGTGGACCCTAAGTGATCTATAAGAGAATGAGAATAGAGGACAGGGAATGTCTTCAAAACTC
40 CTAGAGGGACACAGAGGCTGAGAGGCAGGCAGTCCTGCAGGGGTCTTCTGATTGGGACAAGGAGGACCTTG
   GTCTTCATAGGCCAATTCTGGTCAATTTCCCCCATGGACAGATGAGGAAACAGATCCAGGAATATCCAAGG
   TCTCACACTTCCCATCTGTCAAGTCTTGTTGATTCTGTTGTATTCATGTCTTTCAAAGAGAGAGAGAGTTT
   AAGGAAAGAAAGAAGGATCAACTGTGTCTGATATCACTGGGAGCTTAAGTAAAGGGTTCTTTTACTTCATA
   GCATTTTTCCCAATTTGTAATTCAGTATTATTTTTGTCACTGTTTAGTATCTCTTTGTCCTATTAGAGAGA
45 TAGCTTCATCAGGACAAGATTTGATTCTTTAATATTTAGTGCTTGCCACATGCCCTGAACACAGCAGGC
   ATACAGACTAACCACATACAGTGGCATCGAAGTGAGACACCTACCTCCTCCAGTGCCTAGAGTACATGTC
   CATGGACCTGTCACTCTCCTCAACACCACCCCTAAGCATGAGGCCCGAAAGCATTGCTAATCCCCTCCTCC
   AGCCACCAAAACTTAAAGGCCAGGTGTGGTGGCTCCTATCTGAAATCTCAGAACTTTAGGAGACAGCAGCA
   GGAGGATCACTTGAGGCCAGGAATTTGAGACGAGCCTGGGCAACATAGCTAGACACCATCTGTACTAAAAA
50 TTAGCTGGGCATGGTGGTATACCTGTAGTACCAGCTACTAAGGAGGCTGAGGTAGGAGGATCACTTGAACC
   CAGGAGGTGGAAGCTACAGTGAGCTATAACCACAGCACTGAACTCCAGCCTGAGCAACAGAGTGAGACCCT
   GCCCTCAAAACAATTTCAAAAATAAATAAATAAAAACAAAACTTAGATACCACGTGGTCACCCCAACATGCA
   AAATCAAGTTTTCCCCTACTGAGAAGAATGGGGACTTGAGAGCTGAGTTACAGAGAGATAATCTGCCTTTT
   TTTTTTTTTTTTGGTTTACATCCTCAAGATCATGACCTGTGAAATTTGAATCTAATACACAAATCATTCC
55 AGAGCAATGTTGCTTCTGCCTACCACGAGTAATTCACTTGGCCACTGGAAGTCAGAACAAGCTTCCCAGAA
   GAGAGGTACCACTTGGACTACCAATATAAAAGGATGAAAATATCGGAGTGAAGGTGTTCCTTGCATCACTG
   AGTCCCTGGACAGCCTGTCCACTCATGCTGATATCTGAGCCTAATGCTTCTCTGAATGTTGAGATTTAACT
   TTGATCCAATGAAACCAGACCAAGAAAGAAGAAACGTCTTTCATTGTTGATAAGGACATGATTTTTCTCAC
   AATTTTATGATTATTTTTCCTTAGCTGTCCTATAATTATCTGCTTATTTGTCTCTTCTCCATGTGCTTAGG
60 GTACAAAGTTGACCAAGACCAAGAATAATGTCTGGGAGCACAATACTGACAGCACAGCTTTAAAAACATGA
```

Figure 8 continued

```
    TGAATGCTTTAATACAGGAAATGAGTAGGGGAGAGGCAAGTGGTGCTTGGGTGTTCTTCCAATGCATAGTA
    TCTTCCTTGACACAGTCAGTGCAGCTCTCAGTAGGCAAGTCCCTACATGTTAGAAGATGTTACTTTCTGTG
    GAATTAGGTGGCAGAACATGCCTTCAATTATTTTCCTTTGCAGAACAACACCAATTTCATTAGTTAGGACA
    GAGTGCTGGCTGCATTTGAATTCCAAGCAACGATTAGTCTATCACTGTTGGTATAGATTCCAACCAGTCAC
 5  ACCACCTCCTGAAGTTTGTTGGGCAGGTAAATCTTCATCTTAGAATAAAAATCATCTTAGCCAAGTAAGTG
    TTTTAGAGGAAAGAAGAAAACATAATCGTTTCCATAAGAGTTTTGTTTCTAAAAAAATAAGAAAGGCTCTT
    TGTTTAGGTGAGCTAATGAAGTTGTTGATAGTTATCAGATGACACTGGAATCTTTACTTGCCAGAATGTGT
    TCTGTGCACCTCTCGGTGTGGCAACATAGAGAGGGAGATCCTCCAGCAATGCCATTGATATGGTCAGAAAC
    TGCATCTTTCTTTCTCCCTGCTGAGATGGGGTCCTTTGTTCTAGAAAACCCAGGGGGTGCCACTGGGAGTA
10  ACCCTTGAGACAGGAACACGAATCTCAACCAATTTCTGGTTGCAGCCTTGAGTCTTACTATTTGCCATAGT
    GATGCTTAGCAAGGAATGGCAGGTGCACCAGAGCAGCAGAGGACCTAATATCTCCCTTCCTGTTAACTTTT
    TATAATATTTTATTGTGATCAGTATCAGTTGGGAAGCTACTTGCAGTCACTGAGCCTCAGTTTCTACATCT
    GTAAACTGGGGATAGTAGCATGGCCCTATTTAATGTGCTCAGCGAAGCCACTGAAAGGAGACAGAAATGTA
    CCAGAATTCCCTGGACTTTTATCCTACTTCTCCTGGGGATTGTCACCCACCTACCCGTGTCTGTCCTTTGT
15  TGCTTTGACGCTGTCACTTCTTTTCTTAGGTACCTCTCTGTAGGGCTCCATTATTCCAGGGATTCCAGAGT
    TACAGCACATGCATACCTCCATCCAAGCATGTTTATTTGTCTCCTGCTTCACTAGGCTGTCCCCAAGGAAC
    ATGTGGCTCCCGGCACATACCTGGCACAACACTGCACATGACATTCACCCACTTGGCCTTGAATCTGACAA
    GGAATCTGGCATGATGTTCACCTGCTGAGGCCAGGTGCCGAGCAGCCCTGGAGGCTTAGGGGCCAGAGGGA
    TGGGAAAAGGTGTCTTTCTGGGGTGAGTATCAGTTTCTGCAGGAGTGCTGAACCTGAGAAAGAATAAAGAG
20  AGAAGGAAGTGAACAAGCACAGCTTAAACATCATCTGTTTCTACTGAGTTTTAACAACTCTGAGATTTTGT
    TTGTCATGGAATCCATTTCTCAGGCCAAGCAGACACAGAACTTGGGTGTGAGTGATGATAATGAGCTGATA
    TAATTTTCACACCCTCATCACTGAGATCTCTCCCATCAGGAATGGGTCACAGGGCTCACAGGTGGCAGCAA
    CTGTTATTACAGGCCTCATCTCTACCAGCTCCTGGCACCTGCTCTCCTCTCATTAGAAAATCCTCCACTTG
    TCAAAAAGGAAGCCATTTGCTTTGAATTCCAATTCCACCCTCAAGAGGCTGGGACCACCTCATTGGAGTCC
25  TTGATGCTGTGTGACCTGCAGTGACCACTGCCCCATTGTTGCTGGCTGAGGTGGTTTGGGTCAACCTGGCC
    ATCTGGGCAGCTGTTCTCTTCTCTTCTTTCTCCCCTACTGTTTCCAGACATGCAGTATTTCCAGAGAGAAG
    GGGCCACTCTTTGGCAAAGAACCTGTCTAACTTTCTATCTACGGCAGGACTTTTGAAAGCTACAGAGGAAG
    AAGCACAAATTGATGCTATTCCACTAAGCCATCAGCTCCATCTCATCCATGCCATGTCTCTTTTTTAGGGG
    TCCTCTTGCCAACAGAATCACAGAGGACAAATCTGAAAGTGCAGAGACAGCAGCTGAGGCACAGCCAAGAG
30  CTCTGGCTGTATTAATGACCTAAGAAGATGGAGTGGTCACCAGAAAGTCAGAGGAAGTGACACACAGGGGC
    CCAGCAATCTCAGCCAAGTCAACTCCACCAGCCTTTCTGGTCCCCACTGTGTGTACAGCACCCTGATAGGG
    ACCAGAGCCATGAGAGTGAGTAAGACCAGACTATGCCCTTGAGGAGCTCACCTCTGCTAAGGGAAACAGGC
    CTGGAAACACACAATGGTGGTAAAGAGGAAAGAAGACAATAGAACTGCATGAAGGGGATGGAAAGTGCCCA
    GGGGAGGAAATGGTTACTTCTGTGTGAGGGGGTTGGTGAGGAAAGACTCTAAGAGAAGGCTCTGTCTGGCT
35  GGGTATGAAAGGATGTGTAGGAGTCTTCTAGGGGGCACAGGCACACTCCAGGCATAGGTAAAGATCTGTAG
    GCATGGCTTGTTGGGATGAGTTTCAAGTATTCTGGAATGAGGACAGCCATAGAGACAAGAGGAGAGTTAAT
    AGATTTTATGCCAATGGCTCCACTTGAGTTTGTGATAAGAACCCAGAACCCTTGGACTCCCCAGTAACATT
    GATTGAGTTGTGTATGATTCTACATAGAATATTAACTCAATGGAGGTCAGTGAGTGGTGTGTGTGTGATTA
    TTTGCCAACTGCCGAGGTGGAGAAGCCTCTTCCGACTGCAGGCAGAGCACGGGGGCCCTGCTACTGGCTGC
40  AGCTCCAGCCCTGCCTCCTTCTCCAGCATATAAACAATCCAACAGCCTCACTGAATCACTGCTGTGCAGGG
    CAGGAAAGCTCCACACACACAGCCCAGCAAACAGCAGCA
```

Figure 9.

```
GCCAATTAGAAGAAACACAACTACAAGGTCAGGGCATATTATTCAAACAGTAGAGACAATACAGTCAAATA
TTTGGCAGAATTACAAAATATCTCATTGGAAAAGACACGCAAGGGAAATCAACAAAAAGATATGAATCAGA
ATTCATCTGTGTCTCAAGAAAAGGTCATGCGATAAATTAAGTTCTGCTAGTGTTTCTACACTACCGTTAGC
CTCATTACCTTATTTTTTAAGTGTTAATATAGTTTTAGGTATTTTACATACATTTTTATTATTAATTACAA
CCAAAGTGCAACTTGTAATAGCAATTCCTTCACATTTTTTTTTTCAAATCTTGCACCTTAAAATCCACCTC
GGGCCTCAGTTGGCCAGCTTTGGTATCTGATACTTGGACTACAGATACCACTAAGGCAAGTAGATAAAATG
TACTCTAGGACCTACAGCCCTTCTGCTAGATCCTGAAGAATGATCATTAAAACAAGCTGGTCTAGCTGGTC
AAGAGCAAAAATAAAATCAAGATGACAGAAAATTGATGCAAAAGTGAAGTAAAATAGCTAGAGAATATGAT
TGCGCCTGTCCCCTTAGCATGGATTCCCATGCTAGCCAATCTAAAATCCTCACTGTTAGAATCCTCCTGTC
AATATGATAGAATGAACAGCAAGCTCAGTGTCAGAAAACCTGTGTTGTTAACTTGGCCCTCTTTCTAGCTG
AATGTGTGTTTTTGGTCAAGTTCTTTGGCATTTCAGAGACTCAGAGTAGTGAAGGAAGTGGATAAGATGAC
CTCTACATTCTCTTGCAAGCTCAAACATCTATGAATCCAGAGAGAAAAACTAGAGCATGAAATTAAGGTTA
TTTTAAAGAAATAACCTTAAAATTATTAGTATTCGAGGATCTCCAATATATTCATGGCACCACTCAAAACT
TTCCTTCTGCTCTATCCCGTCTTGGCTCAAAGTTATCTCCTTAATGAGGTCTGCCCTGACTATCCTACTTA
AAATTGTAAACTTTGCCCACCTGGTACTTCCACTCTCTTTCCCCTGCTCTGTTTTCACCGTAATACTTTA
CTCTTTTTAACATACAAAATCACTTATTTACTGTGTTGTTATCTATCTGCCTACTCTTACCATCAAATATA
AGTTCTACCTAGGCAGGGATTTTTGTATGTTTTGCTCATGGATATATACGAAGCACTTAGAGTAATATGTG
ACATATACAGGGTACTTGATTAATACTGTTGAGTGAATGAATGAGTTTCCAATACAAATTTAAAATAAAAT
ATTTCCTAACTTAAAATTGTAAAGTCAGATCTAACCAACTGTTCATTGGTCTGCTAGCAGTGTTTCTTGTA
TATGGAAATATATTTTAAATAGATATGTCCTGTGAAATAATACTAAGTGTTCTAAAGAAATAAGTGAGTGA
ACGTTACCTCATTGAACTAACTTGACCTTGCTCCTGGGAGAGAGTTCATTTGAGATTAAACAAGTTCAAAG
TCTATGAATCATAAAACGATAAAAAAAACTAAAAGGGAAATGGTGTTTTATAAGCTCTGCAATTCAAAAG
CCATTTCGGGTAATATTGTTATTTTTATGTCAGGAATTCCTCAGTGCTGATATCTTAGGGCAAAGGGTTTG
GTTATAAATTAAGAGAATGAGGAAATAGGTACATAGTAGGATTGTTCCAACCAAATATGTGTTGAATGTCA
AAGGAATTTCCCTGAGGAATAATCTTCAGAATAATTTGCTAAGCACAGGAGAAAATTTGGCTTATTACTTT
ATAGCCAGATTTCATTTTAATTGAAACTTCTTTCAAGCAAATCACTTACTAGTCTATTAACAATAACAAC
ATAAACACAAGTAAACATTCGGAATATAGACATCCAGGTACTAAGCTGATTGCTTTACACTCACTGTCTTA
TTTTACAAGTAAGGAGTTTTAGTTGCAGCAAAAGAAATAAATTTTCCAATGTCAAATGACCAGAACTTAAA
CCCAATCTGTTTGGTGCTAAAGCCAATGTTCTTTACTGCAATGTTGGGTTATCTTGTTTCTAAAACTTAAA
TTTATCAGTAAAAGGCAAAATTTGCTATTATTGAGGACATTAAAATCATATTTTGTAGACTCTGAGGACA
AATCCAACAAAAAGTTCCAACTATTTCTTGGCAGGCATCATTGAAATTGGTATATAGCTTCCTTGGGTAT
TGACTTTGAAAAGGAAGTTGGTCACTTTAGATATATAAGTTCAGTCTGTTTGTAAAAACAAAATGAAAACA
AAACAGTTGCCTTATATGCTAAAATTATCCTAATCGTTTTCACCTTTAACAACATATACACACAGAACTTG
AGGAACTTTACACGGCTCATCTTCATATTGTCAGCATCTAGCAAAGTACTTGCCACATAGTGATCAATAAA
AGTTTTAGCCAGCCTGGGCAACATAGTGACAGCCTATCTCTACAAAAAAAAATTAGCCAGGCAAGGTGGCG
CACACCTTTGGTCCCAGCTACTTGAGAGGAGGATGTGGGGAGATCCTTTGAATGCAGGAGGTTGAGGCTGC
AGTGAGCTGTGATTGCGCCACTGTGCTTCAACCTTGGTGACAGAGCAAGACCCTGTCTCACACACACACAA
ATTAAGTAAAGAAAAAAAAAAGAATCAAAGAAAAAAATAATTCCCCAGCTTAAGTCCATCTTTATTTGTTT
GGATAAGCTATAAAGTGTCAAATAATGCTGTTAATGGACATTTCTCTAGCTCTCCCAAAGGAGGAATTGAG
CACATAGTATGTGCTGTATTTTATATACAGAATAAAAATAGAGACAAGATTTCTACCCTCACAGAACTTAA
ATTCTTCAGGAGAATGACACTGAAGTCCTTAATTGGACTTCTCTCTTCTGTATTATCTTCCTCAAGTGGAG
GTATATGGTGCTTAGTTATGAAAAATACCTCCAGGGCTTTGATCTTCTCAATAACTCTTTGAGGCTGATAT
GAAAACAGTAATTAGAAAAAAACCATGTATCCAACTTATATAGACAGTTGATGACCAAAGCTAGAATCCAG
TTATTTCAGCCTCCCATGTATTTTCTTATTACTTAAGGAGAATCTCTATCTCTACCTCTTTCTCTCTTCTT
CCTCTCTCACTTTTCTTAGAAACATGGGTAAGATTTTCAGAAATATGAGAAACTTATTAATAAATGAAAAA
TACTGGGAATTCTCAATGTTTCTTGTTTTAGCCAGTTAATTTTGGCCTTCATTCAATGTGAGTGTCCCTTA
ATAAGGAGCAAACTCCACTGAGAGATAGATACTAATAACCAGGATTCTGAAAATGCATTCTCATCCCATC
TCCAAACTTTTATAAAAATATTATAAAATAATACACTTTTAATATAGGAAATTTCTCAAATACAGAAAAA
ATTAAAGTAAACTCAGACCTAACTTTCATCACTAAAAGATAATCACTCTTGACACTTTGATATCTTTATCT
CTAATATTACACCAATTAATTTGCTTGATATAGTGAATATTATGCTATTATAATTTTCCCCTGCCTTTTGT
CCTTGCATATTAGCATAGGTATTTTCTGAGGTTATCACAAACTCTGTAAGCACGTTTTATATTACTACTTT
TTTAAAGAGGATGTATAATAATTAATTCATCCATATATATGTGGTTAAGTATTCAGGTCACTGCTCATTTT
TCACTGTTATAAAATAAAGCAGCAATGAATACCTTTGGCTGATATTTTTTTCTGTACTTGGAATTATTTCT
TTAAGATAGATTTCCTAAAATTGAATTACTGAGTCAAACAGACTTAAGTTTTCCTTATGTATGTTCCTTA
TTCATTTGAATAATTTTCAACTCCTACTTGTTTATTTAACTCTTGTGAGCATGTGATAGTCTCATTTTTCA
AAATATCTTTGCTGTTGTAATTTGCATTTCTTTGTAGTTAGCATGAATATTTCAGTATGTTTTCTTCTGTG
TACCAGTATACTACATACTTTTTTATATGAATTGCCTATTTGCATCTTTTGCTCGGTTCTATTAGACCTTT
```

Figure 9 continued

```
GAATTTTTTCTTATCCATTTATATAAGCTCTTTATATATTAAGAATATTAACCTATTGTGATATTTGCAAT
AAATAGCTATATGGTTTGTTGTTGGTTTTAAATGTGAATTTATTCAATTTTCTTCATAATTTTGTTGTTTT
TATAGATTTCTTTAAAAGTAATAAAATTATTGCCATATTATTATTTATTTTCAATGTCCATTACTAGCCCT
TTCCAGTCATCACTTTTACTCTCATGTTCTTAATTTTTATTCATATCTTGGCTCCATTGACCATCTTTATT
AGGATATTTGGGAAATAATACAATTTATACTAAACACACATCAAATCTTACCTTATTTTCTTCTTACAAAA
ACCCTAGGAATATGCTGTTTTTGTCTTTATTTGAATGACACAGAAATCAAGGTTTTTGAGCAGTGGAGTAT
TTCTTCAAATGACACAGAAATCAAGTCTTTTGAGCAGTGGAGTATTTCTTCAAAGCCACACAGCTAGTAAG
TCATGAAGCTGGAATTCCAAGAGTTGCCACTTCATTTTCTTCTTTCCCTTTATCTTACTCAGTTGTCTTCT
CTCCTCTTAATTTTGTCATTCATTTAAAAACATTTCTTGTGCTATTATGGTAGATTTATTTTAATAGGGGG
CAGTGACTTACTCAGAGAGATGATTCTCTAATGGAGTTTTAAAGATCTTAGAAGTTGATAGAGGAGGCTGG
GCGTGGTGGCTCATGCCTATAATCCCAGCACTTTGGGAGGCTGAGGTGGGTGGATCACTTGAGGCCAGAAG
TTCAAGATCAGCCTAGTCAATGTGGTGAAACCCCATTTCTACTAAAATTACAAAAATTAGCCTGGTGTGCT
GGTGCACTCCCATAATCCCAGCTACTCAGGAGGCTGAGGCATGAGAATTGCTGGAACCCAGGAGGCGGAGG
TTGCAGTGCGCCTGGATTATTAACACTACACTCCAGCCTGGGAGACAGAGTAATACTCCATCTCAATAAAA
AGAAGTTGATAAGGGAGATAGTTCATGGCAACGGATCTTTGAAGGCACGCTAATGATAACTTAGGCATTTA
GCCTACTAGTGTAATTTCCATAAATCTGCCTCTGATGTCATACTCTCAGCACCTAATATTTTCTACAAACA
TTTATTGAAACTTTATTTTGTATAAGTCTCTGTCCAGTTTGAATATTTAAAAAATTCATAATCATATGAAA
CATTAATAATAAATACAAAATGAGAGATGCCGATACTGAAAAGTAGGATTGCGGAGTGGTAGAAAATATTT
CTGGCTGTAGTAGATGGGGAAGTGTTCAAAGAGGAGTATAATTCAGGTTTCCATTTGCCATCGACTTATCA
CATGGCTAACTCACTAAGCGACTTAATTAAAATTAAATTAATTTATCATCATCTGATCACCATTTCACACA
ACTCATGTCTGTTGCTGTATTGGCTAAATGATGGCAAGACAAACGACCTCTGAAAATGATCCTATTGACCT
TCGGAATCTGGATTTTTTTTTCAATGCAGGTGTCCATAGAAGCAATCTGATGTAATCCAACATGAGTTCAA
GCACAGTCATTTAATATCCCTATCAAGTACAGTCATTTAATATCCCTATCATCACATGTCCTTCATCA
TAAAAATCATTACATGTGAAAGGGTGGAGAGTGTGTGGATCCCTTATTATTGTGTTATTGTAACACAATAA
CAATATTGTGTTATTATTGTTAACACAAGTGAGTCATATGTCTTGCTCTTTGGACTGAGTGGAAACTTGTA
TTCTTTCTCTGCCTCAGGTCAATTAACTTCATTGAGGTGAGTTGCATTCCTTCTTTAAGCATGTTGAACCT
TCAATCTGGACTCAGATGGGCTAAATAGAGGAGCTAGGAAAAATACAGAAAATAAATTATTAGAGAGATCA
GAGAAAGATACATAAGATTTACAATAAAAGAATTATGAGAAAAACATCCAAAAGAATTAAAAACCATAGGA
GAAGGAAAAATAGGTGAACAGCTTTTTAATTTCTATAAATGTGTTGTTAATACTCATAATAAAGGACTCAG
AGCTGGGATATGAGAATAATAGGTCAAACGTATATGGATACATAGATGTGACTACATACATGAGTTGCAAA
GAATGCTAAGGAGGGCAAAAAGAGATTGAGAAGAGGGCATTATTACTAATATATAGCAATGTTGAATGTTT
AGGGTGTTTCAGGCACTGTACAAATCTTTTAAATACACAAATCACTTAATCTTGCCATAACATTAGAAGAT
ACTATCTACTCTTTACCAAAAAGGTAACTGTGGGATAGCAGAGTTAAGTAACCCGTTCAAACCTATGCATA
ATAATCAGCAGAGATGGTCCTTATCTAAGTTTTTCTGCCTTTGAAGTCCAAATAGTTTTAATGCAGCCAGGT
ACTAAAGAAGAAAACTTTTGTAAATTAGTTTAGTTTAATGATTTACATGTGGAAAAGCACAGAGTGAAAAG
CACATATCATCTGAGAAGCCCAGTGAGTTTGGCTGAAATGGAGTGAACATGTACATGTTGAGGGTGAGGAA
GATGATTAGAGAGAAGTGATGTGTTGTGGTTCTTAAAAGCTAAGAGGAAACTGTTAGATATGATATAGTCT
GTGGCAGGGAGCCATTGCAGGTTTTCCAAGATGGACTCATAAGGAGAAAACACTTCGTGGGACTGGAAAAG
GCAGTGAAGTGGTGTGTCCTATGATAATGTACTACAGTGTAGGATAGTGGTTAAGAGTACAGTTATGAGAG
AGGGACTACTGGTTAGCACCTTACCTGCTGTGTGACTGGGCAAATAATGCAAACCTCAGTGTCTTTTATTG
TAATATGGGAGTAACAAAAATAGTAACTACTTCATAGGATTCTTGTAAAGATTAAATGACTTAATTTCTTT
GAAGTGCTTGGCAGTTCCTGATAAATGACCAGTAGTTAATAAATGTTAGTTGTTATTATTATCATTATATA
TTATTACTCCCATAGATACATATAGAACAGACTGCAGCAGAGAGGCAAATCTTTAATGTTGTCAGAGTATA
GACAAGTTGGTGAAATGGCTACATGAGAGCGGAGACAAGAAGGTGCAGATTGTGGCAGTCACTTCAAATG
GAAATATCACCGCTTGAATGAAGGTATATGAGTGTCAACTTGCAAGGGGACCAGGTAGGTTTCATCAGAAA
TTAAGGAAGCTTAAGGAGAACAGCCAAGTTCAGCTTGACAGAAGTGGTGGTGGCACAAATGCAAGACTGGT
GTCTTTCAAGAAACCAAGGACTGTTGAAAGTAGCAAGAGCTAGTTTGTTTTAGGTCCATCATGTTTTATAT
TCACACTTTCATGTCAGTGGAGCAAAGAAATGGAATACAATATAATAGAATGGTAGAATCTTATTTTTAAA
ATCTGTGTTATTCTGATCTTTAACTTACTTATATCTTTGATAGAGATCTTTACCTGATGCTCAAGATTGTA
GAAATAGTATAATCAACATAACAGTATAGCACTGTATTTATATCCTGCACTGTTTAGGGAGGGTTTAAGGC
CATTCAAAAGGATACATAAAATACAACAAGATTACATAAATGAAAGGTGAGATAAAGCAACAAAGCAAAAC
AAAAGTGAAAACAGAGATCATAGGCACAAATAAGATTAAAAACGCATGTAATGAAGATGAAAGCTTTTACA
TTTACCCCAGATGGACCACAGGGTTGTTGTTAAGCCCTTTAAACAGTGAACAATGCTGTACACTTGCATATG
CAATTAGAACATGTGGAAAAATAGTGGCCTGTTAGAAGCCTAATTAACAATTTGTGAAAAAAAAAAAAAAA
AAAAAAAAAAGAGGCCGAGCTGTAGCTCACGCCTGTAATCCCTGCACTTTGGGAGGCCGAGGCGGGCGGA
TCACGAGGTCAGGAGATCAAGACCATCCTGGCTAACACAGTGAAACCCAGTCTCTACGAAAAATACAAAAA
ATTAGCCGGGCGTGGTGGCGGGAGCCTGTAGTCCCAGCTACCTGGGAGGCTGAGGCAGGAGAATGGTGTGA
ACCCGGGAGGCGGAGCTTGCAGTGAGCCGAGATCCTGCCACTGCACTCCAGCCTGGGCGACAAAGCAAGAC
TCCGTCTCAAAAAAGAAAAAAGAAAGAAAAACAAAAGAAAACTTCATTGTATTGTAAGGCCAAGAACAAAA
TATATCAAGATAAGGAAAATTTGTAGTCAAGAATAGAAAAAAATTATGGCTTTGAAGTATGAGTTATTTAA
```

Figure 9 continued

```
AGAAAGTGGAAACATCCTCAGACTATGCAGTAAAAAACAAAGTGATTTTCTTCTTCTAAACTTATGCAATA
AACTGATAGGTAATATGTGAAAGTCATAGAATGTAGACTAGAGGATACAACAAACCTATTTCCTCTATGTT
CATAAGAAGTAAGAAAAGCTCTGATGTGAGTTAGCATTGCTTTACAATTTTGAATTGTGCAGATTGCACGT
ACTTTTCCTCAGTTTGAAGTAAATAGTGGACAGGAAAAAATATTAAATGTTGGCAGTAAATATGGAAGGAA
ATTACAACTAATGTAATATGCTAAAACATGCTATGTTTATTTTACTAATTTGAATTAAAATGTAAGAATTT
AAAATGCCCTGGAAAAACACGGGCATTGATCTGACGTCTGAAGTTTTAAAATATTACACACTTTGAAATAG
CATTTGTACCTTGAAATACCTGTCTCTATATATTTTTTAAAACTTCCTTTTTCTTTCATTCCATTTATCAT
CAAATAAAGGATGAACAGATGTAACTCAGAAACTGTCAAGCATGCTGAAGAAAGACCACTGCAGAAAAATT
TCTCCTAGCCTTTTCAAAGGTGTTAGGAAGCAGAAAGGTGATACAGAATTGGAGAGGTCGGAGTTTTTGTA
TTAACTGTATTAAATGCGAATCCCGAGAAAATTTCCCTTAACTACGTCCTGTAGTTATATGGATATGAAGA
CTTATGTGAACTTTGAAAGACGTGTCTACATAAGTTGAAATGTCCCCAATGATTCAGCTGATGCGCGTTTC
TCTACTTGCCCTTTCTAGAGAGGTGCAACGGAAGCCAGAACATTCCTCCTGGAAATTCAACCTGTTTCGCA
GTTTCTCGAGGAATCAGCATTCAGTCAATCCGGGCCGGGAGCAGTCATCTGTGGTGAGGCTGATTGGCTGG
GCAGGAACAGCGCCGGGGCGTGGGCTGAGCACAGCCGCTTCGCTCTCTTTGCCACAGGAAGCCTGAGCTCA
TTCGAGTAGCGGCTCTTCCAAGCTCAAAGAAGCAGAGGCCGCTGTTCGTTTCCTTTAGGTCTTTCCACTAA
AGTCGGAGTATCTTCTTCCAAAATTTCACGTCTTGGTGGCCGTTCCAAGGAGCGCGAGGTAGGGCACGCA
AAGCTGGGAGCTACTATGGGACAGTTCCCAAGTGTCAGGCTTTCAGATTTCCTGAACTTGGTCTTCACGGG
AGAAGGGCTTCTTGAGGCGTGGATAGTGTGAAGTCCTCTGGCAAGTCCATGGGGACCAAGTGGGGTTAGAT
CTAGACTCAGGAGCTCCTGGAGCAGCGCCCAAACCGTAGTGGCACTGGACCATGTTGCCCGGAGCGCGCAC
AGCCCGCGCGGTGCGGGGACCTGCTCTCTGAGCCCGCGGGCGGTGGGTGGGAGGAAGCATCGTCCGCGGCG
ACTGGAACCGGGAGGGGAGAATCGCACTGGCGGCGGGCAAAGTCCAGAACGCGCTGCCAGACCCCCAACTCT
GCCTTCGTGGAGATGCTGGAGACCCCGCGCACAGGAAAGCCCCTGCAGTGCCCATCGCGGCCAGAGCAGCT
GGGGCATCAACGGCGGCGCTCCCTCTTACTGCTCTCTGGCTTCGACGGGGACTAGAGGTTAGTCTCACC
TCCAGCGCGCCTGAGGCTCATGCATTTGGCTAATGAGCTGCGGTTTCTCTTCAGGTCGGAATGGATCTTGA
AGGGGACCGCAATGGAGGAGCAAAGAAGAAGAACTTTTTTAAACTGAACAATAAAAGGTAACTAGCTTGTT
TCATTTTCATAGTTTACATAGTTGCGAGATTTGAGTAATTTATTTCTAGCCTCCAGCTCTGAAATAAATGA
CATGTTGTTGTTTTTAATTATTTTTAAGAAACGCAAGCTAGCCTTTG
```

SEQUENCE LISTING

<160> NUMBER OF SEQ ID NOS: 5

<210> SEQ ID NO 1
<211> LENGTH: 12983
<212> TYPE: DNA
<213> ORGANISM: Homo sapiens

<400> SEQUENCE: 1

```
ctggttcatc tcattgggac tggttggaca agagggtgca gcccacggag ggtgagccaa     60
agcagggtgg ggcgtcgcct cacctgggaa gcacaagggg tcgtggaatt ttctccccta    120
cccaaggaaa gccataaggg actgagcctg aggaactgtg cactctggcc cagatactgc    180 actttttccca tggtctttgc aacccgcaga ccaggagatt ccctccggtg cctatgccac    240
cagggccctg ggtttcaagc acaaaactgg gcagccattt gggcagacac cgaactagct    300
gcaggagttt tttttttttt tttccatacc ccattggcac ctgaacgcc agtgagacag    360 aaccgttcac tcccctggaa aggggctga aaccagggat ccaagtggtc tggctcggtg    420
ggccccaccc ccatggagcc cagcaaacaa agattcactt ggcttgaaat tcttgctgcc    480
agcacagcag cagtctgaga ttgacctggg accctcgaac ttggttgggt gctgtgggggg    540
```

```
ggcatcttcc attgctgagg cttgagtagg tggttttacc ttcgcggtgt aaacaaagct       600
gctgggaagt ttgaactggg tggagctcac cacagctcag taaggccact gtggccagac       660
tgcctctctg gatttctcct ctctgggaag gatatctctg aaaaaaaggc agcagcccca       720
gtcagggact tatagatgaa acccccatct ccctgggaca gagcccctcg gggaagaggt       780
ggcttccacc attgtggaag actgtgtggc aattcctcac ggatttagaa ctagagatac       840
catttgaccc agcaatccca ttactgggtg tatacccata ggattataaa tcattctact       900
ataaagacac atgcacactt atgtttattg taacactatt tacaatagca atgacctgga       960
accaatccaa aagcccatca atgatagact gaataaagaa aatgtggcac atatacactg      1020
tggaatacta tgcagccata aaaaaggatg agttcatgtc ctttgcagag acatggatga      1080
agctggaaac catcattctc agcaaactag cacaataaca gaaaaccaaa cactgcatgt      1140
tgtcactcat aagtgggagt aaacaatga  aacacatgg  acacagggag gggaacgtca      1200
cacactgggg catgtcgggg agtgggggcc tacgggaggg atagcattag cagaaatacc      1260
taatgtaggt gacgggttga tgggtgcagc aaaccaccat ggcacatata cacctatgta      1320
ataaaactgc acgttctgca catgtacccc agaacttaaa gtataattaa taataataat      1380
aatttctggg catgtaagta gctgtctttc aggttctact ttgatacata ttctgagaga      1440
attaaacctg tcaaagaaac cttgactttc aatggcaggc actggaattg accctaataa      1500
tgtgttttgg ggtaagccta ctcatattct caacctgtct gcagtagtcg ttagaatctg      1560
aacttcctga agttcatgtg caaagttgag ttaattgttt aatattcaac aaggattatg      1620
ccagtaagat ggtaggaaaa tattagatat gtgtcatcac tgctggtatt atttaaactg      1680
caacatattt tagctggctg ctgatctcag ccaccatgcc tgcattttat ctctgtctcg      1740
tggtctgcaa ccttggaagc tttgaactta gctcatagaa tcctgggcat caagaacatg      1800
tggttctaat ggctagatag ggaatgagag taaaaggatt ttgcccacgg tcacgtgagt      1860
aaacaacaga tttggagggg tctggactac tgtgatgact tcattctgac aatatgttcc      1920
agttgtcctt tcatttcctc ctaatcacat gtctggtctg atctggctgt ttcccacctt      1980
ccaattcctg ccttctccaa tgctccctc  cgtaggtcac tctgtggctc agagaccctg      2040
cttagcaagc gcccaacctt tcaattattt gttcagtaaa acttgaactc atgtctcccc      2100
ttcttgataa aaagaaaata cgttatgtaa tgtcgggtta ctctataact cttgtcctgt      2160
ctctcggcaa ctactgaact aactgttttc atattgagca aacgtttatg gaaggactgc      2220
caagagtcag gtactaggct tggtaatatt ccccgttctc tctagtcaaa gccaacacca      2280
gccagacttg cagatctagg tcccaagccc actgcagatc acaggccagg gtctggtctc      2340
ctctgagctc ctttgggagg gaaagacaga attattaaca cccattttgt agattaggca      2400
actgaggctg aggaagttta ataactcag  acagggcctg cacgtcagtc atattccaag      2460
gatccctact cactgtcttc tctctacaga acgagatgtc tctggagtcc atagaaagcc      2520
caggagcctg gctgggcacg gtggctcctg cctgtaatcc cagcactttg ggaggccgag      2580
gcaggcagat cacctgagct caggagttca agaccagcct gggcaacatg gcaaaacccc      2640
atctctacta aaaatacaaa aaattagctg ggcgtggtgg tgcatgcctc taatcccagc      2700
tacttgggag gctgaggcac aagaattgct tgagcccagg aggcagcagt tgcagtgagc      2760
tgagattgtg ccagtgcact ccagcctggg caacagagca agattccatt tcaaaaacaa      2820
aaacaaacac aaacaaacaa acaaaaatag aaagcccagg gacccctgc  gtcaggttcc      2880 cagccacacc ttttttcttgt cctcctctgt ctctggcatc ttctcacagg ttcctaattg      2940
```

```
tttgtggttg cacaaattca aaatcccaga aaaattacca cttcacaccc actcagatgg   3000 ctatttttt tttgaaggaa gataacaagt gttgacaaga acatggagaa attggaattc   3060
tcacccattg ctggtgagaa tgtaatacgg tgctgctgct atggaaaaca gcttggagtt   3120
tcctcaaaaa gttcaacaga atttcaatgt gacccagcaa ttcccctcta agttatagat   3180
ctgagaggat taaaaacagt tactaaaata cacggactca catatttcta acagtccaat   3240
tcacaagggc caaaaggtgc taatagccca catgtccatc gatggatgga taaataaatt   3300
gtggtctatc catacaatgg aatattattc ggccataaat ggaatgaagt actgacgcat   3360
gctacagaat ggatgaaccg caaaaaaaat ggatgaacac atgctacaga atggatagcc   3420
tcactttact atgaagtgaa ggccagaaac gaagtccata tattgcatca tacaaaatat   3480
ccagaagagg gaagcccaca gagacagaat gtgcaatggt ggatgccagg gtctggggag   3540
aggggagagt ggggagaaac tgctcaactg gtacaggctt tattttggaa tgatgggaac   3600
attttgcaac tagatagagg tagtgattgc agaacacaga atgtactgaa ttccactgat   3660
ttttttcacc ttaaaatggt taattttcag tcctgagatt ggataatcat aaaaaaatgg   3720
ttaattttat gttatgtgaa tttcatccct atacatattt taaacctcag aaatatacac   3780
tagcaggcat ggaacaggtc actgtggtgc ctgccaagcc cggtgatgtt atctggggtc   3840
cccggccagc cttaagcctc ttgctgaccg gtggagggca gaacctttgc cctaaaagta   3900
taatatccac atgctggcat gattcctggc cagatggctt ctttattagc agtaattgaa   3960
actgcctcga tacagacact gtaccttgca accaaaaaat gactcaacaa tgataataag   4020
ggttaagctg ggccttttctc tctttgccag ttaaattata tttattatag cttgacatga   4080
aaaacaaagc aactccaaca ggtatcacaa gggcaaagga catgaacatt ttatcaaaga   4140
agaaatgcag ctgtcaaaaa tacagaaata ttcaaccttg ttcataataa agtggctggg   4200
ctcagtggtt catgcctgta atcccagtgc tttgcaaggc tgagacagga ggatcatttg   4260
aagccagaag ttcaagacca tcctaggcaa gtcagttcaa taccagactt catgtctaca   4320
aaacatcaaa aaattagcca ggcatggtga tgcatgcctg ttgtcccagc tactcaggag   4380
gctgaggcag gagaattgct tgagcctggg aggctgcggt ggcggtgagc catgattgtg   4440
ccattgtact ccagcctggg caatgcagca agactgtcta ataacaaaa ataatagtaa   4500 agaaaaggat tgggatgcca tttacttgcg tattcaatac acagagttaa aagtaatttc   4560
tacgttttct attttttat tactaaaaaa agctggacca ttctcacagc ctgaaatgct   4620
tctcactttc ccttcttctg tccaaacact tctctatgat aatgcaaaca gtcactcctt   4680
taggaagact tcaccccagg tagttccaga tcccttatc tctgccttcc cagaactcct   4740
ggtgtctctc cagttccctc cgtgtggtga agtaccctac ctagggtttc agtatggctc   4800
tgtctgcaaa ggtcttgttc acaccttccc ttatggttct gttgccctgt gttgtgtcat   4860
agcacagggc acagtggaga acccattcac actgatagag agggccccat ggtcctggag   4920
ataaccatgt aaccgatcag aataaggcat tgagggctgg gtgtcaggcg tgggctgcac   4980
ttgggtgggc aggtcccctg gaaagtcact gggtttggca agcttcctag taacatgtct   5040
ctctggggtc ccccttggaa cttcatgcaa aaatgctggt tgctggttta ttctagagag   5100
atggttcatt cctttcattt gattatcaaa gaaactcatg tcccaattaa aggtcataaa   5160
gcccagtttg taaactgaga tgatctcagc tgaatgaact tgctgaccct ctgctttcct   5220
ccagcctctc ggtgcccttg aaatcatgtc ggttcaagca gcctcatgag gcattacaaa   5280
```

-continued

```
gtttaattat ttcagtgatt attaaacctt gtcctgtgtt gaccccaggt gaatcacaag    5340
ctgaacttct gacaagaaca agctatcata ttcttttcaa ttacagaaaa aagtaagtta    5400
attgatagga ttttttttgt ttaaaaaaaa tgttactagt tttgaaaagg taatatgtgc    5460
acatggtaaa cactaagaag gtataagagc ataatgcttt tatactacta agaataatgt    5520
tttctctaag ttttttttgg tagatgcttt catcagatta agaaaattcc ctgctattag    5580
ttgttgaagg ttttttatatc ataaatgaaa gttgaatatt attatcatat attattaata    5640
tattgttatt gaactatcaa agccttttcc taaaaccatt gagatgatct tataaccatt    5700
ctcctttaac ctgttgacga gatcattggt atttatacta tttctctgtt aaccattctt    5760
gagtctcagg tttaaattca acttggtcat ggtgtgtcat ctttgatcat tgctgtctgt    5820
ggcttgctac tgttttgttt aggattttg cactgatgct catcaatgag actggcatgc     5880
catcttcctt tgcagtcctg attttttct gatttggatc atgtggttat ggccctcatg     5940
gaatgagttg ggcatgatgc cttttttca tgtctctgga ttgatgggac actttggatt     6000
ctctccagat ggccctcaat ggtccctgcc tcctcattgt taggcccctg ggcaagccct    6060
tctcatttct ggtaggccca ggaacctgtg ggggttttgt ttgtttgttt gtttcttgag    6120
tcggagtctc actctgtcac ccaggctgga gttggagtgc aatggcccga tcttggctca    6180
ctgcaacctc cacctcccag attcaagcaa ttctcctgcc tcagcctcct gagtagctgg    6240
aattacaggc acccaccgac acccctgct aattttttgta ttttttagtac agatggggtt    6300 tcacaatatt ggccaagctg gtctcgaact cctgatctca tgatctgccc ggcttggcct    6360
cccaaagtgt tgagattaca agcatgagcc accacaccca gtgaacctgt ggttttttaga    6420 agctccccat gcatgtgaat gctgtgagca tcccaggatg acagccactg tgtgttcagc     6480
tgttggaact gtgagaaagc accagtggga ccttctccag cacctgcctg ctgagttcat    6540
ggaagaggct tgttggggag atgatgccct ggctgactcc tgaaggatgg ttaggaatgc    6600
accagatgga agctgggttg gacccactct atgctgaaga acagcttgtg tggacacaag    6660
gagacacgga tatgtcattt ttgtagagcc tgaggagtgt ccaatcacac catttgctta    6720
aaacatcatg cacacttgga aaagtggact gagaccgaat gaagaagcta acagtggcca    6780
gatcagaaag ggtcttgtgt tacttcctag agatacttag attttatcct gtgggtgata    6840
ggagcagttg gagggactga agacaaggaa agaaacatgt ttcaagatct atgttttttca    6900 agacgctttt ctggtggctg agtagggaat tccctggata agtcctgccc agggtcaggc    6960
aaaacaagtt agggggttac tgaaataagg agtatgagaa atggtgtagg ttgtgctgac    7020
gttttgtaac acatctcatg atgatcttca tttccttcac taatttcctg tttcattaat    7080
tcccttccac gtgctcttct gaaatttgcc tcacattctc tgatttctct tttacctgtt    7140
ggtttcatca ccttttactt tttgctttcc tggaaacaca aatgattctg attgtgacat    7200
gtcagaatta tttgcaacat ttgcctttct gctgaaacca tgattcact gaatacacaa     7260 tttagtaaag tgtaggatgc acatgtcgtt ttcgtggtca caaccagctc tgtagcattt    7320
tataactaca ctggcagtgt gctgggaggt gtagagagaa atatttatca catgtgtggc    7380
tgacacaacc tgccaagtta ttttaggagc ctccttggaa tcccagcaag aatgctaccg    7440
gcacaatttg taatcacagc atcctgctcc atgccttggc ttcatggcat agtcacttct    7500
gcaagtctct ttccagctgt ctgttcccat gtctataaag tatgagttaa atcatcctaa    7560
cactactcat cttacaaagt tttccttgctg atgttaagag agttgggaaa gaactgtata    7620
aactgtgaag tgccatggag atgttagtgg ttactttatc aagaaataga cactctagaa    7680
```

```
tggagtagaa agccaacagt tatgattgag tcctcctcct cttcttcttt ttattaattt     7740
ataaagaaaa gaggtttaat tgactcacag ttccatatgg ctggggaggc ctcgggaaac     7800
tctcagtcat agcaggaggc aaaggggaag aaggcacctt cttcacaagg cggcaggaga     7860
gagagagctc ctgttctttt ttgtcataaa gtctacagaa gtgcttatac ttcaggacaa     7920
gggcaggcag agagaaggaa ggacattgct tcaccccagc cctcactgac gagtttgcta     7980
ggggacctca ctttgtccca gagtagggca gaactctggc cactacccat tcagaaggcc     8040
tgggctgcac tgctagttcc tcactaactc tgtgtggcct tgggcaaggt tgggcctgtg     8100
ttaacagatt atgaccctgg gctctcaagc tagaggatct aaatttgaat cctggctctg     8160
ctaaagcaat tagtgatgta aactttaatg ggtcagttaa ccttcctgtg gcttagtttg     8220
ctcatctgta aaatagggat cataacagta tcaataccac atgattgttg gacagattga     8280
atcagttaat gcaggggaag tacttagcat gacacgtatt cactatcatt tcctggagta     8340
agagctgtgt gtgagtgggt gtgagcatgt gtgaaacctt ttctctgcaa tctcagttaa     8400
gaaaccaatc cagaatttaa agttcagggc ctaaatgggt ggttatcttc tcccagttcc     8460
atcctatccc acctttgctc ttcctcccgc ccacaggagc tgttggtcct tgattgggct     8520
ggaagacctg gtggacccta agtgatctat aagaggagaa tagagaacag gaatgtctt     8580 caaaaatcta gagggacaca gaggctgaga ggcaggcagt cctgcagggt cttctgattg     8640
ggacaaggag aaccttggtc ttcacaggcc aattctggtc agtttccccc atggacagat     8700
gaggaaacag gcccaggaat atccaaggtc tcacacttcc catctgtcaa gtcttgttga     8760
ttctgttgta ttcatgtctc tcaaagggag atagagttta gggaagaaag aaggatcaac     8820
tgtgtctgat accactggga gcttaagtaa agggttcttt tacttcatag catttatccc     8880
aatttgtaat tcagtattat ttgtgtggct gtttggtgtc tctttctcct atatgagtgc     8940
tagcttcata agggcaagga ttttgattct ttaatattta gtgcttgcca catgccctga     9000
acacagcagg catacaggct aaccaacata cagtggcatg aaagtcatga aagtgagaca     9060
cctacctcct ccagtgccaa gagagcataa ccatgcacct gtcactctcc tcaacaccac     9120
ccccaagcat gaggcccaaa agcattagct aatcccctcc tccagccact aaaacttaaa     9180
ggccaggtgt ggtggctccc atctgaaatc ccagaacttc aggagacagc agcaggagga     9240
tcacttgagg ccaggagttt gagatcagcc tgggcaacat agctaggtcc catctgtact     9300
aaaaattagc tgggcgttgt tgcatgcctg tagtcccagc tactaaggag gctgaggtgg     9360
gaggatcact tgagcccagg aggtggaaac aacagtaagc tataatcaca gcactgaact     9420
ctagcctggg caacagagtg acaccctgcc tcaaaacaat tttaaaaata aataagagca     9480
aaacttagat accacgtggt caccccaaca tgcaaaatca agttttcccc tactgagaag     9540 aatgggggact tgacagctga gttacagaga gataatcttc ttcttctttt ttttttttg     9600 gtttacatcc tcaagatcat gacttgtgaa atttgaatcg aatacacatg taattccaga     9660
gcaatgttgc ctccgcatac catcagcaat tcacttggct actggaagtc aggataagct     9720
tcccagaaga gaggtaccac ttgggctacc aatataaaag gatgaaaata tcagagtgat     9780
ggtgttcttt acaacgttga gtccctggac agcctgtcca ctgatgctga tatctgagcc     9840
taatgcttct ctgaatgttg agattgaact ttgatccaat gaaactagaa cgagaaagaa     9900
gataagtctt tcattgttga taaggacatt atgtttctca tacttgtatg attattttc      9960 cttagctgta ctataattat ctgcttattt gtctctgctc tatgtgctta gggtacaaag    10020
```

```
ttgaccaaga ccaactttgg ttggaagcat agtactaaga gcacagtact gagagcacag    10080
tattgagagc acagctttaa aaaacatgat gaaggcttta atacaggaaa tgagcagggg    10140
agaggcatgt ggtggttgga tgtatcttcc ttgacacagt cagtgcagct ctcagtagtc    10200
aagtccctac atgttagaag atgttacctt ctgtggaatt aagtggcaga acttgccttc    10260
aattattttc ctttgcagaa caacaccaac tgcattagtt aggacacagt gctggctgca    10320
tttaagtccc aagcgatgat tagtctctca ctgttggtat agattcaaac caatcagacc    10380
acctcctaaa gtttgtaggg caggtaaatc ctcatcttag aataaaaatc atcttaccaa    10440
gtatgtgttt tagaggcaag aagaaaacat atttgtttct gtaagagttt tgtttaaaaa    10500
aaatataaga aaggctctcg gtttaggtga ggtaatgaag ttgttgatag ttatcagatg    10560
acactggaat ctttacttct ctgaacgtgt tctgtgcatc tctcagtgtg gaacatagaa    10620
gagggagatc ctccagcaat gccactgata tggtcagaaa ctgcatcttt ctttctccct    10680
gctgagatga gatggagtcc tttgttctag aagacccatg gtggtgccgc tgggagtaac    10740
ccttgagaca ggaacacaaa tcccaaccaa tttgtggttg cagccttgag tctcactatt    10800
tcccatagtg atgcgtagca gggaatggca ggtgcaccag agcaggagag gacctaatat    10860
ctcccttcct gttagctttt tataaagttt tattgtgatc agtagcagtt gggaagctac    10920
ttgcagtcac tgagcctcag tttctacatc tgtaaactgg ggatagtagc atggccccta    10980
cttaatgtgc tcagcaaagc cactgaaagg agacagaaat gtatctaaat taccctggac    11040
ttttatccta cctctcttgg ggattgtcac caccttccca tgtttgtcct ttttggtttg    11100
atgcttgctg tcacttcttt ccttaggtgc ctctctgtac ggctcttttta tcccagggat    11160 tccagagtta cagcacatgc ataccaccat ccaagcatgt ttatttgtct cctgcttcac    11220
taggctgtcc ccaaggaaca tgtggctccc ggcacacacc tggcacaaca ctgcacatga    11280
cattcaccca cttggccttg aatctgacaa ggaatctggc atgatgttca cccactcagg    11340
ccaggtgccg agcagccctg gaggcttagg ggccagaggg atgggaaaag gtgtctttct    11400
ggggtgagta tcagttttctg caggagggct gaatgtgaga aagaataaag agagaaggaa    11460
gcgaacaagc acagcttaaa catcgcctat ttctattgag ttttaagaac gctgtgattt    11520
tgtttgtcat gcaatccatt catcaggcca ggcagacaca gaacttgggt gtgagtgacg    11580
ataatgagct gatataattt tcacaccctc atcactgaga tctctcccat caggaatggg    11640
tcagggagct cacaggtggc agcaactgct attacaggcc tcatctctac cagctcctgg    11700
ggcctgccct cctcccatta gaaaatcctc cacttgtcaa aaaggaagcc atttgctttg    11760
aactccaatt ccaccccaa gaggctggga ccatcttact ggagtccttg atgctgtgtg    11820
acctgcagtg accactgccc catcattgct ggctgaggtg gttggggtcc atctggctat    11880
ctgggcagct gttctcttct ctcctttctc tcctgtttcc agacatgcag tatttccaga    11940 gagaagggc cactctttgg caaagaacct gtctaacttg ctatctatgg caggaccttt    12000
gaagggttca caggaagcag cacaaattga tactattcca ccaagccatc agctccatct    12060
catccatgcc ctgtctctcc tttagggggtc cccttgccaa cagaatcaca gaggaccagc    12120
ctgaaagtgc agagacagca gctgaggcac agccaagagc tctggctgta ttaatgacct    12180
aagaagtcac cagaaagtca gaagggatga catgcagagg cccagcaatc tcagctaagt    12240
caactccacc agcctttcta gttgcccact gtgtgtacag caccctggta gggaccagag    12300
ccatgacagg gaataagact agactatgcc cttgaggagc tcacctctgt tcagggaaac    12360
aggcgtggaa acacaatggt ggtaaagagg aaagaggaca ataggattgc atgaagggga    12420
```

```
tggaaggtgc ccaggggagg aaatggttac atctgtgtga ggagtttggt gaggaaagac   12480
tctaagagaa ggctctgtct gtctgggttt ggaaggatgt gtaggagtct tctaggggc    12540 acaggcacac tccaggcata ggtaaagatc tgtaggtgtg gcttgttggg atgaatttca   12600
agtattttgg aatgaggaca gccatagaga caagggcaag agagaggcga tttaatagat   12660
tttatgccaa tggctccact tgagtttctg ataagaaccc agaacccttg gactccccag   12720
taacattgat tgagttgttt atgatacctc atagaatatg aactcaaagg aggtcagtga   12780
gtggtgtgtg tgtgattctt tgccaacttc caaggtggag aagcctcttc caactgcagg   12840
cagagcacag gtggccctgc tactggctgc agctccagcc ctgcctcctt ctctagcata   12900
taaacaatcc aacagcctca ctgaatcact gctgtgcagg gcaggaaagc tccatgcaca   12960
tagcccagca aagagcaaca cag                                          12983

<210> SEQ ID NO 2
<211> LENGTH: 9715
<212> TYPE: DNA
<213> ORGANISM: Homo sapiens

<400> SEQUENCE: 2
ctggttcatc tcattgggac tggttggaca agagggtgca gcccacggag ggtgagccaa     60
agcagggtgg ggcgtcgcct cacctgggaa gcacaagggg tcgtggaatt ttctccccta    120
cccaaggaaa gccataaggg actgagcctg aggaactgtg cactctggcc cagatactgc    180
acttttccca tggtctttgc aacccgcaga ccaggagatt ccctccggtg cctatgccac    240
cagggccctg ggtttcaagc acaaaactgg gcagccattt gggcagacac cgaactagct    300
gcaggagttt tttttttttt tttccatacc ccattggcac ctggaacgcc agtgagacag    360
aaccgttcac tcccctggaa agggggctga aaccagggat ccaagtggtc tggctcggtg    420
ggccccaccc ccatggagcc cagcaaacaa agattcactt ggcttgaaat tcttgctgcc    480
agcacagcag cagtctgaga ttgacctggg accctcgaac ttggttgggt gctgtggggg    540
ggcatcttcc attgctgagg cttgagtagg tggttttacc ttcgcggtgt aaacaaagct    600
gctgggaagt ttgaactggg tggagctcac cacagctcag taaggccact gtggccagac    660
tgcctctctg gatttctcct ctctgggaag gatatctctg aaaaaaaggc agcagcccca    720
gtcagggact tatagatgaa accccatctc ccctgggaca gagcccctcg gggaagaggt    780
ggcttccacc attgtggaag actgtgtggc aattcctcac ggatttagaa ctagagatac    840
catttgaccc agcaatccca ttactgggtg tatacccata ggattataaa tcattctact    900
ataaagacac atgcacactt atgtttattg taacactatt tacaatagca atgacctgga    960
accaatccaa aagcccatca atgatagact gaataaagaa aatgtggcac atatacactg   1020
tggaatacta tgcagccata aaaaggatg agttcatgtc ctttgcagag acatggatga   1080
agctggaaac catcattctc agcaaactag cacaataaca gaaaaccaaa cactgcatgt   1140
tgtcactcat aagtgggagt taaacaatga gaacacatgg acacagggag gggaacgtca   1200
cacactgggg catgtcgggg agtggggggcc tacgggaggg atagcattag cagaaatacc   1260
taatgtaggt gacgggttga tgggtgcagc aaaccaccat ggcacatata cacctatgta   1320
ataaaactgc acgttctgca catgtacccc agaacttaaa gtataattaa taataataat   1380
aatttctggg catgtaagta gctgtctttc aggttctact ttgatacata ttctgagaga   1440
attaaacctg tcaaagaaac cttgactttc aatggcaggc actggaattg accctaataa   1500
```

```
tgtgttttgg ggtaagccta ctcatattct caacctgtct gcagtagtcg ttagaatctg   1560
aacttcctga agttcatgtg caaagttgag ttaattgttt aatattcaac aaggattatg   1620
ccagtaagat ggtaggaaaa tattagatat gtgtcatcac tgctggtatt atttaaactg   1680
caacatattt tagctggctg ctgatctcag ccaccatgcc tgcattttat ctctgtctcg   1740
tggtctgcaa ccttggaagc tttgaactta gctcatagaa tcctgggcat caagaacatg   1800
tggttctaat ggctagatag ggaatgagag taaaaggatt ttgcccacgg tcacgtgagt   1860
aaacaacaga tttggagggg tctggactac tgtgatgact tcattctgac aatatgttcc   1920
agttgtcctt tcatttcctc ctaatcacat gtctggtctg atctggctgt ttcccacctt   1980
ccaattcctg ccttctccaa tgctcccttc cgtaggtcac tctgtggctc agagaccctg   2040
cttagcaagc gcccaacctt tcaattattt gttcagtaaa acttgaactc atgtctcccc   2100
ttcttgataa aaagaaaata cgttatgtaa tgtcgggtta ctctataact cttgtcctgt   2160
ctctcggcaa ctactgaact aactgttttc atattgagca aacgtttatg gaaggactgc   2220
caagagtcag gtactaggct tggtaatatt ccccgttctc tctagtcaaa gccaacacca   2280
gccagacttg cagatctagg tcccaagccc actgcagatc acaggccagg gtctggtctc   2340
ctctgagctc ctttgggagg gaaagacaga attattaaca cccatttgt agattaggca    2400 actgaggctg aggaagttta ataaactcag acagggcctg cacgtcagtc atattccaag   2460
gatccctact cactgtcttc tctctacaga acgagatgtc tctggagtcc atagaaagcc   2520
caggagcctg gctgggcacg gtggctcctg cctgtaatcc cagcactttg ggaggccgag   2580
gcaggcagat cacctgagct caggagttca agaccagcct gggcaacatg gcaaaacccc   2640
atctctacta aaaatacaaa aaattagctg ggcgtggtgg tgcatgcctc taatcccagc   2700
tacttgggag gctgaggcac aagaattgct tgagcccagg aggcagcagt tgcagtgagc   2760
tgagattgtg ccagtgcact ccagcctggg caacagagca agattccatt tcaaaaacaa   2820
aaacaaacac aaacaaacaa acaaaaatag aaagcccagg gaccacctgc gtcaggttcc   2880
cagccacacc ttttttcttgt cctcctctgt ctctggcatc ttctcacagg ttcctaattg   2940
tttgtggttg cacaaattca aaatcccaga aaaattacca cttcacaccc actcagatgg   3000
ctattttttt tttgaaggaa gataacaagt gttgacaaga acatggagaa attggaattc   3060
tcacccattg ctggtgagaa tgtaatacgg tgctgctgct atggaaaaca gcttggagtt   3120
tcctcaaaaa gttcaacaga atttcaatgt gacccagcaa ttcccctcta agttatagat   3180
ctgagaggat taaaaacagt tactaaaata cacggactca catatttcta acagtccaat   3240
tcacaagggc caaaaggtgc taatagccca catgtccatc gatggatgga taaataaatt   3300
gtggtctatc catacaatgg aatattattc ggccataaat ggaatgaagt actgacgcat   3360
gctacagaat ggatgaaccg caaaaaaaat ggatgaacac atgctacaga atggatagcc   3420
tcactttact atgaagtgaa ggccagaaac gaagtccata tattgcatca tacaaaatat   3480
ccagaagagg gaagcccaca gagacagaat gtgcaatggt ggatgccagg gtctggggag   3540 agggagagt ggggagaaac tgctcaactg gtacaggctt tattttggaa tgatgggaac    3600
attttgcaac tagatagagg tagtgattgc agaacacaga atgtactgaa ttccactgat   3660
ttttttcacc ttaaaatggt taattttcag tcctgagatt ggataatcat aaaaaaatgg   3720 ttaatttttat gttatgtgaa tttcatccct atacatattt taaacctcag aaatatacac   3780
tagcaggcat ggaacaggtc actgtggtgc ctgccaagcc cggtgatgtt atctggggtc   3840
cccggccagc cttaagcctc ttgctgaccg gtggagggca gaacctttgc cctaaaagta   3900
```

```
taatatccac atgctggcat gattcctggc cagatggctt ctttattagc agtaattgaa    3960
actgcctcga tacagacact gtaccttgca accaaaaaat gactcaacaa tgataataag    4020
ggttaagctg ggccttttctc tctttgccag ttaaattata tttattatag cttgacatga    4080
aaaacaaagc aactccaaca ggtatcacaa gggcaaagga catgaacatt ttatcaaaga    4140
agaaatgcag ctgtcaaaaa tacagaaata ttcaaccttg ttcataataa agtggctggg    4200
ctcagtggtt catgcctgta atcccagtgc tttgcaaggc tgagacagga ggatcatttg    4260
aagccagaag ttcaagacca tcctaggcaa gtcagttcaa taccagactt catgtctaca    4320
aaacatcaaa aaattagcca ggcatggtga tgcatgcctg ttgtcccagc tactcaggag    4380
gctgaggcag gagaattgct tgagcctggg aggctgcggt ggcggtgagc catgattgtg    4440
ccattgtact ccagcctggg caatgcagca agactgtcta ataacaaaa ataatagtaa    4500 agaaaaggat tgggatgcca tttacttgcg tattcaatac acagagttaa aagtaatttc    4560
tacgttttct atttttttat tactaaaaaa agctggacca ttctcacagc ctgaaatgct    4620
tctcactttc ccttcttctg tccaaacact tctctatgat aatgcaaaca gtcactcctt    4680
taggaagact tcaccccagg tagttccaga tccccttatc tctgccttcc cagaactcct    4740
ggtgtctctc cagttccctc cgtgtggtga agtaccctac ctagggtttc agtatggctc    4800
tgtctgcaaa ggtcttgttc acaccttccc ttatggttct gttgccctgt gttgtgtcat    4860
agcacagggc acagtggaga acccattcac actgatagag agggcccat ggtcctggag    4920 ataaccatgt aaccgatcag aataaggcat tgagggctgg gtgtcaggcg tgggctgcac    4980
ttgggtgggc aggtcccctg gaaagtcact gggtttggca agcttcctag taacatgtct    5040
ctctggggtc ccccttggaa cttcatgcaa aaatgctggt tgctggttta ttctagagag    5100
atggttcatt cctttcattt gattatcaaa gaaactcatg tcccaattaa aggtcataaa    5160
gcccagtttg taaactgaga tgatctcagc tgaatgaact tgctgaccct ctgctttcct    5220
ccagcctctc ggtgcccttg aaatcatgtc ggttcaagca gcctcatgag gcattacaaa    5280
gtttaattat ttcagtgatt attaaaccctt gtcctgtgtt gacccaggt gaatcacaag    5340 ctgaacttct gacaagaaca agctatcata ttcttttcaa ttacagaaaa aagtaagtta    5400
attgatagga tttttttttgt ttaaaaaaaa tgttactagt tttgaaaagg taatatgtgc    5460
acatggtaaa cactaagaag gtataagagc ataatgcttt tatactacta agaataatgt    5520
tttctctaag ttttttttttgg tagatgcttt catcagatta agaaaattcc ctgctattag    5580
ttgttgaagg tttttatatc ataaatgaaa gttgaatatt attatcatat attattaata    5640
tattgttatt gaactatcaa agccttttcc taaaaccatt gagatgatct tataaccatt    5700
ctcctttaac ctgttgacga gatcattggt atttatacta tttctctgtt aaccattctt    5760
gagtctcagg tttaaattca acttggtcat ggtgtgtcat ctttgatcat tgctgtctgt    5820
ggcttgctac tgttttgttt aggattttttg cactgatgct catcaatgag actggcatgc    5880
catcttcctt tgcagtcctg atttttttct gatttggatc atgtggttat ggccctcatg    5940
gaatgagttg ggcatgatgc cttttttttca tgtctctgga ttgatgggac actttggatt    6000
ctctccagat ggccctcaat ggtccctgcc tcctcattgt taggcccctg ggcaagccct    6060
tctcatttct ggtaggccca ggaacctgtg ggggttttgt ttgtttgttt gtttcttgag    6120
tcggagtctc actctgtcac ccaggctgga gttggagtgc aatggcccga tcttggctca    6180
ctgcaacctc cacctcccag attcaagcaa ttctcctgcc tcagcctcct gagtagctgg    6240
```

-continued

```
aattacaggc acccaccgac acaccctgct aattttttgta tttttagtac agatggggtt    6300
tcacaatatt ggccaagctg gtctcgaact cctgatctca tgatctgccc ggcttggcct    6360
cccaaagtgt tgagattaca agcatgagcc accacaccca gtgaacctgt ggttttttaga   6420
agctccccat gcatgtgaat gctgtgagca tcccaggatg acagccactg tgtgttcagc    6480
tgttggaact gtgagaaagc accagtggga ccttctccag cacctgcctg ctgagttcat    6540
ggaagaggct tgttggggag atgatgccct ggctgactcc tgaaggatgg ttaggaatgc    6600
accagatgga agctgggttg gacccactct atgctgaaga acagcttgtg tggacacaag    6660
gagacacgga tatgtcattt ttgtagagcc tgaggagtgt ccaatcacac catttgctta    6720
aaacatcatg cacacttgga aaagtggact gagaccgaat gaagaagcta acagtggcca    6780
gatcagaaag ggtcttgtgt tacttcctag agatacttag atttttatcct gtgggtgata   6840
ggagcagttg gagggactga agacaaggaa agaaacatgt ttcaagatct atgttttttca  6900
agacgctttt ctggtggctg agtagggaat tccctggata agtcctgccc agggtcaggc    6960
aaaacaagtt agggggttac tgaaataagg agtatgagaa atggtgtagg ttgtgctgac    7020
gttttgtaac acatctcatg atgatcttca ttttccttcac taatttcctg tttcattaat   7080
tcccttccac gtgctcttct gaaatttgcc tcacattctc tgatttctct tttacctgtt    7140
ggtttcatca cctttttactt tttgctttcc tggaaacaca aatgattctg attgtgacat   7200
gtcagaatta tttgcaacat ttgcctttct gctgaaacca tgagttcact gaatacacaa    7260
tttagtaaag tgtaggatgc acatgtcgtt ttcgtggtca caaccagctc tgtagcattt    7320
tataactaca ctggcagtgt gctgggaggt gtagagagaa atatttatca catgtgtggc    7380
tgacacaacc tgccaagtta ttttaggagc ctccttggaa tcccagcaag aatgctaccg    7440
gcacaatttg taatcacagc atcctgctcc atgccttggc ttcatggcat agtcacttct    7500
gcaagtctct ttccagctgt ctgttcccat gtctataaag tatgagttaa atcatcctaa    7560
cactactcat cttacaaagt tttcttgctg atgttaagag agttgggaaa gaactgtata    7620
aactgtgaag tgccatggag atgttagtgg ttactttatc aagaaataga cactctagaa    7680
tggagtagaa agccaacagt tatgattgag tcctcctcct cttcttcttt ttattaattt    7740
ataaagaaaa gaggtttaat tgactcacag ttccatatgg ctggggaggc ctcgggaaac    7800
tctcagtcat agcaggaggc aaaggggaag aaggcacctt cttcacaagg cggcaggaga    7860
gagagagctc ctgttctttt ttgtcataaa gtctacagaa gtgcttatac ttcaggacaa    7920
gggcaggcag agagaaggaa ggacattgct tcaccccagc cctcactgac gagtttgcta    7980
ggggacctca ctttgtccca gagtagggca gaactctggc cactacccat tcagaaggcc    8040
tgggctgcac tgctagttcc tcactaactc tgtgtggcct tgggcaaggt tgggcctgtg    8100
ttaacagatt atgaccctgg gctctcaagc tagaggatct aaatttgaat cctggctctg    8160
ctaaagcaat tagtgatgta aactttaatg ggtcagttaa ccttcctgtg gcttagtttg    8220
ctcatctgta aaatagggat cataacagta tcaataccac atgattgttg gacagattga    8280
atcagttaat gcaggggaag tacttagcat gacacgtatt cactatcatt tcctggagta    8340
agagctgtgt gtgagtgggt gtgagcatgt gtgaaacctt ttctctgcaa tctcagttaa    8400
gaaaccaatc cagaatttaa agttcagggc ctaaatgggg ggttatcttc tcccagttcc    8460
atcctatccc acctttgctc ttcctcccgc ccacaggagc tgttggtcct tgattgggct    8520
ggaagacctg gtgaccccta agtgatctat aagaggagaa tagagaacag ggaatgtctt    8580
caaaaatcta gagggacaca gaggctgaga ggcaggcagt cctgcagggt cttctgattg    8640
```

```
ggacaaggag aaccttggtc ttcacaggcc aattctggtc agtttccccc atggacagat    8700
gaggaaacag gcccaggaat atccaaggtc tcacacttcc catctgtcaa gtcttgttga    8760
ttctgttgta ttcatgtctc tcaaagggag atagagttta gggaagaaag aaggatcaac    8820
tgtgtctgat accactggga gcttaagtaa agggttcttt tacttcatag catttatccc    8880
aatttgtaat tcagtattat ttgtgtggct gtttggtgtc tctttctcct atatgagtgc    8940
tagcttcata agggcaagga ttttgattct ttaatattta gtgcttgcca catgccctga    9000
acacagcagg catacaggct aaccaacata cagtggcatg aaagtcatga aagtgagaca    9060
cctacctcct ccagtgccaa gagagcataa ccatgcacct gtcactctcc tcaacaccac    9120
ccccaagcat gaggcccaaa agcattagct aatcccctcc tccagccact aaaacttaaa    9180
ggccaggtgt ggtggctccc atctgaaatc ccagaacttc aggagacagc agcaggagga    9240
tcacttgagg ccaggagttt gagatcagcc tgggcaacat agctaggtcc catctgtact    9300
aaaaattagc tgggcgttgt tgcatgcctg tagtcccagc tactaaggag gctgaggtgg    9360
gaggatcact tgagcccagg aggtggaaac aacagtaagc tataatcaca gcactgaact    9420
ctagcctggg caacagagtg acaccctgcc tcaaaacaat tttaaaaata aataagagca    9480
aaacttagat accacgtggt caccccaaca tgcaaaatca agttttcccc tactgagaag    9540
aatggggact tgacagctga gttacagaga gataatcttc ttcttctttt ttttttttg     9600 gtttacatcc tcaagatcat gacttgtgaa atttgaatcg aatacacatg taattccaga    9660
gcaatgttgc ctccgcatac catcagcaat tcacttggct actggaagtc aggat         9715

<210> SEQ ID NO 3
<211> LENGTH: 632
<212> TYPE: DNA
<213> ORGANISM: Homo sapiens

<400> SEQUENCE: 3
tctagagaga tggttcattc ctttcatttg attatcaaag aaactcatgt cccaattaaa      60
ggtcataaag cccagtttgt aaactgagat gatctcagct gaatgaactt gctgaccctc     120
tgctttcctc cagcctctcg gtgcccttga atcatgtcg gttcaagcag cctcatgagg      180
cattacaaag tttaattatt tcagtgatta ttaaaccttg tcctgtgttg accccaggtg     240
aatcacaagc tgaacttctg acaagaacaa gctatcatat tcttttcaat tacagaaaaa     300
agtaagttaa ttgataggat tttttttgtt taaaaaaat gttactagtt tttgaaaagg      360
taatatgttg cacatggtaa acactaagaa ggtataagag cataatgctt ttatactact     420
aagaataatg ttttctctaa gttttttttg gtagatgctt tcatcagatt aagaaaattc     480
cctgctatta gttgttgaag gtttttatat cataaatgaa agttgaatat tattatcata     540
tattattaat atattgttat tgaactatca aagccttttc ctaaaaccat tgagatgatc     600
ttataaccat tctcctttaa cctgttgacg ag                                   632

<210> SEQ ID NO 4
<211> LENGTH: 11186
<212> TYPE: DNA
<213> ORGANISM: Homo sapiens

<400> SEQUENCE: 4
ggatccagtt tcagctttct acatatggct agccagtttt cccagcacca tttattaaat      60
agggaatcct ttccccattg cttgtttttg tcaggtttgt caaagatcag atggttgtag     120
```

-continued

```
atgtgtggtg tttgttctga ggcctctgtt ctgttccatt ggtccatatc cctgttttgg    180
tactagtacc atgctctttt ggttactgta gccttgtagt atagtttgaa gtcaggtagc    240
gtgattcctc cagctttgct ctttttgctt aggattgtct tgggaatgtg ggctcttttt    300
tggttccata tgaaatttaa agtagttttt tttccaattc tatgaagaaa gtcattggta    360
acttgatggg gatggcattg aatctataaa ttaccttggg aagtatggcc attttcacga    420
tattgattct tcctatccat gagcatggaa cattcttcca tttgtttgtg tcctctttga    480 tttttgttgag cagtggtttg tagttctcct tgaagaagtc cttcacctcc ctttaatttg    540
gattactaga tattttattc tcttagtaac aattgcaaat gggagttcac tcatgatttg    600
gctctctttc tgttattggt gtataggaat gcttgtgatt tttgcgcatt aatttttgtat    660 cctgagactt gctgaagtt gcttatcagc ttaaaaggat tttgggctga gacgatgggg    720
ttttctaaat atacaatcat ggcatctgca aacaggaaca atttgacttc ctcttttcct    780
aattgaatac cctttatttc tttttcttgc ctgattgccc tggccagaac ttccaatact    840
atgttgaata agagtcatga gtgagggcat cgttgtcttg tgctggtttc aaagttttg    900 cccattcagt atgattttgg ctgtggtttt gccataaata gctcttatta ttttgagata    960
cgttccacca atacctactt tattgagagt ttttagcagg aagggctgtt gaattttgtc    1020
gaaggccttt tctacatcta ttgagacaat tatgtggttt tttaatcgtt gattctgttt    1080
atgtgatgga ttacatttat taatttgcat atgttgaacc agccttgcat cccagggatg    1140
aagcccactt gattgtagtg gataagcttt ttgatgtgct gctggattca gtttgccagt    1200
attttattga ggattttggc atcaatgttc atcagggata ttggtctaaa attctctttt    1260
tttgttgtgt ctctgccagg cttggtatc aggatgatgc aggcctcaga aactgagtta    1320
gggaggattc cctcattttc tattgattgg aatagtttca gaaagaatgg taccagctac    1380
tctttgtacc tctggtagaa ttcagctgtg aatccatctg gtcctggact ttttggttgg    1440
taggctatta attattgcct caattttagg gcctgttatt ggtctattca gacattcaac    1500
ttcttcccgg tttggtcttg ggagggttta tgtgtccagg aatttatcca tttcttctag    1560
attttctagt ttatttgtgt agaggtgttt atagtattgt ctgatggtag tttgtatttc    1620
tgtgagatcg gtggtgatat cccctttatc atttttatt gcatctattt aattcttctc    1680
tcttttcttc tttattattc tggctggcgg tctgtcaatt ttttgatct tttcaaaaaa    1740 ccagctcctg ggtttcactg attatttgaa gggttttttg tgtctctatt tctttcagtt    1800
ctcctgtgat cttagttatt tcttgccttc tgctagcttt tgaatgtgtt tgctcttcct    1860
tctctagttc tttgaattgt gatgttacag tgttgatttt agatctttcc tgctttctct    1920
tgtggtcatt tagtgctata aatttccctc tacacattgg tttacatgtg tctcagagat    1980
tctggtatgt tgtgtctttg ttctcattca tttcaagaac atctttactt ctgccttcat    2040
tttgttattt gcccagtagt cattcaggag caggttgttc agtcttcatg tagttgtgtg    2100
gttttgagtg agtttcttaa tcctgagttc taatttgatt gcactgttgt ctgagagaca    2160
gtttgttgtg atttccattc ttttacattt actgagcatg cttatgtcc cattatgtgg    2220 tcaattttag aataagtgtg atgtgatgct gagaagaatg tatattctgt tgatttgggg    2280
tgtggagttc tgtagatgtc tattcagtcc actgggtgca gagctgagtg gacatgaaca    2340
ttttatcaaa gaagaaacac agctatcaaa aatccagaaa tattgaacct tgttaataat    2400
aaagtggctg gcctctggtt cattcctgta atctcagtcc tttgaaaggc tgagaaagga    2460
ggatcacttg aggccacaag ttcaagacca tcctagacaa gtcagttcaa gaccagactt    2520
```

```
catgtctaca aaacatcaaa aaattagcca ggcatggtga tgcatgcctg tcatcccagc   2580
tactcaggag gctgaggcag gaggattgct tgagcctggg agattgaagt ggcagtgagc   2640
catgattgtg ccattgcact ccagcctggg caatgcatca agactctgtc taaacaataa   2700
taataataat agtaatagta ataataataa taataaagaa aacggttggg acgccattcc   2760
ttacttattc aatacacaaa gttaaaagca atttctactt tctctatttt tttattacta   2820
aaaaaagctg aaccattctc acagcctgaa atgcttctca ccttcccctc ttctatacaa   2880
acacttctct gttgatgata atgcagacag tctctccttt aggaatactt cacaccaggt   2940
agttccagat ccccttatct ctgccttccc agagctcctg gtgtctcccc agttccctct   3000
gtgtggtgaa gtaccccac cttgggtctc agcatgactc gttctttgaa ggtcttgttc   3060 acatttccc ttatggttct gttccctgt gttgtgtcac agcactgggc agagtggaca   3120
acccattcac accgatagag agggcccat ggttctggag ataaccatgt aactgatcag   3180
aatagggcat tgagggctgg gtgtcaggca tgggctgcac ttgggtgggc aggccccctg   3240
gaaagtcaca ggatttggca agcttcctag taacatctct ccctgggtc ctcttggaac   3300 ttcatgcccg atgctggatg ctggtttatt ctcgagagat ggttcattcc aataatcaat   3360
gaaactcatg tcccaactaa agttcataaa ctccagtttg taaactgaga taatctcagc   3420
tgaatgaact tgctgaccct ctgctttccc ccagcctctc agtgcccttg aaatcatgtc   3480
agttcaagca gccccatgag gcattacaat gtttagttat ttcagtgttt attaaacctt   3540
gccctatgct gaccccaggt gaatcacaag ctggacttct gacaaggaca agctatgata   3600 ttctttttcaa ttacagaaaa agtaagttaa ctgataggat ttttttaaaga tgttactagt   3660 tttgaaaagg taatttgtgc acatggtaaa caagaaggta taagaggata atgcttttat   3720
actgctgaga ataatgtttt ctctaatttt ttttggtaga tgctttcatc agattaataa   3780
aattcactgc tgttagttgt tgaaggtttt ttatatcatg aatgggagtt gaatattatc   3840
atgtattatt aatatattat tattgaacta gcaaaggctc ttcctaaaac aattgagatg   3900
atcttataat cgttctcctt taatctgttg atgagatcat tggtatttat acttttctc    3960 tgttaactat tcttgagtct caggtttaaa ttcaacttgg tcatggtgta tcatctttga   4020
acactcctgt ctctggcttg ctactattgt gttcagcatt tttgcactga tgccgatgaa   4080
tgagactggc atgtcatctt cctttgcggt cctgattttt ttcagatttg gatcatgtgg   4140
ccctcattga atgagttggg tgtgatgcct tcttttcat gtatctggat tgatgggaca   4200
ctttggagtc tctccagatg gccctcaatg gtccctgcct cctcattgtt aggctcctag   4260
gcaacccttt ctcatttctg gtaggcccag gaacctgtgg gttttatgtt tgtttgtttg   4320
tttgtttgtt tgttttttga gttggagtcc tgctttgtct cccaggctgg ggttggagtg   4380
caatggcctg atctcggccc actgcaacct ccacctcctg ggttcaagtg attctcctgc   4440
ctcagccttc tgtgtagctg ggattacagg catccaccac cactcctggc taattttttgt   4500 attttttagta gagacggggt tttacaatat aggccattgt gatctcttgg acaggctagt   4560
ctcaaattcc tgacctcatg atctgcctgc ctcagcctcc caaagtgctg agattacagt   4620
tttgtgcctc cacacacagt gaatctgtgg ttttttaaaag ctcctcatgc atgtgaattc   4680
tgtgagcatc ccgggatgac agccactgtg tgtccagctg ttaaaactgt gagaaagcac   4740
cagcgggacc ctctccagca tttgcttgct gtggtcatga agaggcttg ttggggagat   4800 gatgccctgg ttgactcctg aaggatggtt aggaatgcac cagatggaag ctgggttgga   4860
```

-continued

```
cccagtctat gctaaagaac agcttgtgtg gacacaagga gacacgaaca catcattttt    4920
gcagagcctg gggagtagcc aatcgcacca tttgcttaaa acaccgtgta cagttggaga    4980
agtggactga gacaggctga agaagctaac agtggccaga tgagaaaggg tcttgtgtta    5040
cttcctagat atacttagat tttatcctgt gagtgatagg aacagttgca gggactgaag    5100
ccaaggaagc atgctttaag attccatgtt ttttgagatg ctgtctggtg gctgagtagg    5160
gaattccctg gataagtact gcccagggta ggcaaaagaa gctaggaggt tactgaaata    5220
aggagtatga gaaatggtgt aggttttgct gatgttttgt aacacatctc atgacaatct    5280
tcatttcctt caccaatttc ctgtttcatt aattcccttc cacgtgctct tctgaaatt     5340
gcctcatatt ctttgatttc tcttttacat gttggtttca tcaccttta cttttgctt     5400
tcctggaaac acaaatgatt ctgattgtga catgtcagaa ttatttgcaa cattcccctt    5460
tctgctgaaa catgagctca ctgaatacac aatttagtaa agtgtaggat gcacatgttg    5520
ttttcatggt cataaccagc tctgtagcat tttataacta cactggcagt gtgctgggag    5580
gtgtagagag aaatatttat ctcatgtgtg gctgacacaa cctgccaagt tgttttagga    5640
gccttcttgg aatcccagca agaacaccac tgatgcaatt tgaaatcaca atgtcctgct    5700
ccatgccctg gcttcatggc ttagtcacgt ctgaagtcta tttctaacta tctgtttcca    5760
catctataaa gtatgagtta aatcatccta atactactca tcttacaaag ttttcttgct    5820
gatattagga gagttgggaa agaactgtat aaattatgaa gtgccatgga gatgttggtg    5880
gttactttat caagaaatag acactccaga atagagtaga aagaaaacag ttatgattaa    5940
gtcctcctcc tcttctttt ttttaattta caaagaaagg tttaattgag tcacagttcc     6000
atatggttgg ggaggctcag aaaacttgca atcatggcag ttggcaaagt ggaagaaggc    6060
accttcttca caaggtggca ggagagagag agctcctctt ctttttgtt gtaaagtcta     6120
cagaagtgca tatacttcag ggcaagggca ggcagggaga agaaaggaca ttgcttcacc    6180
ccagtcctca ctgacaagtt tgctttggga cttcattttg tcccagcata tgggacagag    6240
ctctggccac tacccattca gaaggcctga gctgcattgc tagttcccca ctaactctgt    6300
gtgtccttgg gcaaggctgg gcttatgtca aaagattatg accctgggct ctccagctac    6360
agaatctaca tatgaatcct ggctctgcta gagcaattag tgacgtaacc ttggatgggt    6420
cagttaacct tcctgtggct tagtttgctc atctgtaaaa tagggatcat aacaacatca    6480
ataccatggg ttgttagaca gattgaatca gttaatgcag ggtaaatact tagcatgaca    6540
cgtattcact atcatttcct tgagtaaaag ctgagtgtga gtgggtgtga aatgtgtga    6600
aacccttca ctgcaatctc agttaagaaa cccatccata atttaaagtt cagggcctaa    6660
atgggtggtt atcttctccc agttgcatcc tatcccacct ttgctcttct cctgcccgta    6720
ggagctgttg gtctttgatt gggctggaag acctggtgga ccctaagtga tctataagag    6780
aatgagaata gaggacaggg aatgtcttca aaactcctag agggacacag aggctgagag    6840
gcaggcagtc ctgcaggggt cttctgattg ggacaaggag gaccttggtc ttcataggcc    6900
aattctggtc aatttccccc atggacagat gaggaaacag atccaggaat atccaaggtc    6960
tcacacttcc catctgtcaa gtcttgttga ttctgttgta ttcatgtctt tcaaagagag    7020
agagagttta aggaaagaaa gaaggatcaa ctgtgtctga tatcactggg agcttaagta    7080
aagggttctt ttacttcata gcattttttcc caatttgtaa ttcagtatta tttttgtcac    7140
tgtttagtat ctctttgtcc tattagagag atagcttcat caggacaagg attttgattc    7200
tttaatattt agtgcttgcc acatgccctg aacacagcag gcatacagac taaccaacat    7260
```

```
acagtggcat cgaagtgaga cacctacctc ctccagtgcc tagagtacat gtccatggac    7320
ctgtcactct cctcaacacc acccctaagc atgaggcccg aaagcattgc taatcccctc    7380
ctccagccac caaaacttaa aggccaggtg tggtggctcc tatctgaaat ctcagaactt    7440
taggagacag cagcaggagg atcacttgag gccaggaatt tgagacgagc ctgggcaaca    7500
tagctagaca ccatctgtac taaaaattag ctgggcatgg tggtatacct gtagtaccag    7560
ctactaagga ggctgaggta ggaggatcac ttgaacccag gaggtggaag ctacagtgag    7620
ctataaccac agcactgaac tccagcctga gcaacagagt gagaccctgc ctcaaaacaa    7680
tttcaaaaat aaataaataa aaacaaaact tagataccac gtggtcaccc caacatgcaa    7740
aatcaagttt tccctactg agaagaatgg ggacttgaga gctgagttac agagagataa    7800
tctgcctttt ttttttttt tttggtttac atcctcaaga tcatgacctg tgaaatttga    7860
atctaataca caaatcattc cagagcaatg ttgcttctgc ctaccacgag taattcactt    7920
ggccactgga agtcagaaca agcttcccag aagagaggta ccacttggac taccaatata    7980
aaaggatgaa aatatcggag tgaaggtgtt ccttgcatca ctgagtccct ggacagcctg    8040
tccactcatg ctgatatctg agcctaatgc ttctctgaat gttgagattt aactttgatc    8100
caatgaaacc agaccaagaa agaagaaacg tcttttcattg ttgataagga catgattttt    8160
ctcacaattt tatgattatt tttccttagc tgtcctataa ttatctgctt atttgtctct    8220
tctccatgtg cttagggtac aaagttgacc aagaccaaga ataatgtctg ggagcacaat    8280
actgacagca cagcttttaaa aacatgatga atgctttaat acaggaaatg agtaggggag    8340
aggcaagtgg tgcttgggtg ttcttccaat gcatagtatc ttccttgaca cagtcagtgc    8400
agctctcagt aggcaagtcc ctacatgtta gaagatgtta cttttctgtgg aattaggtgg    8460
cagaacatgc cttcaattat tttcctttgc agaacaacac caatttcatt agttaggaca    8520
gagtgctggc tgcatttgaa ttccaagcaa cgattagtct atcactgttg gtatagattc    8580
caaccagtca caccacctcc tgaagtttgt tgggcaggta aatcttcatc ttagaataaa    8640
aatcatctta gccaagtaag tgttttagag gaaagaagaa aacataatcg tttccataag    8700
agttttgttt ctaaaaaaat aagaaaggct ctttgtttag gtgagctaat gaagttgttg    8760
atagttatca gatgacactg gaatctttac ttgccagaat gtgttctgtg cacctctcgg    8820
tgtggcaaca tagagaggga gatcctccag caatgccatt gatatggtca gaaactgcat    8880
cttctcttct ccctgctgag atggggtcct tgttctaga aaaccccaggg ggtgccactg    8940
ggagtaaccc ttgagacagg aacacgaatc tcaaccaatt tctggttgca gccttgagtc    9000
ttactatttg ccatagtgat gcttagcaag gaatggcagg tgcaccagag cagcaggaga    9060
cctaatatct cccttcctgt taactttta taatatttta ttgtgatcag tatcagttgg    9120
gaagctactt gcagtcactg agcctcagtt tctacatctg taaactgggg atagtagcat    9180
ggccctattt aatgtgctca gcgaagccac tgaaaggaga cagaaatgta ccagaattcc    9240
ctggactttt atcctacttc tcctgggggat tgtcacccac ctacccgtgt ctgtcctttg    9300
ttgctttgac gctgtcactt cttttcttag gtacctctct gtagggctcc attattccag    9360
ggattccaga gttacagcac atgcatacct ccatccaagc atgtttattt gtctcctgct    9420
tcactaggct gtccccaagg aacatgtggc tcccggcaca tacctggcac aacactgcac    9480
atgacattca cccacttggc cttgaatctg acaaggaatc tggcatgatg ttcacctgct    9540
gaggccaggt gccgagcagc cctggaggct taggggccag agggatggga aaaggtgtct    9600
```

```
ttctggggtg agtatcagtt tctgcaggag tgctgaacct gagaaagaat aaagagagaa    9660
ggaagtgaac aagcacagct taaacatcat ctgtttctac tgagttttaa caactctgag    9720
attttgtttg tcatggaatc catttctcag gccaagcaga cacagaactt gggtgtgagt    9780
gatgataatg agctgatata attttcacac cctcatcact gagatctctc ccatcaggaa    9840
tgggtcacag ggctcacagg tggcagcaac tgttattaca ggcctcatct ctaccagctc    9900
ctggcacctg ctctcctctc attagaaaat cctccacttg tcaaaaagga agccatttgc    9960
tttgaattcc aattccaccc tcaagaggct gggaccacct cattggagtc cttgatgctg   10020
tgtgacctgc agtgaccact gccccattgt tgctggctga ggtggtttgg gtcaacctgg   10080
ccatctgggc agctgttctc ttctcttctt tctccctac tgtttccaga catgcagtat    10140
ttccagagag aaggggccac tctttggcaa agaacctgtc taactttcta tctacgcag    10200 gacttttgaa agctacagag gaagaagcac aaattgatgc tattccacta agccatcagc   10260
tccatctcat ccatgccatg tctcttttt aggggtcctc ttgccaacag aatcacagag   10320
gacaaatctg aaagtgcaga gacagcagct gaggcacagc caagagctct ggctgtatta   10380
atgacctaag aagatggagt ggtcaccaga agtcagagg aagtgacaca caggggccca    10440
gcaatctcag ccaagtcaac tccaccagcc tttctggtcc ccactgtgtg tacagcaccc   10500
tgatagggac cagagccatg agagtgagta agaccagact atgcccttga ggagctcacc   10560
tctgctaagg gaaacaggcc tggaaacaca caatggtggt aaagaggaaa gaagacaata   10620
gaactgcatg aaggggatgg aaagtgccca ggggaggaaa tggttacttc tgtgtgaggg   10680
ggttggtgag gaaagactct aagagaaggc tctgtctggc tgggtatgaa aggatgtgta   10740
ggagtcttct aggggcaca ggcacactcc aggcataggt aaagatctgt aggcatggct    10800 tgtttgggatg agtttcaagt attctggaat gaggacagcc atagagacaa gaggagagtt   10860
aatagatttt atgccaatgg ctccacttga gtttgtgata agaacccaga acccttggac   10920
tccccagtaa cattgattga gttgtgtatg attctacata gaatattaac tcaatggagg   10980
tcagtgagtg gtgtgtgtgt gattatttgc caactgccga ggtggagaag cctcttccga   11040
ctgcaggcag agcacggggg ccctgctact ggctgcagct ccagccctgc ctccttctcc   11100
agcatataaa caatccaaca gcctcactga atcactgctg tgcagggcag gaaagctcca   11160
cacacacagc ccagcaaaca gcagca                                        11186

<210> SEQ ID NO 5
<211> LENGTH: 10200
<212> TYPE: DNA
<213> ORGANISM: Homo sapiens

<400> SEQUENCE: 5
gccaattaga agaaacacaa ctacaaggtc agggcatatt attcaaacag tagagacaat      60
acagtcaaat atttggcaga attacaaaat atctcattgg aaaagacacg caaggggaaat    120 caacaaaaag atatgaatca gaattcatct gtgtctcaag aaaaggtcat gcgataaatt     180
aagttctgct agtgtttcta cactaccgtt agcctcatta ccttatttt taagtgttaa      240 tatagtttta ggtattttac atacattttt attattaatt acaaccaaag tgcaacttgt     300
aatagcaatt ccttcacatt ttttttttca aatcttgcac cttaaaatcc acctcgggcc     360
tcagttggcc agctttggta tctgatactt ggactacaga taccactaag gcaagtagat     420
aaaatgtact ctaggaccta cagcccttct gctagatcct gaagaatgat cattaaaaca     480
agctggtcta gctggtcaag agcaaaaata aaatcaagat gacagaaaat tgatgcaaaa     540
```

```
gtgaagtaaa atagctagag aatatgattg cgcctgtccc cttagcatgg attcccatgc    600
tagccaatct aaaatcctca ctgttagaat cctcctgtca atatgataga atgaacagca    660
agctcagtgt cagaaaacct gtgttgttaa cttggccctc tttctagctg aatgtgtgtt    720
tttggtcaag ttctttggca tttcagagac tcagagtagt gaaggaagtg ataagatga    780 cctctacatt ctccttgcaag ctcaaacatc tatgaatcca gagagaaaaa ctagagcatg    840
aaattaaggt tattttaaag aaataacctt aaaattatta gtattcgagg atctccaata    900
tattcatggc accactcaaa actttccttc tgctctatcc cgtcttggct caaagttatc    960
tccttaatga ggtctgccct gactatccta cttaaaattg taaactttgc ccacctggta   1020
cttccactct ctttcccctg ctctgttttt caccgtaata cttactcttt tttaacatac   1080
aaaatcactt atttactgtg ttgttatcta tctgcctact cttaccatca aatataagtt   1140
ctacctaggc agggattttt gtatgttttg ctcatggata tatacgaagc acttagagta   1200
atatgtgaca tatacagggt acttgattaa tactgttgag tgaatgaatg agtttccaat   1260
acaaatttaa aataaaatat ttcctaactt aaaattgtaa agtcagatct aaccaactgt   1320
tcattggtct gctagcagtg tttcttgtat atggaaatat attttaaata gatatgtcct   1380
gtgaaataat actaagtgtt ctaaagaaat aagtgagtga acgttacctc attgaactaa   1440
cttgaccttg ctcctgggag agagttcatt tgagattaaa caagttcaaa gtctatgaat   1500
cataaaacga taaaaaaaac taaagggaa atggtgtttt tataagctct gcaattcaaa   1560
agccatttcg ggtaatattg ttattttat gtcaggaatt cctcagtgct gatatcttag   1620
ggcaaagggt ttggttataa attaagagaa tgaggaaata ggtacatagt aggattgttc   1680
caaccaaata tgtgttgaat gtcaaaggaa tttccctgag gaataatctt cagaataatt   1740
tgctaagcac aggagaaaat ttggcttatt actttatagc cagatttcat ttttaattga   1800
aacttctttc aagcaaatca cttactagtc tattaacaat aacaacataa acacaagtaa   1860
acattcggaa tatagacatc caggtactaa gctgattgct ttacactcac tgtcttattt   1920
tacaagtaag gagttttagt tgcagcaaaa gaaataaatt ttccaatgtc aaatgaccag   1980
aacttaaacc caatctgttt ggtgctaaag ccaatgttct ttactgcaat gttgggttat   2040
cttgtttcta aaacttaaat ttatcagtaa aaggcaaaat ttgctattat tgaggacatt   2100
aaaatcatat ttttgtagac tctgaggaca atccaacaa aaaagttcca actatttctt   2160
ggcaggcatc attgaaattg gtatatagct tccttgggta ttgactttga aaaggaagtt   2220
ggtcacttta gatatataag ttcagtctgt ttgtaaaaac aaaatgaaaa caaaacagtt   2280
gccttatatg ctaaaattat cctaatcgtt ttcaccttta acaacatata cacacagaac   2340
ttgaggaact ttacacggct catcttcata ttgtcagcat ctagcaaagt acttgccaca   2400
tagtgatcaa taaagttttt agccagcctg ggcaacatag tgcagccta tctctacaaa   2460 aaaaaattag ccaggcaagg tggcgcacac ctttggtccc agctacttga gaggaggatg   2520
tggggagatc ctttgaatgc aggaggttga ggctgcagtg agctgtgatt gcgccactgt   2580
gcttcaacct tggtgacaga gcaagaccct gtctcacaca cacacaaatt aagtaaagaa   2640
aaaaaaaaga atcaaagaaa aaaataattc cccagcttaa gtccatcttt atttgtttgg   2700
ataagctata aagtgtcaaa taatgctgtt aatggacatt tctctagctc tcccaaagga   2760
ggaattgagc acatagtatg tgctgtattt tatatacaga ataaaaatag agacaagatt   2820
tctaccctca cagaacttaa attcttcagg agaatgacac tgaagtcctt aattggactt   2880
```

```
ctctcttctg tattatcttc ctcaagtgga ggtatatggt gcttagttat gaaaaatacc    2940
tccagggctt tgatcttctc aataactctt tgaggctgat atgaaaacag taattagaaa    3000
aaaaccatgt atccaactta tatagacagt tgatgaccaa agctagaatc cagttatttc    3060
agcctcccat gtatttctt  attacttaag gagaatctct atctctacct ctttctctct    3120
tcttcctctc tcactttct  tagaaacatg ggtaagattt tcagaaatat gagaaactta    3180
ttaataaatg aaaaatactg ggaattctca atgtttcttg ttttagccag ttaattttgg    3240
ccttcattca atgtgagtgt cccttaataa ggagcaaact ccactgagag atagatacta    3300
ataaccagga ttctgaaaat gcattctcat ccccatctcc aaactttat  aaaaaatatt    3360 ataaaataat cacttttaa  tataggaaat ttctcaaata cagaaaaaat taaagtaaac    3420
tcagacctaa ctttcatcac taaaagataa tcactcttga cactttgata tcttatctc     3480 taatattaca ccaattaatt tgcttgatat agtgaatatt atgctattat aattttcccc    3540
tgccttttgt ccttgcatat tagcataggt attttctgag gttatcacaa actctgtaag    3600
cacgttttat attactactt ttttaaagag gatgtataat aattaattca tccatatata    3660
tgtggttaag tattcaggtc actgctcatt tttcactgtt ataaaataaa gcagcaatga    3720
ataccttggg ctgatatttt tttctgtact tggaattatt tctttaagat agatttccta    3780
aaattgaatt actgagtcaa acagacttaa gttttcctta tgtatgtttc cttattcatt    3840
tgaataattt tcaactccta cttgtttatt taactcttgt gagcatgtga tagtctcatt    3900
tttcaaaata tcttttgctgt tgtaatttgc atttctttgt agttagcatg aatatttcag    3960
tatgttttct tctgtgtacc agtatactac atactttttt atatgaattg cctatttgca    4020
tcttttgctc ggttctatta gacctttgaa ttttttctta tccatttata taagctcttt    4080
atatattaag aatattaacc tattgtgata tttgcaataa atagctatat ggtttgttgt    4140
tggttttaaa tgtgaattta ttcaattttc ttcataattt tgttgttttt atagatttct    4200
ttaaaagtaa taaaattatt gccatattat tatttatttt caatgtccat tactagccct    4260
ttccagtcat cacttttact ctcatgttct taatttttat tcatatcttg gctccattga    4320
ccatctttat taggatattt gggaaataat acaatttata ctaaacacac atcaaatctt    4380
accttatttt cttcttacaa aaaccctagg aatatgctgt ttttgtcttt atttgaatga    4440
cacagaaatc aaggtttttg agcagtggag tatttcttca aatgacacag aaatcaagtc    4500
ttttgagcag tggagtattt cttcaaagcc acacagctag taagtcatga agctggaatt    4560
ccaagagttg ccacttcatt ttcttctttc cctttatctt actcagttgt cttctctcct    4620
cttaattttg tcattcattt aaaaacattt cttgtgctat tatggtagat ttattttaat    4680 aggggcagt  gacttactca gagagatgat tctctaatgg agttttaaag atcttagaag    4740
ttgatagagg aggctgggcg tggtggctca tgcctataat cccagcactt tgggaggctg    4800
aggtgggtgg atcacttgag gccagaagtt caagatcagc ctagtcaatg tggtgaaacc    4860
ccatttctac taaaattaca aaaattagcc tggtgtgctg gtgcactccc ataatcccag    4920
ctactcagga ggctgaggca tgagaattgc tggaacccag gaggcggagg ttgcagtgcg    4980
cctggattat taacactaca ctccagcctg ggagacagag taatactcca tctcaataaa    5040
aagaagttga taagggagat agttcatggc aacggatctt tgaaggcacg ctaatgataa    5100
cttaggcatt tagcctacta gtgtaatttc cataaatctg cctctgatgt catactctca    5160
gcacctaata ttttctacaa acattttattg aaacttattt ttgtataagt ctctgtccag    5220
tttgaatatt taaaaaattc ataatcatat gaaacattaa taataaatac aaaatgagag    5280
```

```
atgccgatac tgaaaagtag gattgcggag tggtagaaaa tatttctggc tgtagtagat    5340
ggggaagtgt tcaaagagga gtataattca ggtttccatt tgccatcgac ttatcacatg    5400
gctaactcac taagcgactt aattaaaatt aaattaattt atcatcatct gatcaccatt    5460
tcacacaact catgtctgtt gctgtattgg ctaaatgatg gcaagacaaa cgacctctga    5520
aaatgatcct attgaccttc ggaatctgga ttttttttc aatgcaggtg tccatagaag    5580
caatctgatg taatccaaca tgagttcaag cacagtcatt aatatcccc tatcaagtac    5640
agtcatttaa tatcccctat catcacatgt ccttcataca taaaaatcat tacatgtgaa    5700
agggtggaga gtgtgtggat cccttattat tgtgttattg taacacaata acaatattgt    5760
gttattattg ttaacacaag tgagtcatat gtcttgctct ttggactgag tggaaacttg    5820
tattctttct ctgcctcagg tcaattaact tcattgaggt gagttgcatt ccttctttaa    5880
gcatgttgaa ccttcaatct ggactcagat gggctaaata gaggagctag gaaaaataca    5940
gaaaataaat tattagagag atcagagaaa gatacataag atttacaata aagaattat    6000
gagaaaaaca tccaaaagaa ttaaaaacca taggagaagg aaaaataggt gaacagcttt    6060
ttaatttcta taaatgtgtt gttaatactc ataataaagg actcagagct gggatatgag    6120
aataataggt caaacgtata tggatacata gatgtgacta catacatgag ttgcaaagaa    6180
tgctaaggag ggcaaaaaga gattgagaag agggcattat tactaatata tagcaatgtt    6240
gaatgtttag ggtgtttcag gcactgtaca aatctttaa atacacaaat cacttaatct    6300
tgccataaca ttagaagata ctatctactc tttaccaaaa aggtaactgt gggatagcag    6360
agttaagtaa cccgttcaaa cctatgcata taatcagca gagatggtcc ttatctaagt    6420
ttttctgcct ttgaagtcca aatagtttaa tgcagccagg tactaaagaa gaaaactttt    6480
gtaaattagt ttagtttaat gatttacatg tggaaaagca cagagtgaaa agcacatatc    6540
atctgagaag cccagtgagt ttggctgaaa tggagtgaac atgtacatgt tgagggtgag    6600
gaagatgatt agagagaagt gatgtgttgt ggttcttaaa agctaagagg aaactgttag    6660
atatgatata gtctgtggca gggagccatt gcaggttttc caagatggac tcataaggag    6720
aaaacacttc gtgggactgg aaaaggcagt gaagtggtgt gtcctatgat aatgtactac    6780
agtgtaggat agtggttaag agtacagtta tgagagaggg actactggtt agcaccttac    6840
ctgctgtgtg actgggcaaa taatgcaaac ctcagtgtct tttattgtaa tatgggagta    6900
acaaaaatag taactacttc ataggattct tgtaaagatt aaatgactta atttctttga    6960
agtgcttggc agttcctgat aaatgaccag tagttaataa atgttagttg ttattattat    7020
cattatatat tattactccc atagatacat atagaacaga ctgcagcaga gaggcaaatc    7080
tttaatgttg tcagagtata gacaagttgg tgaaatggct acatgagagc ggaggacaag    7140
aaggtgcaga ttgtggcagt cacttcaaat ggaaatatca ccgcttgaat gaaggtatat    7200
gagtgtcaac ttgcaagggg accaggtagg tttcatcaga aattaaggaa gcttaaggag    7260
aacagccaag ttcagcttga cagaagtggt ggtggcacaa atgcaagact ggtgtctttc    7320
aagaaaccaa ggactgttga agtagcaag agctagtttg ttttaggtcc atcatgtttt    7380
atattcacac tttcatgtca gtggagcaaa gaaatggaat acaatataat agaatggtag    7440
aatcttattt ttaaaatctg tgttattctg atctttaact tacttatatc tttgatagag    7500
atctttacct gatgctcaag attgtagaaa tagtataatc aacataacag tatagcactg    7560
tatttatatc ctgcactgtt tagggagggt ttaaggccat tcaaaggat acataaaata    7620
```

```
caacaagatt acataaatga aaggtgagat aaagcaacaa agcaaaacaa aagtgaaaac    7680
agagatcata ggcacaaata agattaaaaa cgcatgtaat gaagatgaaa gcttttacat    7740
ttacccagat tggaccacag ggttgttgtt aagcctttaa acagtgaaca atgctgtaca    7800
cttgcatatg caattagaac atgtggaaaa aatagtggcc tgttagaagc ctaattaaca    7860
atttgtgaaa aaaaaaaaa aaaaaaaaaa aagaggccga gctgtagctc acgcctgtaa    7920
tccctgcact ttgggaggcc gaggcgggcg gatcacgagg tcaggagatc aagaccatcc    7980
tggctaacac agtgaaaccc agtctctacg aaaaatacaa aaaattagcc gggcgtggtg    8040
gcgggagcct gtagtcccag ctacctggga ggctgaggca ggagaatggt gtgaacccgg    8100
gaggcggagc ttgcagtgag ccgagatcct gccactgcac tccagcctgg gcgacaaagc    8160
aagactccgt ctcaaaaaag aaaaagaaa gaaaaacaaa agaaaacttc attgtattgt    8220
aaggccaaga acaaaatata tcaagataag gaaaatttgt agtcaagaat agaaaaaaat    8280 tatgctttg aagtatgagt tatttaaaga aagtggaaac atcctcagac tatgcagtaa    8340
aaaacaaagt gattttcttc ttctaaactt atgcaataaa ctgataggta atatgtgaaa    8400
gtcatagaat gtagactaga ggatacaaca aacctatttc ctctatgttc ataagaagta    8460
agaaaagctc tgatgtgagt tagcattgct ttacaatttt gaattgtgca gattgcacgt    8520
acttttcctc agtttgaagt aaatagtgga caggaaaaaa tattaaatgt tggcagtaaa    8580
tatggaagga aattacaact aatgtaatat gctaaaacat gctatgttta ttttactaat    8640
ttgaattaaa atgtaagaat ttaaaatgcc ctggaaaaac acgggcattg atctgacgtc    8700
tgaagtttta aaatattaca cactttgaaa tagcatttgt accttgaaat acctgtctct    8760 atatatttt taaaacttcc tttttctttc attccattta tcatcaaaata aaggatgaac    8820 agatgtaact cagaaactgt caagcatgct gaagaaagac cactgcagaa aaatttctcc    8880
tagccttttc aaaggtgtta ggaagcagaa aggtgataca gaattggaga ggtcggagtt    8940
tttgtattaa ctgtattaaa tgcgaatccc gagaaaattt cccttaacta cgtcctgtag    9000
ttatatggat atgaagactt atgtgaactt tgaaagacgt gtctacataa gttgaaatgt    9060
ccccaatgat tcagctgatg cgcgtttctc tacttgccct ttctagagag gtgcaacgga    9120
agccagaaca ttcctcctgg aaattcaacc tgtttcgcag tttctcgagg aatcagcatt    9180
cagtcaatcc gggccgggag cagtcatctg tggtgaggct gattggctgg gcaggaacag    9240
cgccggggcg tgggctgagc acagccgctt cgctctcttt gccacaggaa gcctgagctc    9300
attcgagtag cggctcttcc aagctcaaag aagcagaggc cgctgttcgt ttcctttagg    9360
tctttccact aaagtcggag tatcttcttc caaaatttca cgtcttggtg gccgttccaa    9420
ggagcgcgag gtagggcac gcaaagctgg gagctactat gggacagttc ccaagtgtca    9480
ggctttcaga tttcctgaac ttggtcttca cgggagaagg gcttcttgag gcgtggatag    9540
tgtgaagtcc tctggcaagt ccatggggac caagtggggt tagatctaga ctcaggagct    9600
cctggagcag cgcccaaacc gtagtggcac tggaccatgt tgcccggagc gcgcacagcc    9660
cgcgcggtgc ggggacctgc tctctgagcc cgcgggcggt gggtgggagg aagcatcgtc    9720
cgcggcgact ggaaccggga gggagaatcg cactggcggc gggcaaagtc cagaacgcgc    9780
tgccagaccc ccaactctgc cttcgtggag atgctggaga cccgcgcac aggaaagccc    9840 ctgcagtgcc catcgcggcc agagcagctg gggcatcaac ggcgggcgct ccctcttact    9900
gctctctggt ttcgacgggg gactagaggt tagtctcacc tccagcgcgc ctgaggctca    9960
tgcatttggc taatgagctg cggtttctct tcaggtcgga atggatcttg aagggaccg    10020
```

```
                                        -continued
caatggagga gcaaagaaga agaacttttt taaactgaac aataaaaggt aactagcttg  10080
tttcattttc atagtttaca tagttgcgag atttgagtaa tttatttcta gcctccagct  10140
ctgaaataaa tgacatgttg ttgtttttaa ttatttttaa gaaacgcaag ctagcctttg  10200
```

US 7,531,712 B2

P450 GENE REGULATION

CROSS-REFERENCE TO RELATED APPLICATIONS

This application is related to U.S. patent application Ser. No. 09/700,991, now U.S. Pat. No. 6,984,489 B1, and U.S. patent application Ser. No.11/324,921.

TECHNICAL FIELD OF THE INVENTION

The invention relates to the generation of a transgenic animal and to the use of the animal for determining the effect of a compound, particularly, but not exclusively, a xenobiotic or steroid, on the regulation of expression of a P450 gene in a human.

BACKGROUND OF THE INVENTION

Many endogenous and exogenous compounds are observed to have a therapeutic effect in drug development trials in vitro. However, the intended therapeutic effect is often not realised in clinical practice, for example, when compounds are co-administered, because certain compounds induce the expression of the CYP3A4 gene. This induction generates CYP3A4 cytochrome P450 molecules which metabolise compounds before the intended therapeutic effect of each compound can be realised. Accordingly, induction of expression of the CYP3A4 gene interferes with intended dosage, leading to therapeutic failure or sub-optimal treatment.

Induction of CYP3A4 gene expression is a significant problem for drug development because time, resources and expense are wasted in the development of candidate drugs for therapy of particular disease conditions which will ultimately fail or perform sub-optimally in clinical practice.

It would be advantageous to have an animal model for use in drug development trials from which, at an early stage of drug development, one could determine whether a candidate drug would be likely to achieve an intended therapeutic effect in a human.

Such an animal model would not be useful unless at least some of the aspects of the regulation of CYP3A4 gene expression in the human, especially tissue specific expression, are reproduced. This is because in the human, the CYP3A4 gene is expressed in specific tissues, including liver and small intestine, which many compounds inevitably come into contact with when administered for the purpose of therapy. Accordingly, one would be unable to determine whether the bio-availability of a candidate drug would be sufficient for achieving an intended therapeutic effect in clinical practice in a model which does not reproduce the constitutive and xenobiotic induced tissue specific expression of the CYP3A4 gene that is observed in the human.

WO99/61622 and Goodwin et al. 1999 disclose a nucleic acid molecule located 8 kb upstream from the initiation of transcription site of the CYP3A4 gene which regulates transcription of the CYP3A4 gene in response to xenobiotic compounds. These documents do not disclose elements for regulating the constitutive and xenobiotic inducible tissue specific and developmental expression of the CYP3A4 gene observed in a human.

There is a need for an animal model which reproduces at least some aspects of the expression of the CYP3A4 gene in a human, for determining whether a compound, for example, one identified in a drug development trial, would be likely to induce CYP3A4, and hence cause drug-drug interactions, or auto-induction of the metabolism of the drug under study.

DESCRIPTION OF THE INVENTION

The invention seeks to address the above identified need and in a first aspect provides a non-human mammal comprising:
  (a) a regulatory nucleic acid molecule which is capable of regulating transcription of the human CYP3A4 gene and which comprises a nucleotide sequence that is identical to a sequence of the human CYP3A4 gene located between the initiation of transcription site of the gene and a position located at least 13,000 nucleotides upstream from the site; and
  (b) a reporter nucleic acid molecule for producing a detectable amount of a reporter molecule for indicating regulation of transcription of the reporter nucleic acid molecule by the regulatory nucleic acid molecule wherein the reporter and regulatory nucleic acid molecules are arranged to permit the regulatory nucleic acid molecule to regulate transcription of the reporter nucleic acid molecule.

As described herein, the inventors have found that the incorporation of a region of the human CYP3A4 gene that is located between the initiation of transcription site of the gene and a position 13,000 nucleotides upstream of the initiation of transcription site into an animal model provides the animal with sufficient genetic information for reproducing the constitutive and xenobiotic induced tissue specific expression of the CYP3A4 gene that is observed in humans. More specifically, the inventors have generated animal models which contain a transgene comprising this region and have observed that these models provide constitutive and xenobiotic inducible expression of a transgene in a tissue pattern which reproduces the tissue specific expression of CYP3A4 which is observed in a human. Importantly, the level of constitutive expression is sufficient to allow one to observe the effect on the regulation of tissue specific transgene expression, of administration of a compound, for example, a xenobiotic or steroid, to the animal.

Further, the inventors have observed that the animal models described herein also reproduce aspects of the constitutive and xenobiotic inducible developmental expression of the CYP3A4 gene that is observed in humans.

These findings are unanticipated because prior to the invention, there was no suggestion that the genetic information required for simulating the constitutive and xenobiotic induced tissue specific or developmental expression of the CYP3A4 gene that is observed in a human would be contained in the region of the human CYP3A4 gene between the initiation of transcription site of the gene and a position 13,000 nucleotides upstream of the initiation of transcription site.

Further, prior to the invention, differences in the induction profile of the mouse CYP3All and the human CYP3A4 gene had been observed, and differences had also been observed in the ligand binding profile of mouse transcription factors, especially PXR and CAR, and human PXR and CAR. Accordingly, there was no suggestion that a non-human animal would have factors sufficient for interacting with a region of the CYP3A4 gene for reproducing the constitutive and xenobiotic induced tissue specific or developmental expression of CYP3A4 observed in a human.

Further, prior to the invention, mechanisms associated with transgene integration had been observed, such as gene silencing and mosaic transgene expression which limited the extent to which an a transcriptional enhancer element incorporated into a trangenic model could reproduce regulation of gene expression observed in a human. Accordingly, there was no suggestion that a region of the human CYP3A4 gene would be capable of reproducing the regulation of expression of the CYP3A4 gene that is observed in a human. However, as described herein, the inventors have shown in 2 separate founder lines that the expression of the transgene reproduces aspects of CYP3A4 gene expression that are observed in humans.

Thus in a second aspect, the invention provides a non human mammal comprising:
(a) a regulatory nucleic acid molecule comprising a nucleotide sequence that is identical to the nucleotide sequence of the human CYP3A4 gene that extends about 13,000 nucleotides upstream from the initiation of transcription site of the gene; and
(b) a reporter nucleic acid molecule for producing a detectable amount of a reporter molecule for indicating regulation of transcription of the reporter nucleic acid molecule by the regulatory nucleic acid molecule wherein the reporter and regulatory nucleic acid molecules are arranged to permit the regulatory nucleic acid molecule to regulate transcription of the reporter nucleic acid molecule.

In one embodiment, the regulatory nucleic acid molecule comprises the sequence shown in SEQ ID NO:1.

Further, as described herein, the inventors have generated transgenic animals which contain a region of the human CYP3A4 gene between the initiation of transcription site and a position about 3,200 nucleotides upstream of the initiation transcription site and observed that the transgene is not constitutively expressed or inducible by xenobiotics in these animals. Accordingly, the inventors have found that the genetic information required for reproducing the constitutive and xenobiotic induced tissue specific and developmental expression of CYP3A4 observed in a human is contained in the region of the human CYP3A4 gene between the position located about 3,200 nucleotides upstream of the initiation of transcription site of the gene and a position 13,000 nucleotides upstream of the initiation of transcription site.

Thus, in a third aspect, the invention provides a non-human mammal comprising:
(a) a regulatory nucleic acid molecule comprising a nucleotide sequence that is identical to the sequence of the human CYP3A4 gene that extends about 8,000 nucleotides upstream from a position about 3,000 nucleotides upstream from the initiation of transcription site of the gene; and
(b) a reporter nucleic acid molecule for producing a detectable amount of a reporter molecule for indicating regulation of transcription of the reporter nucleic acid molecule by the regulatory nucleic acid molecule wherein the reporter and regulatory nucleic acid molecules are arranged to permit the regulatory nucleic acid molecule to regulate transcription of the reporter nucleic acid molecule.

In one embodiment, the regulatory nucleic acid molecule comprises the sequence shown in SEQ ID NO:2.

In a fourth aspect, the invention provides a non-human mammal comprising:
(a) a regulatory nucleic acid molecule which is capable of regulating transcription of the human CYP3A4 gene and which comprises a nucleotide sequence that is identical to the sequence of the human CYP3A4 gene that extends about 600 nucleotides upstream from a position about 7,200 nucleotides upstream of the initiation of transcription site of the gene; and (b) a reporter nucleic acid molecule for producing a detectable amount of a reporter molecule for indicating regulation of transcription of the reporter nucleic acid molecule by the regulatory nucleic acid molecule wherein the reporter and regulatory nucleic acid molecules are arranged to permit the regulatory nucleic acid molecule to regulate transcription of the reporter nucleic acid molecule.

In one embodiment, the regulatory nucleic acid molecule comprises the sequence shown in SEQ ID NO:3.

In another embodiment, the regulatory nucleic acid molecule has the sequence of any one of the following fragments of the CYP3A4 gene:
(i) a fragment consisting of from nucleotide positions −13,000 to +53;
(ii) a fragment consisting of from nucleotide positions −13,000 to −12,700 contiguous with −8000 to +53;
(iii) a fragment consisting of from nucleotide positions −13,000 to −5,100 contiguous with −1,200 to +53;
(v) a fragment consisting of from nucleotide positions −7,800 to −6,00.0 contiguous with −362 to +53;
(vi) a fragment consisting of from nucleotide positions −7,500 to −6,000 contiguous with −362 to +53;

A regulatory nucleic acid molecule which has the sequence of a fragment consisting of from nucleotide positions −7836 to −7207 contiguous with −362 to +53 is particularly preferred, as this construct contains the minimal sequences necessary for regulating transcription of the human CYP3A4 gene, more specifically, an element responsive to xenobiotics (the "Xenobiotic Response Element Module" or "XREM") and the proximal promoter of the CYP3A4 gene.

The regulatory nucleic acid molecule of the invention typically contains at least one enhancer capable of regulating transcription of a human CYP3A4 gene when contacted with a nuclear receptor. Examples of such enhancers are those capable of regulating transcription of a human CYP3A4 gene when contacted with a nuclear receptor bound to a ligand, such as a xenobiotic or steroid. Other examples are those capable of regulating transcription of a human CYP3A4 gene when contacted with a nuclear receptor consisting of a heterodimer of PXR (pregnane X receptor, otherwise known as SXR (steroid and xenobiotic receptor)) and RXR (9-cis retinoic acid receptor), or CAR (constitutive androstane receptor-β) and RXR.

The inventors believe that certain nucleic acid molecules which have substantially the same nucleotide sequence as a regulatory nucleic acid molecule of the invention would also have sufficient genetic information for reproducing the constitutive and xenobiotic induced tissue specific and developmental expression of the CYP3A4 gene that is observed in a human. Accordingly, it will be understood that nucleotides could be modified or deleted in regions of the regulatory nucleic acid molecule, more specifically, those regions which do not contain an enhancer such as those described above, without significantly limiting the capacity of the molecule to regulate transcription of the human CYP3A4 gene.

The inventors recognise that it would be advantageous to provide an animal model further capable of reproducing the expression of other human genes, specifically those genes encoding products which modify or modulate the therapeutic activity of exogenous and endogenous compounds used for therapy and cause drug-drug interactions, for example, cytochrome P450 genes or ABC transporter superfamily genes, for example, β-glycoprotein (otherwise known as MDR-1). The regions controlling the constitutive and xenobiotic induced tissue specific expression of some of these genes are known, and in some instances, non-human animal models have been generated. The inventors recognise that the genetic background of these animals could be incorporated into the non-human mammal of the present invention, for example, by conventional breeding techniques.

Thus in a fifth aspect, the invention provides a non-human mammal of any one of the first to fourth aspects of the invention, further comprising:
(c) a further regulatory nucleic acid molecule which is capable of regulating transcription of a human gene; and
(d) a further reporter nucleic acid molecule for producing a detectable amount of a further reporter molecule for indicating regulation of transcription of the further reporter nucleic acid molecule by the further regulatory nucleic acid molecule wherein the further reporter and further regulatory nucleic acid molecules are arranged to permit the further regulatory nucleic acid molecule to regulate transcription of the further reporter nucleic acid molecule.

In one embodiment, the at least one further regulatory nucleic acid molecule has a sequence shown in SEQ ID NO:4. In another embodiment, the at least one further regulatory nucleic acid molecule has a sequence shown in SEQ ID NO:5.

Although the regulatory nucleic acid molecule of the invention described herein is sufficient for reproducing the constitutive tissue specific and developmental expression of the CYP3A4 gene that is observed in a human, the inventors recognise that aspects of the xenobiotic inducibility of the gene could be better reproduced in an animal by incorporating at least one human transcription factor that is capable of interacting with the regulatory nucleic acid molecule for regulating transcription of the human CYP3A4 gene. Examples of such factors are nuclear receptors. These receptors may be those capable of regulating CYP3A4 gene transcription in a human when the receptor is bound to a ligand, such as a xenobiotic or steroid. One example of such a receptor is the human PXR (pregnane X receptor, otherwise known as SXR (steroid and xenobiotic receptor)). Another suitable receptor is the human CAR (constitutive androstane receptor-β). Non-human animals comprising a human PXR or CAR receptor are known. The inventors recognise that the genetic background of these animals could be incorporated into the non-human mammal of the present invention, for example, by conventional breeding techniques.

Thus in a sixth aspect, the non-human animal of the invention further comprises at least one human transcription factor for regulating transcription of a human CYP3A4 gene. Preferably the transcription factor is a nuclear receptor. Preferably, the nuclear receptor is a heterodimer of the human PXR (pregnane X receptor, otherwise known as SXR (steroid and xenobiotic receptor)) and human RXR (9-cis retinoic acid receptor) or human CAR (constitutive androstane receptor-β) and human RXR.

It follows that the reporter nucleic acid molecule can be any molecule which is capable of detection when the reporter nucleic acid molecule is transcribed. For example, the reporter nucleic acid molecule could be the CYP3A4 cytochrome, or the mRNA transcript which is translated to produce the cytochrome. Those reporter molecules which are commercially available, including firefly luciferase, β-galactosidase, alkaline phosphatase, green fluorescent protein or chloramphenicol acetyl transferase can be used.

Thus in one embodiment, the reporter nucleic acid molecule is capable of producing a reporter molecule selected from the group of reporter molecules consisting of firefly luciferase, β-galactosidase, alkaline phosphatase, green fluorescent protein or chloramphenicol acetyl transferase.

While the non-human mammal of the invention, as exemplified below, is a mouse, the inventors believe that any other non-human mammal could be used in the invention, especially those for which standard transgenic techniques have been developed including for example, rat and rabbit. However, typically the non-human mammal is a mouse.

In another aspect, the invention provides a tissue of a non-human mammal of the invention.

In one embodiment, the tissue is an embryo capable of producing a non-human mammal of the invention.

In a further aspect, the invention provides a method of determining whether a compound is capable of effecting the transcription of a human CYP3A4 gene the method comprising the following steps:
(a) administering the compound to a non human mammal according to the invention and
(b) determining whether the reporter molecule is produced by the reporter nucleic acid molecule in the mammal.

In one embodiment, the production of the reporter molecule indicates that the binding compound is capable of effecting the transcription of the human CYP3A4 gene.

Any compound can be tested in the method however, preferred compounds are xenobiotic or steroid compounds.

The inventors recognise that a non human animal which comprises a 5' flanking region of CYP3A4 gene but which is deficient for the region from −7836 to −7207 would be useful as a negative control in a method for determining whether a compound is capable of regulating transcription of the human CYP3A4 gene.

BRIEF DESCRIPTION OF THE FIGURES

FIG. 1. CYP3A4/lacZ transgene constructs used to generate transgenic mice. The upstream regions of the human CYP3A4 gene are depicted as open boxes with the position of the XREM at approximately −7.5 kb of the CYP3A4 gene indicated by cross-hatching. The 5'-flanking region extended from 56 bp downstream of the transcription initiation site to a HindIII site at −3,213 in the construct designated −3CYP3A4/lacZ and to a KpnI site at −12,926 kb in construct −13CYP3A4/lacZ. The coding region of the E.coli lacZ gene together with eukaryotic translational initiation and termination signals, transcription termination and poly adenylation sites are indicated by a solid box.

FIG. 2. Xenobiotic induction of hepatic transgene expression. Female mice from line 9/4 harbouring the −13CYP3A4/lacZ transgene were treated with various reagents. Histochemical staining of liver slices with X-gal revealed an increased zone of blue staining cells containing β-galactosidase after treatment with rifampicin, phenobarbital and pregnenolone 16α-carbonitrile compared with corn oil treated mice.

FIG. 3. Comparison of the xenobiotic induction profile of the −13CYP3A4/lacZ transgene with the mouse Cyp3all gene. Transgenic mice from line 9/4 were treated with a range of xenobiotic reagents and naturally occurring steroids. A. Transgene expression was assessed by determining β-galactosidase activity in total liver lysates using the ONPG assay. The units of β-galactosidase activity are given as $A_{420}$/mg liver/minute. Dexamethasone and pregnenolone 16α-carbonitrile were the most potent xenobiotic activators of the −−13CYP3A4/lacZ transgene, while rifampicin treatment resulted in relatively low levels. The steroids pregnenolone and 17α-progesterone were very weak inducers. B. Hepatic expression of the endogenous mouse Cyp3all gene was examined in the same mice by Northern analysis. A similar pattern of induction to the CYP3A4/lacZ transgene was observed with both xenobiotic and endogenous regulators. The data are presented as the mean ± the standard deviation for 3 animals.

FIG. 4. Dose response of −13CYP3A4/lacZ transgene expression after treatment with dexamethasone. A. Male mice from line 9/4 were treated with from 1 to 100 mg/kg dexamethasone. Higher doses of dexamethasone resulted in increased β-galactosidase activity (determined in liver lysates as described in FIG. 3).B. Zonal expansion of transgene expression with increasing doses of dexamethasone. X-gal staining of frozen liver sections revealed greater numbers of hepatocytes containing transgene-derived β-galactosidase activity after treatment with 1, 10 and 100 mg/kg dexamethasone. At low doses there are limited numbers of transgene expressing cells immediately adjacent to the central vein. With higher doses there are more cells committed to transgene expression extending across the liver lobule towards the portal tract.

FIG. 5. (SEQ ID NO:1) Sequence of the CYP3A4 5'-flanking region included in the −13 CYP3A4/lacZ construct. This sequence corresponds to −12,926 to +56 base pairs relative to the transcription initiation site of the CYP3A4 gene.

FIG. 6. (SEQ ID NO:2) Sequence of the 5'-flanking region of the CYP3A4 gene extending from −12,926 to −3,213 base pairs and representing the difference in sequence between the −13 CYP3A4/lacZ and the −3 CYP3A4/lacZ constructs.

FIG. 7. (SEQ ID NO:3) The "Xenobiotic-Responsive Enhancer Module" (XREM) of the human CYP3A4 gene. This region encompasses −7836 to −7207 base pairs relative to the transcription initiation site of the CYP3A4 gene.

FIG. 8. (SEQ ID NO:4) The 5'-flanking region of the human CYP3A7 gene (Genbank Accession No. AF329900). The extent of the sequences is −11,133 to +52 base relative to the transcription initiation site of the CYP3A7 gene.

FIG. 9. (SEQ ID NO:5) Sequence of the 5'-flanking region of the human MDR1 gene (β-glycoprotein gene) encompassing −10,000 to +200 base pairs relative to the transcription initiation site of the MDR1 gene. Sequence derived from within Genbank sequence Accession Number AC002457.

An embodiment of the invention is now described in the following Example which will be understood to merely exemplify and not to limit the scope of the invention.

EXAMPLE

Materials and Methods

Transgene constructs. Two transgene constructs were synthesized with the upstream 5' flank of the human cytochrome P450 CYP3A4 gene linked to the *E. coli* lacZ reporter gene (FIG. 1). The first construct, designated −3CYP3A4/lacZ, contained the region of the CYP3A4 gene from the HindIII site at −3213 bp relative to the transcription start site to nucleotide +56 bp downstream of the transcription start site. The other construct, designated −13CYP3A4/lacZ, included the region of the CYP3A4 gene from the KpnI site at −12,926 bp upstream to +56 bp downstream of the transcription start site. It includes the DNA sequences of the XREM region located between −7836 and −7208 in addition to the proximal promoter of the CYP3A4 gene. The DNA-sequence of the CYP3A4 gene between −10468 bp and +906 bp has been determined and deposited with the GenBank/EMBL/DDJB database under accession number AF185589.

Additional sequence information covering the region—10,469 bp to −12,926 bp was obtained from publically accessible Genbank files. The *E.coli* lacZ reporter gene comprises the coding region for the bacterial enzyme β-galactosidase flanked by DNA sequences for eukaryotic translational start and stop signals, SV40 transcriptional termination and polyadenylation signals and an intron. The CYP3A4/lacZ transgene constructs were released from vector sequences and purified on agarose gels prior to microinjection Generation of transgenic mouse lines. Mice carrying the CYP3A4/lacZ transgenes were created by microinjection of the DNA constructs into the pro-nuclei of zygotes harvested from FVB/N strain mice. Microinjection and manipulation of embryos were carried by standard techniques. Stable transgenic mouse lines were established by breeding from transgenic founders identified by Southern analysis.

Administration of xenobiotics to mice. 8-10 week old male and female mice hemizygous for the −3CYP3A4/lacZ and −13CYP3A4/lacZ transgenes were used to test the ability of a range of xenobiotics and hormones to activate expression of transgene-derived β-galactosidase. Mice were administered the following reagents and vehicles by single daily intraperitoneal injection for 4 days: rifampicin/corn oil; dexamethasone phosphate/H$_2$O; pregnenolone 16α-carbonitrile/ 2% Tween 20 in H$_2$O; phenobarbital/H$_2$O; clotrimazole/2% Tween 20; phenytoin/2% Tween 20; 17α-OH progesterone/ 2% Tween 20; pregnenolone/2% Tween 20. All reagents were supplied by Sigma Chemical Co. (St Louis, Mo.) except for dexamethasone phosphate which was obtained from Faulding (Mulgrave, Australia) and pregnenolone 16α-carbonitrile from Upjohn Co. (Kalamazoo, Mich.). The dose used for all reagents to test for induction of the transgene was 100 mg/kg body weight. Dose response studies were carried out in the range of 1-100 mg/kg with male hemizygous transgenic mice.

Analysis of transgene and mouse Cyp3a gene expression. β-galactosidase activity was visualised in slices and frozen sections of liver and other tissues by staining with X-gal (5-bromo-4-chloro-3-indolyl-β-D-galactopyranoside). Tissues were fixed in 0.25% glutaraldehyde, 0.1M phosphate buffer pH7.3, 5 mM EGTA, 2 mM MgCl$_2$: washed in 0.1M phosphate buffer pH7.3, 0.01%sodium deoxycholate, 0.025% NP40, 2 mM MgCl$_2$ and stained by incubation at 37° C. in wash solution supplemented with 1 mg/ml X-gal, 5 mM potassium ferricyanide, and 5mM potassium ferrocyanide. The level of β-galactosidase activity was determined in whole liver homogenates [100 mg fresh tissue/ml 0.25M Tris-HCl (pH 7.3)] using the O-nitrophenyl-β-D-galactopyranoside (ONPG) assay according to standard techniques. After appropriate dilution the homogenate was incubated with β-galactosidase assay reagent (0.1M sodium phosphate buffer (pH7.3)/1 mM MgCl$_2$/50 mmol β-mercaptoethanol/0.88 mg/ml ONPG) at 37° C, quenched by the addition of 1M Na$_2$CO$_3$ and the absorbance at 420 nm determined. The units of β-galactosidase activity are given as A$_{420}$/mg liver/minute.

The levels of endogenous mouse Cyp3a mRNA expression were determined by Northern analysis using a riboprobe complementary to nucleotides 852-1061 of the mouse Cyp3a11 cDNA. Filters were stripped and reprobed with an 18S rRNA oligonucleotide to normalise loading.

Results 4 transgenic lines were generated with the construct containing the −3.2 kb region of the human CYP3A4 gene linked to lacZ. Transgene-derived β-galactosidase activity was not detected in kidney, large and small intestine, spleen, lung and liver tissue from mice for all 4-3CYP3A4/lacZ transgenic lines treated with vehicle or xenobiotics (Table 1). In contrast, transgene expression was readily detected in 3 of the 4 lines carrying the −13CYP3A4/lacZ construct. Line 9/4 had a very low constitutive level in the liver, with β-galactosidase detected only in isolated hepatocytes adjacent to major blood vessels. Administration of xenobiotics resulted in robust expression in a zone of cells surrounding the central vein (FIG. 2). As the basal level of transgene expression in untreated mice in line 9/4 is extremely low, induction is obvious and is essentially an off/on process. Expression in other tissues in mice from line 9/4 was restricted to the gut, predominantly in the villi of the small intestine.

The relative degree of induction for a range of xenobiotics was analysed by determining the transgenic β-galactosidase activity in liver lysates of mice from line 9/4 (FIG. 3A). Dexamethasone and pregnenolone 16α-carbonitrile were the most potent inducers, while rifampicin activated the transgene to relatively modest levels. Phenobarbital, clotrimazole and phenytoin were intermediate inducers. The induction profile of the transgene in line 9/4 was similar to that observed for the endogenous Cyp3all gene in the same mice (FIG. 3B), likely reflecting the activation profile of the mouse rather than the human PXR. Activation of the transgene was observed with naturally occurring steroids such as pregnenolone and 17α-progesterone, however the induction was weak compared with xenobiotics.

There was a marked gender difference in hepatic transgene expression, with lower levels observed in females than in males for most reagents. Such a male-predominant pattern was not evident in the induction profile of the mouse Cyp3all gene. Indeed higher levels of Cyp3all mRNA were observed in females than males after treatment with rifampicin and pregnenolone 16a-carbonitrile. The reason for this apparent reversal in gender-related transgene expression pattern is not known. However, as Cyp3all mRNA is only just detectable in males of the FVB/N strain of mice, it may be attributed to the relatively greater degree of induction of the mouse Cyp3all gene in males compared to females (FIG. 3B).

The other line which showed significant transgene expression −15/10, had a higher constitutive level in both the liver and small intestine in untreated mice.

Expression was not detected in other organs, confirming the tissue specificity observed in line 9/4. The same set of reagents were capable of increasing hepatic and intestinal transgene expression to the same levels as in mice from line 9/4. However, the overall degree of induction was not as great as observed in line 9/4 due to the higher basal level in line 15/10. The induction profile was similar with dexamethasone being the most potent activator and rifampicin the least (data not shown).

Dose response of xenobiotic induction. The activation of transgene expression in line 9/4 by dexamethasone was dose-dependent over the range 1 to 100 mg/kg (FIG. 4A). The higher transgene-derived β-galactosidase activity in liver homogenates from mice treated with increasing doses of dexamethasone was associated with an expanded zone of cells which were stained by X-gal. At low doses of dexamethasone a ring of hepatocytes only 1-2 cells thick around the central vein expressed the transgene (FIG. 4B). With 100 mg/kg dexamethasone the zone of X-gal positive hepatocytes increased to up to 10 cells, approximately midway between the central vein and the portal triad. A similar dose-dependent expansion of hepatocytes expressing the transgene was observed with other reagents and also in line 15/10 which also contained the −13CYP3A4/lacZ construct.

TABLE 1

Expression of CYP3A4/lacZ transgenic lines

| Construct | Line No. | Copy No. | LIVER Basal | LIVER Inducible | Small Intestine |
|---|---|---|---|---|---|
| −3CYP3A4/ lacZ [ | 13 | 15 | − | − | − |
| | 24 | >100 | − | − | − |
| | 31 | 80 | − | − | − |
| | 39 | 10 | − | − | − |
| −13CYP3A4/ lacZ [ | 13/5 | 70 | − | − | |
| | 9/4 | 5 | + | ++++ | + |
| | 9/7 | 50 | − | + | − |
| | 15/10 | 8 | ++ | ++++ | ++++ |

The invention claimed is:

1. A mouse whose genome comprises a transgene, wherein said transgene comprises in operable linkage:
   (i) the regulatory nucleic acid molecule set forth in SEQ ID NO: 1;
   (ii) a reporter nucleic acid molecule encoding a reporter molecule for indicating regulation of transcription of the reporter nucleic acid molecule by the regulatory nucleic acid molecule; and
   (iii) a nucleic acid molecule encoding at least one human transcription factor for regulating transcription of a human CYP3A4 gene, wherein said human transcription factor is a nuclear receptor,
   wherein the reporter and regulatory nucleic acid molecules are operably linked such that the regulatory nucleic acid molecule regulates transcription of the reporter nucleic acid molecule.

2. A mouse whose genome comprises a transgene, wherein said transgene comprises:
   (i) the regulatory nucleic acid molecule set forth in SEQ ID NO: 2;
   (ii) a reporter nucleic acid molecule encoding a reporter molecule for indicating regulation of transcription of the reporter nucleic acid molecule by the regulatory nucleic acid molecule; and
   (iii) a nucleic acid molecule encoding at least one human transcription factor for regulating transcription of a human CYP3A4 gene, wherein said human transcription factor is a nuclear receptor,
   wherein the reporter and regulatory nucleic acid molecules are operably linked such that the regulatory nucleic acid molecule regulates transcription of the reporter nucleic acid molecule.

3. A mouse whose genome comprises a transgene, wherein said transgene comprises:
   (i) the regulatory nucleic acid molecule set forth in SEQ ID NO: 3;
   (ii) a reporter nucleic acid molecule encoding a reporter molecule for indicating regulation of transcription of the reporter nucleic acid molecule by the regulatory nucleic acid molecule; and
   (iii) a nucleic acid molecule encoding at least one human transcription factor for regulating transcription of a human CYP3A4 gene, wherein said human transcription factor is a nuclear receptor,
   wherein the reporter and regulatory nucleic acid molecules are operably linked such that the regulatory nucleic acid molecule regulates transcription of the reporter nucleic acid molecule.

4. A mouse according to claim 1, 2, or 3, wherein the reporter molecule is firefly luciferase, β- galactosidase, alkaline phosphatase, green fluorescent protein or chloramphenicol acetyl transferees.

5. A tissue of a mouse according to claim 1, 2 or 3.

6. A method of determining whether a compound is capable of effecting the transcription of a human CYP3A4 gene, the method comprising the following steps:
   administering the compound to a mouse according to any one of claims 1, 2 or 3; and
   determining whether the reporter molecule is expressed by the reporter nucleic acid molecule in the mouse.

7. A method according to claim 6, wherein the expression of the reporter molecule indicates that the compound is capable of effecting transcription of the human CYP3A4 gene.

8. A mouse according to claim 1, 2 or 3 wherein the nuclear receptor is a heterodimer of human pregnane X receptor and human 9-cis retinoic acid receptor or a heterodimer of human constitutive androstane receptor-β and human 9-cis retinoic acid receptor.

* * * * *